US011208432B2

(12) United States Patent
Sun et al.

(10) Patent No.: US 11,208,432 B2
(45) Date of Patent: Dec. 28, 2021

(54) INHIBITORS OF GLUCOCORTICOID RECEPTOR

(71) Applicant: ORIC Pharmaceuticals, Inc., South San Francisco, CA (US)

(72) Inventors: Daqing Sun, Foster City, CA (US); Lawrence R. McGee, Pacifica, CA (US); Xiaohui Du, Belmont, CA (US); Liusheng Zhu, Foster City, CA (US); Xuelei Yan, Foster City, CA (US); Yosup Rew, Foster City, CA (US); John Eksterowicz, San Francisco, CA (US); Julio C. Medina, San Carlos, CA (US); Haiying Zhou, San Bruno, CA (US); Minna Delarae Balbas, San Francisco, CA (US); Valeria R. Fantin, Burlingame, CA (US)

(73) Assignee: ORIC PHARMACEUTICALS, INC., South San Francisco, CA (US)

(*) Notice: Subject to any disclaimer, the term of this patent is extended or adjusted under 35 U.S.C. 154(b) by 60 days.

(21) Appl. No.: 16/065,627

(22) PCT Filed: Dec. 22, 2016

(86) PCT No.: PCT/US2016/068448
§ 371 (c)(1),
(2) Date: Jun. 22, 2018

(87) PCT Pub. No.: WO2017/112909
PCT Pub. Date: Jun. 29, 2017

(65) Prior Publication Data
US 2021/0002324 A1  Jan. 7, 2021

Related U.S. Application Data

(60) Provisional application No. 62/387,293, filed on Dec. 23, 2015.

(51) Int. Cl.
| | |
|---|---|
| C07J 1/00 | (2006.01) |
| A61P 5/44 | (2006.01) |
| A61P 5/46 | (2006.01) |
| A61P 35/00 | (2006.01) |
| C07J 17/00 | (2006.01) |
| C07J 41/00 | (2006.01) |
| C07J 43/00 | (2006.01) |
| A61K 45/06 | (2006.01) |
| C07K 16/28 | (2006.01) |

(52) U.S. Cl.
CPC .............. *C07J 1/0096* (2013.01); *A61P 5/44* (2018.01); *A61P 5/46* (2018.01); *A61P 35/00* (2018.01); *C07J 17/00* (2013.01); *C07J 41/0083* (2013.01); *C07J 43/003* (2013.01); *A61K 45/06* (2013.01); *C07K 16/2818* (2013.01); *C07K 16/2827* (2013.01)

(58) Field of Classification Search
CPC ....... C07J 1/0096; C07J 17/00; C07J 41/0083
See application file for complete search history.

(56) References Cited

U.S. PATENT DOCUMENTS

| | | | |
|---|---|---|---|
| 4,386,085 A | 5/1983 | Teutsch et al. | |
| 4,447,424 A | 5/1984 | Teutsch et al. | |
| 4,477,445 A | 10/1984 | Philibert et al. | |
| 4,547,493 A | 10/1985 | Teutsch et al. | |
| 5,006,518 A | 4/1991 | Moguilewsky et al. | |
| 5,173,483 A | 12/1992 | Grandadam et al. | |
| 5,405,979 A | 4/1995 | Ottow et al. | |
| 5,728,689 A | 3/1998 | Cleve et al. | |
| 5,843,931 A | 12/1998 | Ottow et al. | |
| 5,843,933 A | 12/1998 | Cleve et al. | |
| 6,451,780 B1 | 9/2002 | Chwalsz et al. | |
| 6,512,130 B1 | 1/2003 | Hazra et al. | |
| 8,569,274 B2 | 10/2013 | Fauser et al. | |
| 8,648,105 B2 | 2/2014 | Jung et al. | |
| 8,658,128 B2 | 2/2014 | Altschul et al. | |
| 9,289,436 B2 | 3/2016 | Szmulewitz et al. | |
| 10,472,387 B2* | 11/2019 | Sun ..................... | C07J 41/0088 |
| 2003/0064973 A1 | 4/2003 | Patchev et al. | |
| 2004/0180869 A1 | 9/2004 | Bothe et al. | |
| 2013/0029953 A1 | 1/2013 | Nickisch et al. | |
| 2014/0148419 A1 | 5/2014 | Loumaye et al. | |
| 2014/0364600 A1 | 12/2014 | Nickisch et al. | |

(Continued)

FOREIGN PATENT DOCUMENTS

| | | |
|---|---|---|
| CN | 1222350 A | 7/1999 |
| CN | 104530166 B | 8/2016 |

(Continued)

OTHER PUBLICATIONS

Co-pending U.S. Appl. No. 17/045,413, inventors Fantin; Valeria R. et al., filed Oct. 5, 2020.
U.S. Appl. No. 16/065,626 Office Action dated Mar. 19, 2021.
Hamilton et al. Synthesis of C-11 modified mifepristone analog libraries. Mol. Diversity 11:107-111 (2007).
Nickisch et al. Synthesis and antiprogestational properties of novel 17-fluorinated steroids. Steroids 78(9):909-19 (2013).
Nickisch et al. Synthesis and biological evaluation of partially fluorinated antiprogestins and mesoprogestins. Steroids 78(2):255-67 (2013).
U.S. Appl. No. 16/065,625 Office Action dated Jan. 26, 2021.

(Continued)

*Primary Examiner* — Kamal A Saeed
(74) *Attorney, Agent, or Firm* — Wilson Sonsini Goodrich & Rosati

(57) ABSTRACT

The present invention relates generally to compositions and methods for treating cancer and hypercortisolism. Provided herein are substituted steroidal derivative compounds and pharmaceutical compositions comprising said compounds. The subject compounds and compositions are useful for inhibition of glucocorticoid receptors. Furthermore, the subject compounds and compositions are useful for the treatment of cancer and hypercortisolism.

35 Claims, No Drawings

(56) References Cited

U.S. PATENT DOCUMENTS

| | | |
|---|---|---|
| 2015/0038476 A1 | 2/2015 | Gotteland et al. |
| 2016/0151388 A1 | 6/2016 | Szmulewitz et al. |
| 2019/0218246 A1 | 7/2019 | Sun et al. |
| 2020/0055892 A1 | 2/2020 | Sun et al. |
| 2021/0017220 A1 | 1/2021 | Sun et al. |
| 2021/0023095 A1 | 1/2021 | Sun et al. |

FOREIGN PATENT DOCUMENTS

| | | |
|---|---|---|
| EP | 0057115 A2 | 8/1982 |
| EP | 0369881 A1 | 5/1990 |
| EP | 0404283 A2 | 12/1990 |
| EP | 0763541 A1 | 3/1997 |
| EP | 1285927 A2 | 2/2003 |
| JP | H01213296 A | 8/1989 |
| JP | H02188599 A | 7/1990 |
| JP | H09104696 A | 4/1997 |
| JP | 2001508079 A | 6/2001 |
| JP | 2003119154 A | 4/2003 |
| WO | WO-9504536 A1 | 2/1995 |
| WO | WO-9517192 A1 | 6/1995 |
| WO | WO-9831702 A1 | 7/1998 |
| WO | WO-2007098382 A2 | 8/2007 |
| WO | WO-2013016725 A1 | 1/2013 |
| WO | WO-2014197653 A2 | 12/2014 |
| WO | WO-2015089338 A2 | 6/2015 |
| WO | WO-2017112902 A1 | 6/2017 |
| WO | WO-2017112904 A1 | 6/2017 |
| WO | WO-2017112909 A1 | 6/2017 |
| WO | WO-2018068021 A1 | 4/2018 |
| WO | WO-2018227129 A1 | 12/2018 |
| WO | WO-2019200156 A1 | 10/2019 |

OTHER PUBLICATIONS

Hazra et al. Synthesis of 11beta-(4-dimethylaminophenyl)-17beta-hydroxy-17alpha- (3-methyl-1-butynyl)-4, 9-estradien-3-one and 11beta-(4-acetophenyl)- 17beta-hydroxy-17alpha-(3-methyl-1-butynyl)-4, 9-estradien-3-one: two new analogs of mifepristone (RU-486). Steroids 65:157-162 (2000).

Nickisch et al. Synthesis and biological evaluation of 11' imidazolyl antiprogestins and mesoprogestins. Steroids 92:45-55 (2014).

PCT/US2019/027062 International Search Report and Written Opinion dated Aug. 1, 2019.

Rew et al. Discovery of a Potent and Selective Steroidal Glucocorticoid Receptor Antagonist (ORIC-101). J Med Chem 61(17):7767-7784 (2018).

Stuchlik et al. Lipid-based vehicle for oral drug delivery. Biomed Papers 145(2):17-26 (2001).

Bachmann et al. Effect of chronic administration of selective glucocorticoid receptor antagonists on the rat hypothalamic-pituitary-adrenocortical axis. Neuropsychopharmacology 28(6):1056-1067 (2003).

Chemical Abstract Compound. STN Express RN 760141-59-1 (Entered STN: Oct. 10, 2004).

Chen et al. 3D-QSAR and Docking Study of the Binding Mode of Steroids to Progesterone Receptor in Active Site. QSAR Comb Sci 22:604-613 (2003).

Gebhard et al. 11,21-Bisphenyl-19-norpregnane derivatives are selective antiglucocorticoids. Bioorgan Med Chem Lett 7(17):2229-2234 (1997).

Geisler et al. An Efficient Synthesis of 11β-(4-Aminophenyl)spiro[estr-4-ene-17β,2'(5'H)-furan]-3,5'-dione. Tetrahedron 56(35):6489-6492 (2000).

Ligr et al. Mifepristone inhibits GRβ-coupled prostate cancer cell Proliferation. J Urol 188(3):981-988 (2012).

PCT/US2016/068431 International Search Report and Written Opinion dated Apr. 17, 2017.

PCT/US2016/068435 International Search Report and Written Opinion dated Apr. 17, 2017.

PCT/US2016/068448 International Search Report and Written Opinion dated Apr. 17, 2017.

PCT/US2017/055660 International Search Report and Written Opinion dated Jan. 24, 2018.

Richards et al. Synthesis and activity of novel bile-acid conjugated glucocorticoid receptor antagonists. Bioorg Med Chem Lett 16(23):6086-6090 (2006).

Taplin et al. A phase II study of mifepristone (RU-486) in castration-resistant prostate cancer, with a correlative assessment of androgen-related hormones BJU Int. 101 (9):1084-1089 (2008).

Du et al. Discovery of a Potent Steroidal Glucocorticoid Receptor Antagonist with Enhanced Selectivity against the Progesterone and Androgen Receptors (OP-3633). J med Chem 62:6751-6764 (2019).

Sikora. Cancer drug development in the post-genomic age. Current Science 81(5):549-554 (2001).

U.S. Appl. No. 16/562,204 Office Action dated Dec. 31, 2019.

Zips et al. New anticancer agents: in vitro and in vivo evaluation. In Vivo 19(1):1-8 (2005).

Catteau et al. Expression of the glucocorticoid receptor in breast cancer-associated fibroblasts. Mol Clin Oncol 5(4):372-376 (2016).

Co-pending U.S. Appl. No. 16/889,624, filed Jun. 1, 2020.

Matsuya et al. Synthesis and evaluation of [11C]RU40555, a selective glucocorticoid receptor antagonist. Journal Of Labelled Compounds And Radiopharmaceuticals 48(9):657-668 (2005).

Volden et al. The influence of glucocorticoid signaling on tumor progression. Brain Behav Immun 30 Suppl:S23-31 (2013).

U.S. Appl. No. 16/065,625 Notice of Allowance dated May 28, 2021.

U.S. Appl. No. 16/065,625 Office Action dated Apr. 30, 2021.

U.S. Appl. No. 16/065,626 Notice of Allowance dated May 19, 2021.

CAS Registry No. 1060698-58-9; STN Entry date Oct. 13, 2008.

Co-pending U.S. Appl. No. 17/039,794, inventors Sun; Daqing et al., filed Sep. 30, 2020.

* cited by examiner

INHIBITORS OF GLUCOCORTICOID RECEPTOR

CROSS-REFERENCE TO RELATED APPLICATIONS

This application is a § 371 U.S. National Stage Entry of International Application No. PCT/US2016/068448, filed Dec. 22, 2016, which claims the benefit of U.S. Provisional Application Ser. No. 62/387,293, filed Dec. 23, 2015, each of which is hereby incorporated by reference in its entirety.

BACKGROUND

A need exists in the art for an effective treatment of cancer, neoplastic disease, and hypercortisolism.

BRIEF SUMMARY OF THE INVENTION

Provided herein are substituted steroidal derivative compounds and pharmaceutical compositions comprising said compounds. The subject compounds and compositions are useful as inhibitors of glucocorticoid receptors (GR). Furthermore, the subject compounds and compositions are useful for the treatment of cancer, such as prostate cancer, breast cancer, lung cancer, and ovarian cancer, and hypercortisolism.

Some embodiments provided herein describe compounds having the structure of Formula (I), or a pharmaceutically acceptable salt, solvate, or prodrug thereof:

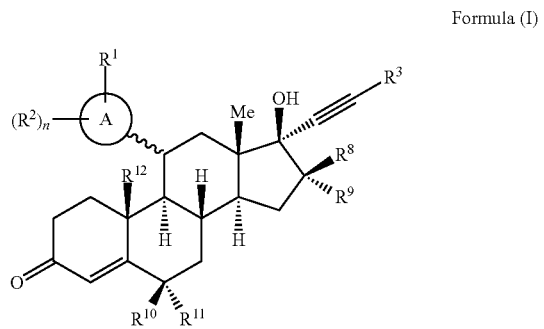

Formula (I)

wherein
ring A is a heteroaryl, aryl, cycloalkyl, or heterocyclyl;
$R^1$ is —H, —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)$OR^6$, —C(O)$NR^4R^5$, —OC(O)$OR^6$, —OC(O)$NR^4R^5$, —S(O)$_2NR^4R^5$, —S(O)$_2R^7$, —S(O)$R^7$, —$SR^7$, —$NR^4S(O)_2NR^4R^5$, —P(O)($OR^6)_2$, —P(O)($R^6)_2$, —CN, —$CO_2H$, or —$NO_2$;
each $R^2$ is independently —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)$R^6$, —C(O)$OR^6$, —C(O)$NR^4R^5$, —OC(O)$OR^6$, —OC(O)$NR^4R^5$, —S(O)$_2NR^4R^5$, —S(O)$_2R^7$, —S(O)$R^7$, —$SR^7$, —$NR^4S(O)_2NR^4R^5$, —CN, —$CO_2H$, or —$NO_2$;
$R^3$ is optionally substituted alkyl, halo, haloalkyl, optionally substituted carbocyclyl, optionally substituted carbocyclylalkyl, optionally substituted heterocyclyl, optionally substituted heterocyclylalkyl, optionally substituted heteroalkyl, optionally substituted aryl, optionally substituted heteroaryl, —Si($R^6)_3$, —$OR^6$, or —S(O)$_2R^7$;
$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2R^7$, —C(O)N($R^{13})_2$, —C(O)$R^6$, or —C(O)$OR^6$;
or $R^4$ and $R^5$ attached to the same N atom are taken together with the N atom to which they are attached to form a substituted or unsubstituted heterocycle;
each $R^6$ is independently optionally substituted alkyl, haloalkyl, optionally substituted carbocyclyl, optionally substituted aryl, optionally substituted heterocyclyl, or optionally substituted heteroaryl;
$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;
$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, OH, S(O)$_2$ $R^7$, C(O)$_2H$, C(O)$R^6$, or C(O)$OR^6$;
or $R^8$ and $R^9$ are taken together with the atom to which they are attached to form a substituted or unsubstituted ring containing 0-2 heteroatoms selected from the group consisting of —O—, —NH—, —$NR^6$—, —S—, and —S(O)$_2$—;
$R^{10}$ and $R^{11}$ are each independently —H, optionally substituted alkyl, halo, haloalkyl, optionally substituted carbocyclyl, optionally substituted carbocyclylalkyl, optionally substituted heteroalkyl, optionally substituted heterocyclyl, optionally substituted heterocyclylalkyl, —OH, —S(O)$_2R^7$, —C(O)$_2H$, —C(O)$R^6$, or —C(O)$OR^6$;
or $R^{10}$ and $R^{11}$ are taken together with the atom to which they are attached to form a substituted or unsubstituted ring containing 0-2 heteroatoms selected from the group consisting of —O—, —NH—, —$NR^6$—, —S—, and —S(O)$_2$—;
$R^{12}$ is hydrogen, optionally substituted alkyl, haloalkyl, hydroxy, halo, optionally substituted carbocyclyl, optionally substituted carbocyclylalkyl, optionally substituted heterocyclyl, optionally substituted heterocyclylalkyl, or optionally substituted heteroalkyl;
each $R^{13}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;
and n is 0, 1, 2, 3, or 4.

In some embodiments, $R^{12}$ is hydrogen, alkyl, haloalkyl, hydroxy, halo, carbocyclyl, or heteroalkyl. In some embodiments, $R^{12}$ is $C_{1-6}$ alkyl or hydrogen. In some embodiments, $R^{12}$ is methyl. In some embodiments, $R^{12}$ is methyl and $R^{10}$ and $R^{11}$ are H. In some embodiments, $R^{12}$ is H. In some embodiments, $R^{10}$, $R^{11}$, and $R^{12}$ are H.

In some embodiments, ring A is monocyclic heteroaryl or monocyclic aryl. In some embodiments, ring A is phenyl, pyridinyl, pyrimidinyl, pyrazinyl, or pyridazinyl. In some embodiments, ring A is bicyclic heteroaryl or bicyclic aryl.

In some embodiments, $R^1$ is —$NR^4R^5$, halo, —$OR^6$, alkyl, fluoroalkyl, carbocyclyl, heteroalkyl, heterocyclyl, —$S(O)_2NR^4R^5$, —$S(O)_2R^7$, or —CN. In some embodiments, each $R^2$ is independently —$NR^4R^5$, halo, —$OR^6$, alkyl, fluoroalkyl, carbocyclyl, heteroalkyl, heterocyclyl, —$S(O)_2NR^4R^5$, or —$S(O)_2R^7$.

In some embodiments, $R^3$ is alkyl, haloalkyl, carbocyclyl, carbocyclylalkyl, heterocyclyl, heterocyclylalkyl, or heteroalkyl. In some embodiments, $R^3$ is optionally substituted aryl or optionally substituted heteroaryl.

In some embodiments, $R^4$ and $R^5$ are each independently —H, $C_{1-6}$ alkyl, or —$S(O)_2R^7$. In some embodiments, $R^4$ and $R^5$ attached to the same N atom are taken together with the N atom to which they are attached to form a substituted or unsubstituted 4-, 5-, or 6-membered ring heterocycle additionally containing 0-3 heteroatoms selected from the group consisting of —O—, —NH—, —$NR^6$—, —S—, and —$S(O)_2$—.

In some embodiments, $R^6$ is alkyl, carbocyclyl, or fluoroalkyl.

In some embodiments, $R^7$ is alkyl, carbocyclyl, optionally substituted aryl, optionally substituted aralkyl, or optionally substituted heterocyclyl.

In some embodiments, $R^8$ and $R^9$ are each independently —H, alkyl, or carbocyclyl. In some embodiments, $R^8$ and $R^9$ are —H.

In some embodiments, $R^{10}$ and $R^{11}$ are each independently —H, $C_{1-6}$ alkyl, halo, $C_{1-6}$ alkoxy, or —OH. In some embodiments, $R^{10}$ and $R^{11}$ are taken together with the atom to which they are attached to form a 3-, 4-, 5-, or 6-membered ring.

In some embodiments, n is 0, 1, or 2.

Some embodiments provided herein describe a pharmaceutical composition comprising a pharmaceutically acceptable excipient and a compound of Formula (I), or a pharmaceutically acceptable salt, solvate, or prodrug thereof.

Also provided herein are methods for treating or preventing cancer in a subject, the method comprising administering to the subject a therapeutically effective amount of a compound having the structure of Formula (I), or a pharmaceutically acceptable salt, solvate, or prodrug thereof. Also provided herein are methods for reducing incidences of cancer recurrence, the method comprising administering to a subject in cancer remission a therapeutically effective amount of a compound having the structure of Formula (I), or a pharmaceutically acceptable salt, solvate, or prodrug thereof. Some embodiments provided herein describe methods for treating a chemo-resistant cancer in a subject, the method comprising administering to the subject a therapeutically effective amount of a compound having the structure of Formula (I), or a pharmaceutically acceptable salt, solvate, or prodrug thereof.

In some embodiments, the cancer is triple negative breast cancer, high grade serous ovarian cancer, castration resistant prostate cancer, or doubly resistant prostate cancer. In some embodiments, the cancer is non-small cell lung cancer. In some embodiments, the methods further comprise administering a second therapeutic agent to the subject. In some embodiments, the methods further comprise administering one or more additional therapeutic agents. In some embodiments, the second or additional therapeutic agent is an androgen receptor signaling inhibitor. In specific embodiments, the androgen receptor signaling inhibitor is 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosteride, or any combinations thereof. In some embodiments, the second or additional therapeutic agent is a chemotherapeutic agent. In other embodiments, the second or additional therapeutic agent is cisplatin, carboplatin, paclitaxel, gemcitabine, doxorubicin, camptothecin, topotecan, or any combinations thereof. In some embodiments, the second or additional therapeutic agent is an immunotherapy agent (e.g., an anti-PD-L1 agent or an anti-PD1 agent). In certain embodiments, the second or additional therapeutic agent is an anti-PD-L1 agent. In certain embodiments, the second or additional therapeutic agent is an anti-PD1 agent.

Other embodiments provided herein describe methods for treating a hypercortisolism disease or disorder in a subject, the method comprising administering to the subject in need thereof a therapeutically effective amount of a compound having the structure of Formula (I), or a pharmaceutically acceptable salt, solvate, or prodrug thereof. In certain embodiments, the hypercortisolism disease or disorder is Cushing's syndrome. In certain embodiments, the hypercortisolism disease or disorder is refractory Cushing's syndrome.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.

"Imino" refers to the =N—H radical.

"Oximo" refers to the =N—OH radical.

"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises one to five carbon atoms (e.g., C$_1$-C$_5$ alkyl). In other embodiments, an alkyl comprises one to four carbon atoms (e.g., C$_1$-C$_4$ alkyl). In other embodiments, an alkyl comprises one to three carbon atoms (e.g., C$_1$-C$_3$ alkyl). In other embodiments, an alkyl comprises one to two carbon atoms (e.g., C$_1$-C$_2$ alkyl). In other embodiments, an alkyl comprises one carbon atom (e.g., C$_1$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). In other embodiments, an alkyl comprises two to five carbon atoms (e.g., C$_2$-C$_5$ alkyl). In other embodiments, an alkyl comprises three to five carbon atoms (e.g., C$_3$-C$_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$, (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O— alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

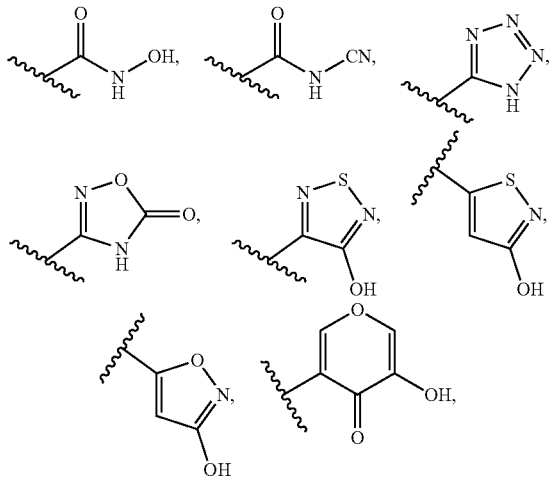

and the like.

"Deuteroalkyl" refers to an alkyl group where 1 or more hydrogen atoms of an alkyl are replaced with deuterium.

"Halo" or "halogen" refers to bromo, chloro, fluoro or iodo substituents.

"Haloalkyl" refers to an alkyl radical, as defined above, that is substituted by one or more halo radicals, as defined above, for example, trifluoromethyl, difluoromethyl, fluoromethyl, 2,2,2-trifluoroethyl, 1-fluoromethyl-2-fluoroethyl, trichloromethyl, dichloromethyl, chloromethyl, 2,2,2-trichloroethyl, 1-chloromethyl-2-chloroethyl, tribromomethyl, dibromomethyl, bromomethyl, 2,2,2-tribromoethyl, 1-bromomethyl-2-bromoethyl, and the like. In some embodiments, the alkyl part of the haloalkyl radical is optionally substituted as defined above for an alkyl group.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$heteroalkyl. Unless stated otherwise specifically in the specification, an heteroalkyl chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7, 8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as R- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. In some embodiments, the compounds described herein contain one or more isotopic variants (e.g., deuterium, tritium, $^{13}$C, and/or $^{14}$C).

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

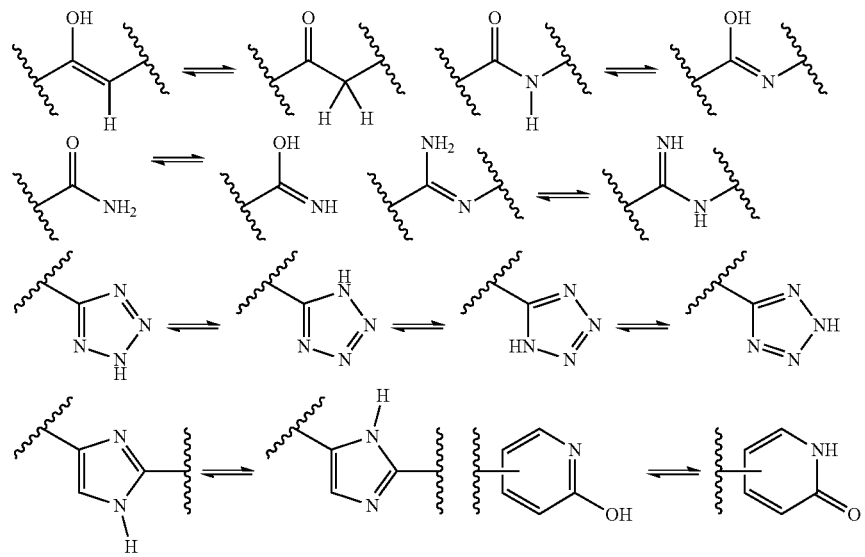

"Pharmaceutically acceptable salt" includes both acid and base addition salts. A pharmaceutically acceptable salt of any one of the substituted steroidal derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included "Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

Abbreviations used herein have their conventional meaning within the chemical and biological arts. The following abbreviations have the indicated meaning throughout: Na$_2$HPO$_4$=disodium phosphate, AcOH=acetic acid, aq.=aqueous, NH4Cl=ammonium chloride, DCM=dichloromethane, DMPU=1,3-dimethyl-3,4,5,6-tetrahydro-2(1H)-pyrimidinone, ESI=electrospray ionization, EtOAc=ethyl acetate, g=gram, h=hour, LCMS=liquid chromatography mass spectrometry, LDA=lithium diisopropylamide, MgSO$_4$=magnesium sulfate, m/s=mass-to-charge ratio, mg=milligram, MeOH=methanol, min=minute, NMR=nuclear magnetic resonance, RT or rt=room temperature, sat.=saturated, NaHCO$_3$=sodium bicarbonate, NaBH$_4$=sodium borohydride, Na$_2$CO$_3$=sodium carbonate, NaCl=sodium chloride, Na$_2$SO$_4$=sodium sulfate, Na$_2$S$_2$O$_3$=sodium thiosulfate, TFA=trifluoroacetic acid, and THF=tetrahydrofuran.

Substituted Steroidal Derivative Compounds

Substituted steroidal derivative compounds are described herein that are GR inhibitors. These compounds, and compositions comprising these compounds, are useful for the treatment of cancer, neoplastic disease, and hypercortisolism diseases and disorders.

Some embodiments provided herein describe a compound having the structure of Formula (I), or a pharmaceutically acceptable salt, solvate, or prodrug thereof:

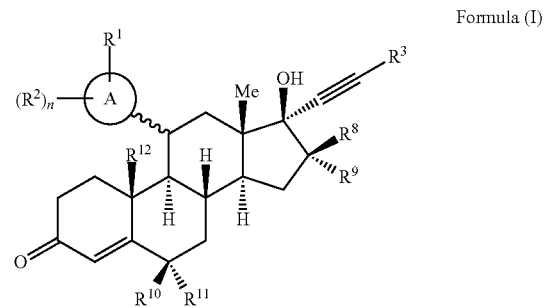

Formula (I)

wherein
ring A is a heteroaryl, aryl, cycloalkyl, or heterocyclyl;
$R^1$ is —H, —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)OR$^6$, —C(O)NR$^4$R$^5$, —OC(O)OR$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —P(O)(OR$^6$)$_2$, —P(O)(R$^6$)$_2$, —CN, —CO$_2$H, or —NO$_2$;
each $R^2$ is independently —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)R$^6$, —C(O)OR$^6$, —C(O)NR$^4$R$^5$, —OC(O)OR$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —CN, —CO$_2$H, or —NO$_2$;
$R^3$ is optionally substituted alkyl, halo, haloalkyl, optionally substituted carbocyclyl, optionally substituted carbocyclylalkyl, optionally substituted heterocyclyl, optionally substituted heterocyclylalkyl, optionally substituted heteroalkyl, optionally substituted aryl, optionally substituted heteroaryl, —Si(R$^6$)$_3$, —OR$^6$, or —S(O)$_2$R$^7$;
$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2$R$^7$, —C(O)N(R$^{13}$)$_2$, —C(O)R$^6$, or —C(O)OR$^6$;
or $R^4$ and $R^5$ attached to the same N atom are taken together with the N atom to which they are attached to form a substituted or unsubstituted heterocycle;
each $R^6$ is independently optionally substituted alkyl, haloalkyl, optionally substituted carbocyclyl, optionally substituted aryl, optionally substituted heterocyclyl, or optionally substituted heteroaryl;
$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;
$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR$^6$, —NR$^4$R$^5$, —C(O)NR$^4$R$^5$, —CN, —S(O)$_2$R$^7$, —C(O)$_2$H, —C(O)R$^6$, or —C(O)OR$^6$;

or $R^8$ and $R^9$ are taken together with the atom to which they are attached to form a substituted or unsubstituted ring containing 0-2 heteroatoms selected from the group consisting of —O—, —NH—, —$NR^6$—, —S—, and —S(O)$_2$—;

$R^{10}$ and $R^{11}$ each independently —H, optionally substituted alkyl, halo, haloalkyl, optionally substituted carbocyclyl, optionally substituted carbocyclylalkyl, optionally substituted heteroalkyl, optionally substituted heterocyclyl, optionally substituted heterocyclylalkyl, —OH, —S(O)$_2$$R^7$, —C(O)$_2$H, —C(O)$R^6$, or —C(O)O$R^6$;

or $R^{10}$ and $R^{11}$ are taken together with the atom to which they are attached to form a substituted or unsubstituted ring containing 0-2 heteroatoms selected from the group consisting of —O—, —NH—, —$NR^6$—, —S—, and —S(O)$_2$—;

$R^{12}$ is hydrogen, optionally substituted alkyl, haloalkyl, deuteroalkyl, hydroxy, halo, optionally substituted carbocyclyl, optionally substituted carbocyclylalkyl, optionally substituted heterocyclyl, optionally substituted heterocyclylalkyl, or optionally substituted heteroalkyl;

each $R^{13}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

and n is 0, 1, 2, 3, or 4.

In some embodiments, ring A is a monocyclic or bicyclic heteroaryl monocyclic or bicyclic aryl, monocyclic cycloalkyl, or monocyclic heterocyclyl;

$R^1$ is —H, —$NR^4R^5$, optionally substituted alkyl$NR^4R^5$, halo, —O$R^6$, —OH, optionally substituted alkyl, haloalkyl, optionally substituted carbocyclyl, optionally substituted heteroalkyl, optionally substituted heterocyclyl, optionally substituted hydroxyalkyl, —C(O)$NR^4R^5$, —S(O)$_2$$NR^4R^5$, —S(O)$_2$$R^7$, —$NR^4$S(O)$_2$$NR^4R^5$, —P(O)(O$R^6$)$_2$, —CN, or —CO$_2$H;

each $R^2$ is independently —$NR^4R^5$, optionally substituted alkyl$NR^4R^5$, halo, —O$R^6$, —OH, optionally substituted alkyl, haloalkyl, optionally substituted carbocyclyl, optionally substituted heteroalkyl, optionally substituted heterocyclyl, optionally substituted hydroxyalkyl, —C(O)$NR^4R^5$, —S(O)$_2$$NR^4R^5$, —S(O)$_2$$R^7$, —$NR^4$S(O)$_2$$NR^4R^5$, —CN, or —CO$_2$H;

$R^3$ is optionally substituted alkyl, halo, haloalkyl, deuteroalkyl, optionally substituted carbocyclyl, optionally substituted carbocyclylalkyl, optionally substituted heterocyclyl, optionally substituted heterocyclylalkyl, optionally substituted heteroalkyl, optionally substituted aryl, optionally substituted heteroaryl, —Si($R^6$)$_3$, —O$R^6$, or —S(O)$_2$$R^7$;

$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2$$R^7$, —C(O)N($R^{13}$)$_2$, —C(O)$R^6$, or —C(O)O$R^6$;

or $R^4$ and $R^5$ attached to the same N atom are taken together with the N atom to which they are attached to form a substituted or unsubstituted 4-, 5-, or 6-membered heterocycle;

$R^6$ is optionally substituted alkyl, haloalkyl, optionally substituted carbocyclyl, optionally substituted aryl, optionally substituted heterocyclyl, or optionally substituted heteroaryl;

$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —S(O)$_2$$R^7$, —C(O)$_2$H, —C(O)$R^6$, or —C(O)O$R^6$;

or $R^8$ and $R^9$ are taken together with the atom to which they are attached to form a substituted or unsubstituted 3-, 4-, 5-, or 6-membered ring containing 0 or 1 heteroatom selected from the group consisting of —O—, —NH—, —$NR^6$—, —S—, and —S(O)$_2$—;

$R^{10}$ and $R^{11}$ are each independently —H, optionally substituted alkyl, halo, haloalkyl, optionally substituted carbocyclyl, optionally substituted heteroalkyl, or —OH;

or $R^{10}$ and $R^{11}$ are taken together with the atom to which they are attached to form a substituted or unsubstituted 3-, 4-, 5-, or 6-membered ring containing 0 or 1 heteroatom selected from the group consisting of —O—, —NH—, —$NR^6$—, —S—, and —S(O)$_2$—;

$R^{12}$ is hydrogen, optionally substituted alkyl, haloalkyl, hydroxy, halo, optionally substituted carbocyclyl, or optionally substituted heteroalkyl;

each $R^{13}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

and n is 0, 1, 2, 3, or 4.

In some embodiments, ring A is aryl or bicyclic heteroaryl;

$R^1$ is —H, —$NR^4R^5$, halo, —O$R^6$, —$C_{1-6}$alkyl, $C_{1-6}$fluoroalkyl, $C_{1-6}$deuteroalkyl, $C_{1-6}$heteroalkyl, $C_{3-6}$carbocyclyl, $C_{3-6}$heterocyclyl, aryl, heteroaryl, —C(O)$NR^4R^5$, —S(O)$_2$$NR^4R^5$, —S(O)$_2$$R^7$, —$NR^4$S(O)$_2$$NR^4R^5$, —P(O)($R^6$)$_2$, —P(O)(O$R^6$)$_2$, or —CN;

each $R^2$ is independently —$NR^4R^5$, halo, —O$R^6$, $C_{1-6}$alkyl, $C_{1-6}$fluoroalkyl, $C_{3-6}$carbocyclyl, $C_{1-6}$deuteroalkyl, $C_{1-6}$heteroalkyl, $C_{3-6}$heterocyclyl, or —CN;

$R^3$ is $C_{1-6}$ alkyl, $C_{1-6}$ fluoroalkyl, $C_{1-6}$heteroalkyl, carbocyclyl, or heterocyclylalkyl;

$R^4$ and $R^5$ are each independently —H, alkyl, fluoroalkyl, carbocyclyl, carbocyclylalkyl, heterocyclyl, alkylheterocyclyl, —S(O)$_2$$R^7$, or —C(O)N($R^{13}$);

or $R^4$ and $R^5$ attached to the same N atom are taken together with the N atom to which they are attached to form a substituted or unsubstituted 4-, 5-, or 6-membered heterocycle;

$R^6$ is alkyl;

$R^7$ is $C_{1-6}$alkyl, $C_{3-6}$carbocyclyl, or phenyl optionally substituted with halo or alkyl;

$R^8$ and $R^9$ are each independently —H;

$R^{10}$ and $R^{11}$ are each independently —H;

$R^{12}$ is hydrogen or alkyl;

each $R^{13}$ is independently hydrogen or $C_{1-6}$ alkyl;

and n is 0, 1, 2, 3, or 4.

In some embodiments, ring A is phenyl or 1,4-benzodioxanyl;

$R^1$ is —$NR^4R^5$, halo, —O$R^6$, alkyl, or fluoroalkyl;

each $R^2$ is independently —$NR^4R^5$, halo, alkyl, carbocyclyl, alkoxy, or —CN;

$R^3$ is $C_{1-6}$ alkyl, $C_{1-6}$ fluoroalkyl, carbocyclyl, deuteroalkyl, or heteroalkyl;

$R^4$ and $R^5$ are each independently —H, alkyl, heteroalkyl, deuteroalkyl, haloalkyl, or —S(O)$_2$$R^7$;

or $R^4$ and $R^5$ attached to the same N atom are taken together with the N atom to which they are attached to form a substituted or unsubstituted 4-, 5-, or 6-membered heterocycle;
$R^6$ is alkyl;
$R^7$ is $C_{1-6}$alkyl, $C_{3-6}$carbocyclyl, or phenyl optionally substituted with halo or alkyl;
$R^8$ and $R^9$ are each independently —H;
$R^{10}$ and $R^{11}$ are each independently —H;
$R^{12}$ is hydrogen or alkyl;
each $R^{13}$ is independently hydrogen or $C_{1-6}$ alkyl;
and n is 0, 1, or 2.

In some embodiments,
ring A is phenyl;
$R^1$ is —$NR^4R^5$, —$OR^6$, or alkyl;
each $R^2$ is independently halo or alkyl;
$R^3$ is $C_{1-6}$ alkyl, $C_{1-6}$ haloalkyl, carbocyclyl, deuteroalkyl, or heteroalkyl;
$R^4$ and $R^5$ are each independently alkyl, heteroalkyl, deuteroalkyl, or haloalkyl;
or $R^4$ and $R^5$ attached to the same N atom are taken together with the N atom to which they are attached to form a substituted or unsubstituted 4-, 5-, or 6-membered heterocycle;
$R^6$ is alkyl;
$R^8$ and $R^9$ are each independently —H;
$R^{10}$ and $R^{11}$ are each independently —H;
$R^{12}$ is hydrogen or methyl;
and n is 0, 1, or 2.

In some embodiments,
ring A is phenyl;
$R^1$ is —$NR^4R^5$, —$OR^6$, or alkyl;
each $R^2$ is independently halo or alkyl;
$R^3$ is $C_{1-6}$ alkyl, $C_{1-6}$ haloalkyl, carbocyclyl, deuteroalkyl, or heteroalkyl;
$R^4$ and $R^5$ are each independently alkyl, heteroalkyl, deuteroalkyl, or haloalkyl;
or $R^4$ and $R^5$ attached to the same N atom are taken together with the N atom to which they are attached to form a substituted or unsubstituted 4-, 5-, or 6-membered heterocycle;
$R^6$ is alkyl;
$R^8$ and $R^9$ are each independently —H;
$R^{10}$ and $R^{11}$ are each independently —H;
$R^{12}$ is hydrogen or methyl;
and n is 0, 1, or 2.

In some embodiments,
ring A is phenyl;
$R^1$ is —$NR^4R^5$, —$OR^6$, or alkyl;
each $R^2$ is independently halo or alkyl;
$R^3$ is $C_{1-6}$ alkyl, $C_{1-6}$ haloalkyl, carbocyclyl, deuteroalkyl, or heteroalkyl;
$R^4$ and $R^5$ are each independently alkyl, heteroalkyl, deuteroalkyl, or haloalkyl;
or $R^4$ and $R^5$ attached to the same N atom are taken together with the N atom to which they are attached to form a substituted or unsubstituted 4-, 5-, or 6-membered heterocycle;
$R^6$ is alkyl;
$R^8$ and $R^9$ are each independently —H;
$R^{10}$ and $R^{11}$ are each independently —H;
$R^{12}$ is hydrogen;
and n is 0, 1, or 2.

In some embodiments,
ring A is phenyl;
$R^1$ is —$NR^4R^5$, —$OR^6$, or alkyl;
each $R^2$ is independently halo or alkyl;
$R^3$ is $C_{1-6}$ alkyl, $C_{1-6}$ haloalkyl, carbocyclyl, deuteroalkyl, or heteroalkyl;
$R^4$ and $R^5$ are each independently alkyl, heteroalkyl, deuteroalkyl, or haloalkyl;
or $R^4$ and $R^5$ attached to the same N atom are taken together with the N atom to which they are attached to form a substituted or unsubstituted 4-, 5-, or 6-membered heterocycle;
$R^6$ is alkyl;
$R^8$ and $R^9$ are each independently —H;
$R^{10}$ and $R^{11}$ are each independently —H;
$R^{12}$ is methyl;
and n is 0, 1, or 2.

In some embodiments,
ring A is 1,4-benzodioxanyl;
$R^3$ is $C_{1-6}$ alkyl, $C_{1-6}$ haloalkyl, carbocyclyl, deuteroalkyl, or heteroalkyl;
$R^8$ and $R^9$ are each independently —H;
$R^{10}$ and $R^{11}$ are each independently —H;
and $R^{12}$ is hydrogen or methyl.

For any and all of the embodiments of Formula (I), substituents are selected from among a subset of the listed alternatives.

In some embodiments, ring A is monocyclic aryl, bicyclic aryl, monocyclic heteroaryl, or bicyclic heteroaryl. In some embodiments, ring A is monocyclic heteroaryl or monocyclic aryl. In some embodiments, ring A is bicyclic heteroaryl or bicyclic aryl. In some embodiments, ring A is N-bound heteroaryl. In some embodiments, ring A is C-bound heteroaryl. In some embodiments, ring A is aryl.

In certain embodiments, ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, $R^1$ is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, ring A is pyrimidinyl, pyridinyl, pyrazinyl, triazinyl, or thiazolyl. In certain embodiments, ring A is C-bound imidazolyl. In certain embodiments, ring A is N-bound imidazolyl. In some embodiments, ring A is pyrimidinyl. In some embodiments, ring A is pyrimidinyl optionally substituted with alkyl or alkoxy. In some embodiments, ring A is pyrazinyl. In some embodiments, ring A is triazinyl. In some embodiments, ring A is thiazolyl.

In some embodiments, ring A is phenyl, pyridinyl, pyrimidinyl, pyrazinyl, or pyridazinyl. In some embodiments, ring A is phenyl.

In some embodiments, ring A is a bicyclic heteroaryl. In certain embodiments, ring A is an optionally substituted 3-benzodioxyxlyl or 1,4-benzodioxanyl. In some embodiments, ring A is an unsubstituted 3-benzodioxyxlyl or 1,4-benzodioxanyl.

In some embodiments, $R^1$ is —H, —$NR^4R^5$, optionally substituted alkyl$NR^4R^5$, halo, optionally substituted alkyl, fluoroalkyl, optionally substituted carbocyclyl, optionally substituted carbocyclylalkyl, optionally substituted heterocyclyl, optionally substituted heterocyclylalkyl, optionally substituted hydroxyalkyl, optionally substituted aryl, optionally substituted heteroaryl, —$C(O)NR^4R^5$, —$OC(O)OR^6$, —$OC(O)NR^4R^5$, —$S(O)_2NR^4R^5$, —$S(O)_2R^7$, —$S(O)R^7$, —SR$^7$, —NR$^4$S(O)$_2$NR$^4$R$^5$, —P(O)(OR$^6$)$_2$, —P(O)(R$^6$)$_2$, —CN, or —NO$_2$. In some embodiments, R$^1$ is —H, —NR$^4$R$^5$, halo, —OR$^6$, optionally substituted alkyl, fluoroalkyl, optionally substituted carbocyclyl, optionally substituted heterocyclyl, optionally substituted aryl, optionally substituted heteroaryl, —C(O)NR$^4$R$^5$, —S(O)$_2$NR$^4$R$^5$, —S(O)$_2$R$^7$, —NR$^4$S(O)$_2$NR$^4$R$^5$, —P(O)(R$^6$)$_2$, —P(O)(OR$^6$)$_2$, or —CN. In some embodiments, R$^1$ is —H, —NR$^4$R$^5$, optionally substituted alkylNR$^4$R$^5$, halo, —OR$^6$, optionally substituted alkyl, fluoroalkyl, optionally substituted carbocyclyl, optionally substituted heteroalkyl, optionally substituted heterocyclyl, —C(O)R$^6$, —C(O)NR$^4$R$^5$, —S(O)$_2$NR$^4$R$^5$, —S(O)$_2$R$^7$, —NR$^4$S(O)$_2$NR$^4$R$^5$, —CN, or —CO$_2$H. In some embodiments, R$^1$ is —NR$^4$R$^5$, halo, —OR$^6$, alkyl, fluoroalkyl, carbocyclyl, heteroalkyl, heterocyclyl, —S(O)$_2$NR$^4$R$^5$, —S(O)$_2$R$^7$, —NR$^4$S(O)$_2$NR$^4$R$^5$, or —CN. In some embodiments, R$^1$ is —NR$^4$R$^5$, halo, —OR$^6$, C$_{1-6}$fluoroalkyl, C$_{3-6}$carbocyclyl, C$_{3-6}$heterocyclyl, aryl, heteroaryl, —C(O)NR$^4$R$^5$, —S(O)$_2$NR$^4$R$^5$, —S(O)$_2$R$^7$, —NR$^4$S(O)$_2$NR$^4$R$^5$, —P(O)(R$^6$)$_2$, —P(O)(OR$^6$)$_2$, or —CN. In some embodiments, R$^1$ is —NR$^4$R$^5$, halo, —OR$^6$, —S(O)$_2$NR$^4$R$^5$, —P(O)(R$^6$)$_2$, or —P(O)(OR$^6$)$_2$. In certain embodiments, R$^1$ is —NR$^4$R$^5$, halo, —OR$^6$, alkyl, or fluoroalkyl. In certain embodiments, R$^1$ is halo, —OR$^6$, or alkyl. In other embodiments, R$^1$ is —NMe$_2$, —NHMe, —NH$_2$, methyl, ethyl, propyl, iso-propyl, butyl, iso-butyl, sec-butyl, tert-butyl, methoxy, ethoxy, propoxy, iso-propoxy, morpholino, or pyrrolidino. In certain embodiments, R$^1$ is C$_{1-6}$alkyl, fluoroalkyl, C$_{3-6}$carbocyclyl, or C$_{3-6}$heterocyclyl. In some embodiments, R$^1$ is —H. In some embodiments, R$^1$ is —NR$^4$R$^5$. In some embodiments, R$^1$ is —NMe$_2$. In some embodiments, R$^1$ is —NHMe. In some embodiments, R$^1$ is —NH$_2$. In some embodiments, R$^1$ is —NMeEt. In some embodiments, R$^1$ is —NEt$_2$. In some embodiments, R$^1$ is halo. In some embodiments, R$^1$ is fluoro. In some embodiments, R$^1$ is chloro. In some embodiments, R$^1$ is bromo. In some embodiments, R$^1$ is C$_{1-6}$alkyl. In some embodiments, R$^1$ is methyl. In some embodiments, R$^1$ is ethyl. In some embodiments, R$^1$ is propyl. In some embodiments, R$^1$ is iso-propyl. In some embodiments, R$^1$ is carbocyclyl. In some embodiments, R$^1$ is cyclopropyl. In some embodiments, R$^1$ is cyclobutyl. In some embodiments, R$^1$ is cyclopentyl. In some embodiments, R$^1$ is cyclohexyl. In some embodiments, R$^1$ is —OR$^6$. In some embodiments, R$^1$ is methoxy. In some embodiments, R$^a$ is ethoxy. In some embodiments, R$^1$ is propoxy. In some embodiments, R$^1$ is iso-propoxy. In some embodiments, R$^1$ is heterocyclyl. In some embodiments, R$^1$ is azetadino, morpholino, thiomorpholino, piperidino, piperazino, or pyrrolidino. In some embodiments, R$^1$ is morpholino. In some embodiments, R$^1$ is pyrrolidino. In some embodiments, R$^1$ is azetadino.

In other embodiments, R$^1$ is optionally substituted monocyclic aryl, optionally substituted bicyclic aryl, optionally substituted monocyclic heteroaryl, or optionally substituted bicyclic heteroaryl. In certain embodiments, R$^1$ is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, R$^1$ is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, R$^1$ is pyrimidinyl, pyridinyl, pyrazinyl, triazinyl, or thiazolyl. In certain embodiments, R$^1$ is C-bound imidazolyl. In certain embodiments, R$^1$ is N-bound imidazolyl. In some embodiments, R$^1$ is pyrimidinyl. In some embodiments, R$^1$ is pyrimidinyl optionally substituted with alkyl or alkoxy. In some embodiments, R$^1$ is pyrazinyl. In some embodiments, R$^1$ is triazinyl. In some embodiments, R$^1$ is thiazolyl.

In certain embodiments, R$^1$ is optionally substituted with halo, alkyl, hydroxy, alkoxy, or fluoroalkyl. In certain embodiments, R$^1$ is optionally substituted with halo, alkyl, or alkoxy. In some embodiments, R$^1$ is optionally substituted with fluoro or C$_{1-6}$alkyl. In some embodiments, R$^1$ is optionally substituted with fluoro or methyl. In some embodiments, R$^1$ is optionally substituted with methyl or methoxy.

In some embodiments, each R$^2$ is independently —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocylylalkyl, optionally substituted hydroxyalkyl, —C(O)R$^6$, —C(O)NR$^4$R$^5$, —S(O)$_2$NR$^4$R$^5$, —S(O)$_2$R$^7$, —NR$^4$S(O)$_2$NR$^4$R$^5$, or —CN. In some embodiments, each R$^2$ is independently —NR$^4$R$^5$, alkylNR$^4$R$^5$, halo, —OR$^6$, —OH, alkyl, haloalkyl, carbocyclyl, carbocyclylalkyl, heteroalkyl, heterocyclyl, heterocyclylalkyl, hydroxyalkyl, —C(O)R$^6$, —C(O)NR$^4$R$^5$, —S(O)$_2$NR$^4$R$^5$, —S(O)$_2$R$^7$, —NR$^4$S(O)$_2$NR$^4$R$^5$, or —CN. In some embodiments, —NR$^4$R$^5$, halo, —OR$^6$, optionally substituted alkyl, fluoroalkyl, optionally substituted carbocyclyl, optionally substituted heteroalkyl, optionally substituted heterocyclyl, —C(O)NR$^4$R$^5$, —S(O)$_2$NR$^4$R$^5$, —S(O)$_2$R$^7$, —NR$^4$S(O)$_2$NR$^4$R$^5$, —CN, or —CO$_2$H. In certain embodiments, each R$^2$ is independently —NR$^4$R$^5$, halo, —OR$^6$, —OH, optionally substituted alkyl, fluoroalkyl, optionally substituted carbocyclyl, optionally substituted heteroalkyl, optionally substituted heterocyclyl, optionally substituted hydroxyalkyl, —S(O)$_2$NR$^4$R$^5$, —S(O)$_2$R$^7$, —NR$^4$S(O)$_2$NR$^4$R$^5$, or —CN. In some embodiments, each R$^2$ is independently —NR$^4$R$^5$, halo, —OR$^6$, alkyl, fluoroalkyl, carbocyclyl, heteroalkyl, heterocyclyl, —S(O)$_2$NR$^4$R$^5$, —NR$^4$S(O)$_2$NR$^4$R$^5$, or —S(O)$_2$R$^7$. In some embodiments, each R$^2$ is independently —NR$^4$R$^5$, C$_{1-6}$alkylNR$^4$R$^5$, halo, —OR$^6$, —OH, C$_{1-6}$alkyl, C$_{1-6}$fluoroalkyl, C$_{3-6}$carbocyclyl, C$_{1-6}$alkylC$_{3-6}$carbocyclyl, C$_{1-6}$heteroalkyl, C$_{3-6}$heterocyclyl, C$_{1-6}$alkylC$_{3-6}$heterocyclyl, C$_{1-6}$hydroxyalkyl, or —CN. In some embodiments, each R$^2$ is independently —C(O)R$^6$, —C(O)NR$^4$R$^5$, —S(O)$_2$NR$^4$R$^5$, —S(O)$_2$R$^7$, or —CN. In some embodiments, each R$^2$ is independently —NR$^4$R$^5$, halo, —OR$^6$, C$_{1-6}$alkyl, C$_{1-6}$fluoroalkyl, C$_{3-6}$carbocyclyl, C$_{1-6}$heteroalkyl, C$_{3-6}$heterocyclyl, or —CN. In some embodiments, each R$^2$ is independently —NR$^4$R$^5$, halo, alkyl, carbocyclyl, alkoxy, or —CN. In some embodiments, each R$^2$ is independently —NR$^4$R$^5$, halo, alkyl, or alkoxy. In some embodiments, each R$^2$ is independently methyl, methoxy, ethyl, propyl, iso-propyl, cyclopropyl, fluoro, chloro, or —NMe$_2$. In some embodiments, each R$^2$ is independently methyl, methoxy, iso-propyl, cyclopropyl, fluoro, chloro, or —NMe$_2$. In some embodiments, R$^2$ is methoxy. In some embodiments, R$^2$ is methyl. In some embodiments R$^2$ is ethyl. In some embodiments, R$^2$ is iso-propyl. In some embodiments, R$^2$ is propyl. In some embodiments, R$^2$ is cyclopropyl. In some embodiments, R$^2$ is cyclobutyl. In some embodiments, R$^2$ is fluoro. In some embodiments, R$^2$ is chloro. In some embodiments, $R^2$ is —NMe$_2$. In some embodiments, $R^2$ is —NH$_2$. In some embodiments, $R^2$ is —NHMe. In some embodiments, $R^2$ is —NMeEt.

In certain embodiments, each $R^2$ is independently optionally substituted with halo, alkyl, hydroxy, alkoxy, or fluoroalkyl. In some embodiments, each $R^2$ is independently optionally substituted with fluoro or $C_{1-6}$alkyl. In some embodiments, each $R^2$ is independently optionally substituted with fluoro or methyl.

In some embodiments, $R^3$ is alkyl, halo, haloalkyl, deuteroalkyl, carbocyclyl, carbocyclylalkyl, heterocyclyl, heterocyclylalkyl, aryl, heteroaryl, —Si(R$^6$)$_3$, —OR$^6$, or —S(O)$_2$R$^7$. In some embodiments, $R^3$ is alkyl, halo, haloalkyl, carbocyclyl, carbocyclylalkyl, heterocyclyl, heterocyclylalkyl, or heteroalkyl. In some embodiments, $R^3$ is optionally substituted $C_{1-10}$ alkyl, halo, haloalkyl, deuteroalkyl, carbocyclyl, optionally substituted aryl, or optionally substituted heteroaryl, wherein $R^3$ is optionally substituted with halo, alkyl, alkoxy, hydroxy, —NR$^4$R$^5$, or —S(O)$_2$R$^7$. In some embodiments, $R^3$ is $C_{1-6}$ alkyl, $C_{1-6}$ haloalkyl, $C_{1-6}$ deuteroalkyl, $C_{3-6}$ carbocyclyl, $C_{3-6}$ carbocyclylC$_{1-6}$ alkyl, $C_{3-6}$heterocyclyl, $C_{3-6}$ heterocyclylC$_{1-6}$ alkyl. In some embodiments, $R^3$ is alkyl, haloalkyl, carbocyclyl, carbocyclylalkyl, heterocyclyl, heterocyclylalkyl, or heteroalkyl. In some embodiments, $R^3$ is $C_{1-6}$ alkyl, $C_{1-6}$ fluoroalkyl, carbocyclyl, or heterocyclylalkyl. In certain embodiments, $R^3$ is $C_{3-8}$ alkyl or $C_{1-6}$ fluoroalkyl. In some embodiments, $R^3$ is $C_{1-6}$ alkyl. In some embodiments, $R^3$ is $C_{1-8}$ alkyl. In some embodiments, $R^3$ is $C_{2-8}$ alkyl. In some embodiments, $R^3$ is $C_{3-6}$ alkyl. In some embodiments, $R^3$ is methyl. In some embodiments, $R^3$ is ethyl. In some embodiments, $R^3$ is propyl. In some embodiments, $R^3$ is i-propyl. In some embodiments, $R^3$ is t-butyl. In some embodiments, $R^3$ is butyl. In some embodiments, $R^3$ is isobutyl. In some embodiments, $R^3$ is sec-butyl. In some embodiments, $R^3$ is carbocyclyl. In some embodiments, $R^3$ is cyclopropyl. In some embodiments, $R^3$ is cyclobutyl. In some embodiments, $R^3$ is cyclopentyl. In some embodiments, $R^3$ is cyclohexyl. In some embodiments, $R^3$ is halo. In some embodiments, $R^3$ is fluoro. In some embodiments, $R^3$ is chloro. In some embodiments, $R^3$ is bromo. In some embodiments, $R^3$ is trifluoromethyl. In some embodiments, $R^3$ is hydroxyalkyl. In some embodiments, $R^3$ is deuteromethyl. In some embodiments, $R^3$ is —Si(R$^6$)$_3$. In some embodiments, $R^3$ is —Si(Me)$_3$. In some embodiments, $R^3$ is —Si(Ph)$_3$. In some embodiments, $R^3$ is —OR$^6$. In some embodiments, $R^3$ is —S(O)$_2$R$^7$.

In other embodiments, $R^3$ is optionally substituted aryl or optionally substituted heteroaryl. In certain specific embodiments, $R^3$ is phenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, $R^3$ is phenyl optionally substituted with halo, alkyl, alkoxy, hydroxy, —NR$^4$R$^5$, or —S(O)$_2$R$^7$. In some embodiments, $R^3$ is pyridinyl optionally substituted with halo, alkyl, alkoxy, hydroxy, —NR$^4$R$^5$, or —S(O)$_2$R$^7$. In some embodiments, $R^3$ is phenyl. In some embodiments, $R^3$ is pyridinyl.

In certain embodiments, $R^3$ is optionally substituted with halo, alkyl, hydroxy, alkoxy, —NR$^4$R$^5$, —S(O)$_2$R$^7$ or fluoroalkyl. In some embodiments, $R^3$ is optionally substituted with chloro, fluoro, methyl, ethyl, propyl, iso-propyl, butyl, iso-butyl, sec-butyl, tert-butyl, hydroxy, methoxy, ethoxy, propoxy, iso-propoxy, dimethylamino, diethylamino, methylamino, amino, —S(O)$_2$Me, or trifluoromethyl. In certain embodiments, $R^3$ is optionally substituted with chloro, fluoro, methyl, hydroxy, methoxy, dimethylamino, —S(O)$_2$Me, or trifluoromethyl.

In some embodiments, $R^4$ and $R^5$ are each independently —H, optionally substituted alkyl, fluoroalkyl, optionally substituted carbocyclyl, optionally substituted carbocyclylalkyl, optionally substituted heterocyclyl, optionally substituted heterocyclylalkyl, —S(O)$_2$R$^7$, or —C(O)N(R$^{13}$)$_2$. In some embodiments, $R^4$ and $R^5$ are each independently —H, $C_{1-6}$ alkyl, $C_{1-6}$ fluoroalkyl, $C_{3-6}$ carbocyclyl, $C_{1-6}$ carbocyclylalkyl, $C_{2-6}$ heterocyclyl, $C_{1-6}$ alkylC$_{3-6}$heterocyclyl, —S(O)$_2$R$^7$, or —C(O)N(R$^{13}$)$_2$. In some embodiments, $R^4$ and $R^5$ are each independently —H, $C_{1-6}$alkyl, $C_{1-6}$fluoroalkyl, $C_{3-6}$carbocyclyl, $C_{3-5}$heterocyclyl, or —S(O)$_2$R$^7$. In some embodiments, $R^4$ and $R^5$ are each independently —H, $C_{1-6}$alkyl, or —S(O)$_2$R$^7$. In some embodiments, $R^4$ and $R^5$ are each independently —H, methyl, ethyl, propyl, isopropyl, butyl, sec-butyl, iso-butyl, tert-butyl, or —S(O)$_2$R$^7$. In some embodiments, $R^4$ and $R^5$ are —H. In some embodiments, $R^4$ and $R^5$ are methyl. In some embodiments, $R^4$ and $R^5$ are each independently —H or —C(O)N(R$^{13}$)$_2$.

In other embodiments, $R^4$ and $R^5$ attached to the same N atom are taken together with the N atom to which they are attached to form a substituted or unsubstituted 4-, 5-, or 6-membered ring heterocycle additionally containing 0-3 heteroatoms selected from —O—, —NH—, —NR$^6$—, —S—, and —S(O)$_2$—. In some embodiments, $R^4$ and $R^5$ attached to the same N atom are taken together with the N atom to which they are attached to form a 4-, 5- or 6-membered heterocycle additionally containing 0 or 1 oxygen heteroatom. In other embodiments, $R^4$ and $R^5$ attached to the same N atom are taken together with the N atom to which they are attached to form a substituted or unsubstituted 4-, 5-, or 6-membered ring heterocycle additionally containing 1 heteroatoms selected from —O—, —NH—, —NR$^6$—, —S—, and —S(O)$_2$—. In other embodiments, $R^4$ and $R^5$ attached to the same N atom are taken together with the N atom to which they are attached to form a 4-, 5-, or 6-membered ring heterocycle additionally containing 1 oxygen heteroatom. In other embodiments, $R^4$ and $R^5$ attached to the same N atom are taken together with the N atom to which they are attached to form a 4-, 5-, or 6-membered ring. In some embodiments, the 4-, 5-, or 6-membered ring is

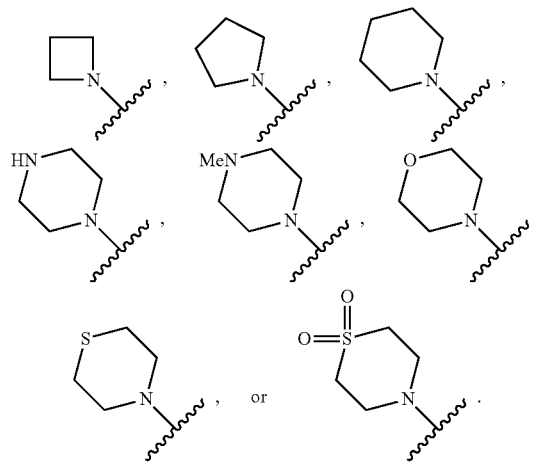

In certain embodiments, $R^4$ and $R^5$ are each independently optionally substituted with halo, alkyl, hydroxy, alkoxy, or fluoroalkyl. In some embodiments, $R^4$ and $R^5$ are each independently optionally substituted with fluoro or $C_{1-6}$alkyl. In some embodiments, $R^4$ and $R^5$ are each independently optionally substituted with fluoro or methyl.

In some embodiments, $R^6$ is optionally substituted alkyl, fluoroalkyl, optionally substituted aryl, optionally substituted carbocyclyl, or optionally substituted heterocyclyl. In some embodiments, $R^6$ is optionally substituted alkyl, fluoroalkyl, optionally substituted carbocyclyl, or optionally substituted heterocyclyl. In some embodiments, $R^6$ is alkyl, aryl, carbocyclyl, or heterocyclyl. In some embodiments, $R^6$ is alkyl, carbocyclyl, or heterocyclyl. In some embodiments, $R^6$ is alkyl, carbocyclyl, or fluoroalkyl. In some embodiments, $R^6$ is $C_{1-6}$alkyl, $C_{1-6}$fluoroalkyl, $C_{3-6}$carbocyclyl, or $C_{3-6}$heterocyclyl. In certain embodiments, $R^6$ is $C_{1-6}$alkyl. In certain embodiments, $R^6$ is methyl, ethyl, propyl, iso-propyl, butyl, sec-butyl, iso-butyl, or tert-butyl. In some embodiments, $R^6$ is optionally substituted phenyl.

In some embodiments, $R^7$ is alkyl, carbocyclyl, optionally substituted aryl, optionally substituted aralkyl, or optionally substituted heterocyclyl. In some embodiments, $R^7$ is $C_{1-6}$alkyl, $C_{3-6}$carbocyclyl, or aryl optionally substituted with halo or alkyl. In some embodiments, $R^7$ is $C_{1-6}$alkyl, $C_{3-6}$carbocyclyl, or phenyl optionally substituted with halo or alkyl. In some embodiments, $R^7$ is optionally substituted benzyl. In some embodiments, $R^7$ is $C_{3-6}$carbocyclyl. In some embodiments, $R^7$ is phenyl. In some embodiments, $R^7$ is phenyl substituted with 1-4 $C_{1-6}$alkyl or fluoro substituents. In some embodiments, $R^7$ is phenyl substituted with a $C_{1-6}$alkyl or fluoro substituent. In some embodiments, $R^7$ is alkyl, carbocyclyl, aralkyl, or heterocyclyl.

In certain embodiments, $R^7$ is optionally substituted with halo, alkyl, hydroxy, alkoxy, or fluoroalkyl. In some embodiments, $R^7$ is optionally substituted with fluoro or $C_{1-6}$alkyl. In some embodiments, $R^7$ is optionally substituted with fluoro or methyl.

In some embodiments, $R^8$ and $R^9$ are each independently —H, $C_{1-6}$alkyl, $C_{1-6}$haloalkyl, halo, $C_{3-6}$carbocyclyl, $C_{1-6}$alkyl$C_{3-6}$carbocyclyl, $C_{1-6}$heterocyclyl, $C_{3-6}$heterocyclyl, $C_{1-6}$alkyl$C_{3-6}$heterocyclyl, —OH, —O$R^6$, —N$R^4R^5$, —C(O)N$R^4R^5$, —CN, —S(O)$_2R^7$, —C(O)$_2$H, —C(O)$R^6$, or —C(O)O$R^6$ or $R^8$ and $R^9$ are taken together with the atom to which they are attached to form a ring containing 0-2 heteroatoms selected from the group consisting of —O—, —NH—, —N$R^6$—, —S—, and —S(O)$_2$—. In some embodiments, $R^8$ and $R^9$ are each independently —H, $C_{1-6}$alkyl, halo, $C_{3-6}$carbocyclyl, methoxy, ethoxy, propoxy, iso-propoxy, —NH$_2$, —NMe$_2$, —NHMe, —NEt$_2$, —C(O)NH$_2$, —C(O)NMe$_2$, —C(O)NHMe, or —CN. In some embodiments, $R^8$ and $R^9$ are each independently —H, $C_{1-6}$alkyl, $C_{1-6}$fluoroalkyl, halo, or $C_{3-6}$carbocyclyl. In some embodiments, $R^8$ and $R^9$ are each independently —H, $C_{1-6}$alkyl, or $C_{3-6}$carbocyclyl. In some embodiments, $R^8$ is —H and $R^9$ is $C_{1-6}$alkyl, $C_{1-6}$fluoroalkyl, or $C_{3-6}$carbocyclyl. In some embodiments, $R^8$ is —H and $R^9$ is alkyl. In some embodiments, $R^8$ is $C_{1-6}$alkyl, $C_{1-6}$fluoroalkyl, or $C_{3-6}$carbocyclyl and $R^9$ is —H. In some embodiments, $R^8$ is methyl and $R^9$ is —H. In some embodiments, $R^8$ and $R^9$ are —H. In some embodiments, $R^8$ and $R^9$ are $C_{1-6}$alkyl. In some embodiments, $R^8$ and $R^9$ are methyl.

In other embodiments, $R^8$ and $R^9$ are taken together with the atom to which they are attached to form a 3-, 4-, 5-, or 6-membered ring containing 0-2 heteroatoms selected from the group consisting of —O—, —NH—, —N$R^6$—, —S—, and —S(O)$_2$—. In some embodiments, $R^8$ and $R^9$ are taken together with the atom to which they are attached to form a 3-, 4-, 5-, or 6-membered carbocyclic ring.

In some embodiments, $R^{10}$ and $R^{11}$ are each independently —H, alkyl, halo, haloalkyl, carbocyclyl, heteroalkyl, or —OH, wherein at least one of $R^{10}$ or $R^{11}$ is not H. In other embodiments, $R^{10}$ and $R^{11}$ are each independently —H, $C_{1-6}$alkyl, halo, $C_{1-6}$ alkoxy, or —OH, wherein at least one of $R^{10}$ or $R^{11}$ is not H. In certain embodiments, $R^{10}$ and $R^{11}$ are each independently —H or $C_{1-6}$ alkyl, wherein at least one of $R^{10}$ or $R^{11}$ is not H. In certain embodiments, $R^{10}$ and $R^{11}$ are each independently —H, fluoro, chloro, methyl, ethyl, propyl, iso-propyl, butyl, iso-butyl, sec-butyl, or tert-butyl, wherein at least one of $R^{10}$ or $R^{11}$ is not H. In certain embodiments, $R^{10}$ and $R^{11}$ are each independently —H, fluoro, or methyl, wherein at least one of $R^{10}$ or $R^{11}$ is not H. In certain embodiments, $R^{10}$ and $R^{11}$ are each independently —H or methyl, wherein at least one of $R^{10}$ or $R^{11}$ is not H. In certain embodiments, $R^{10}$ and $R^{11}$ are each independently —H or fluoro, wherein at least one of $R^{10}$ or $R^{11}$ is not H. In certain embodiments, $R^{10}$ and $R^{11}$ are each independently —H or methoxy, wherein at least one of $R^{10}$ or $R^{11}$ is not H. In certain embodiments, $R^{10}$ and $R^{11}$ are each independently —H or —OH, wherein at least one of $R^{10}$ or $R^{11}$ is not H. In certain embodiments, $R^{10}$ and $R^{11}$ are each independently —H or fluoro, wherein at least one of $R^{10}$ or $R^{11}$ is not H. In certain embodiments, $R^{10}$ and $R^{11}$ are each independently —H or chloro, wherein at least one of $R^{10}$ or $R^{11}$ is not H.

In some embodiments, $R^{10}$ and $R^{11}$ are methyl. In some embodiments, $R^{10}$ and $R^{11}$ are ethyl. In some embodiments, $R^{10}$ and $R^{11}$ are propyl. In some embodiments, $R^{10}$ and $R^{11}$ are fluoro. In some embodiments, $R^{10}$ and $R^{11}$ are chloro. In some embodiments, $R^{10}$ and $R^{11}$ are bromo. In some embodiments, $R^{10}$ and $R^{11}$ are methoxy. In some embodiments, $R^{10}$ and $R^{11}$ are ethoxy. In some embodiments, $R^{10}$ and $R^{11}$ are —OH.

In some embodiments, $R^{10}$ and $R^{11}$ are taken together with the atom to which they are attached to form a 3-, 4-, 5-, or 6-membered ring. In some embodiments, $R^{10}$ and $R^{11}$ are taken together with the atom to which they are attached to form a cyclopropyl, cyclobutyl, cyclopentyl, or cyclohexyl. In some embodiments, $R^{10}$ and $R^{11}$ are taken together with the atom to which they are attached to form a cyclopropyl.

In certain embodiments, $R^{10}$ and $R^{11}$ are optionally substituted with halo, alkyl, hydroxy, alkoxy, or fluoroalkyl. In some embodiments, $R^{10}$ and $R^{11}$ are optionally substituted with fluoro or $C_{1-6}$alkyl. In some embodiments, $R^{10}$ and $R^{11}$ are optionally substituted with fluoro or methyl.

In some embodiments, $R^{12}$ is hydrogen, $C_{1-6}$ alkyl, $C_{1-6}$ haloalkyl, $C_{1-6}$ deuteroalkyl, $C_{3-6}$ carbocyclyl, $C_{3-6}$ carbocyclyl$C_{1-6}$ alkyl, $C_{3-6}$heterocyclyl, $C_{3-6}$ heterocyclyl$C_{1-6}$ alkyl. In some embodiments, $R^{12}$ is hydrogen, alkyl, haloalkyl, hydroxy, halo, carbocyclyl, or heteroalkyl. In some embodiments, $R^{12}$ is hydrogen, $C_{1-6}$ alkyl, $C_{1-6}$ fluoroalkyl, carbocyclyl, or heterocyclylalkyl. In certain embodiments, $R^{12}$ is $C_{1-6}$ alkyl or $C_{1-6}$ fluoroalkyl. In some embodiments, $R^{12}$ is $C_{1-6}$ alkyl, $C_{1-6}$haloalkyl, $C_{1-6}$deuteroalkyl, $C_{3-6}$ carbocyclyl, $C_{3-6}$ carbocyclyl$C_{1-6}$ alkyl, $C_{3-6}$heterocyclyl, $C_{3-6}$ heterocyclyl$C_{1-6}$ alkyl. In some embodiments, $R^{12}$ is alkyl, haloalkyl, hydroxy, halo, carbocyclyl, or heteroalkyl. In some embodiments, $R^{12}$ is $C_{1-6}$ alkyl, $C_{1-6}$ fluoroalkyl, carbocyclyl, or heterocyclylalkyl. In certain embodiments, $R^{12}$ is $C_{1-6}$ alkyl or $C_{1-6}$ fluoroalkyl. In certain embodiments, $R^{12}$ is hydrogen. In some embodiments, $R^{12}$ is $C_{1-6}$ alkyl. In some embodiments, $R^{12}$ is $C_{1-3}$ alkyl. In some embodiments, $R^{12}$ is $C_{2-8}$ alkyl. In some embodiments, $R^{12}$ is $C_{3-6}$ alkyl. In some embodiments, $R^{12}$ is methyl. In some embodiments, $R^{12}$ is ethyl. In some embodiments, $R^{12}$ is propyl. In some embodiments, $R^{12}$ is i-propyl. In some embodiments, $R^{12}$ is t-butyl. In some embodiments, $R^{12}$ is butyl. In some embodiments, $R^{12}$ is isobutyl. In some embodiments, $R^{12}$ is sec-butyl. In some embodiments, $R^{12}$ is carbocyclyl. In some embodiments, $R^{12}$ is cyclopropyl. In some embodiments, $R^{12}$ is cyclobutyl. In some embodiments, $R^{12}$ is cyclopentyl. In some embodiments, $R^{12}$ is cyclohexyl. In some embodiments, $R^{12}$ is trifluoromethyl. In some embodiments, $R^{12}$ is hydroxyalkyl. In some embodiments, $R^{12}$ is deuteromethyl.

In certain embodiments, $R^{12}$ is optionally substituted with halo, alkyl, hydroxy, alkoxy, or fluoroalkyl. In some embodiments, $R^{12}$ is optionally substituted with fluoro or $C_{1-6}$alkyl. In some embodiments, $R^{12}$ is optionally substituted with fluoro or methyl.

In some embodiments, each $R^{13}$ is independently hydrogen, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl. In some embodiments, each $R^{13}$ is independently hydrogen, optionally substituted alkyl, optionally substituted carbocyclyl, optionally substituted heteroalkyl, or optionally substituted aryl. In some embodiments, each $R^{13}$ is independently optionally substituted alkyl, optionally substituted carbocyclyl, optionally substituted heteroalkyl, optionally substituted aryl, or heteroaryl. In some embodiments, each $R^{13}$ is independently alkyl or aryl. In some embodiments, each $R^{13}$ is independently hydrogen or $C_{1-6}$ alkyl. In some embodiments, each $R^{13}$ is independently hydrogen, methyl, ethyl, propyl, iso-propyl, butyl, iso-butyl, sec-butyl, tert-butyl, pentyl or hexyl. In some embodiments, each $R^{13}$ is independently hydrogen, methyl, ethyl, propyl, iso-propyl, butyl, or tert-butyl. In some embodiments, each $R^{13}$ is independently hydrogen or methyl. In some embodiments, $R^{13}$ is H. In other embodiments, $R^{13}$ is alkyl. In other embodiments, $R^{13}$ is aryl.

In some embodiments, n is 0, 1, or 2. In some embodiments, n is 1 or 2. In some embodiments, n is 3 or 4. In some embodiments, n is 0. In some embodiments, n is 1. In some embodiments, n is 2. In some embodiments, n is 3.

In some embodiments, compounds described herein have the following structure of Formula (Ia):

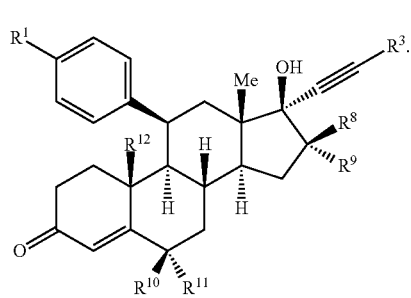

Formula (Ia)

In some embodiments, compounds described herein have the following structure of Formula (Ib):

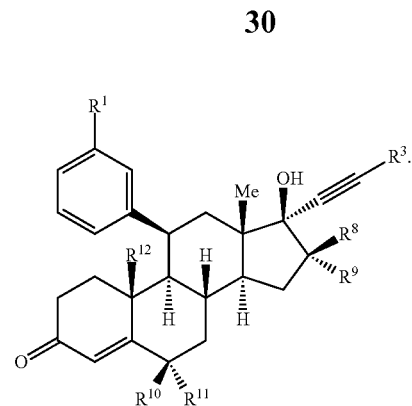

Formula (Ib)

In some embodiments, compounds described herein have the following structure of Formula (Ic):

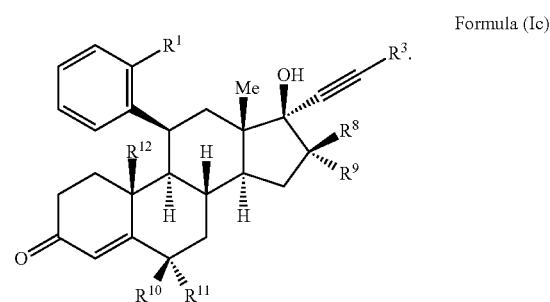

Formula (Ic)

In some embodiments, compounds described herein have the following structure of Formula (Id):

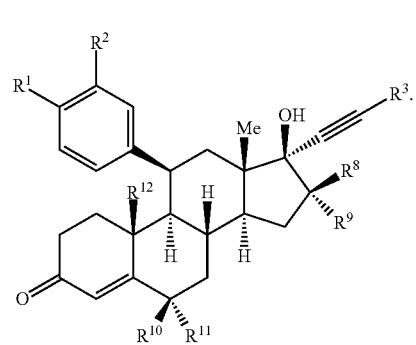

Formula (Id)

In some embodiments, compounds described herein have the following structure of Formula (Ie):

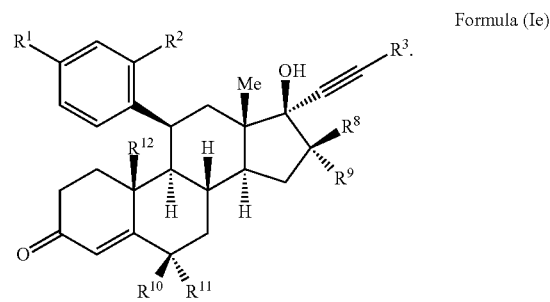

Formula (Ie)

In some embodiments, compounds described herein have the following structure of Formula (If):

Formula (If)

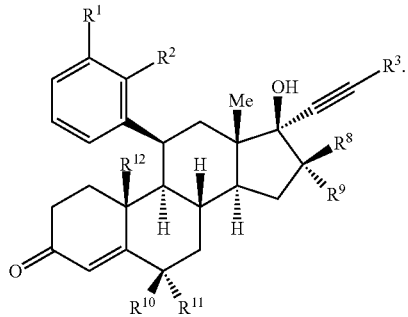

In some embodiments, compounds described herein have the following structure of Formula (Ig):

Formula (Ig)

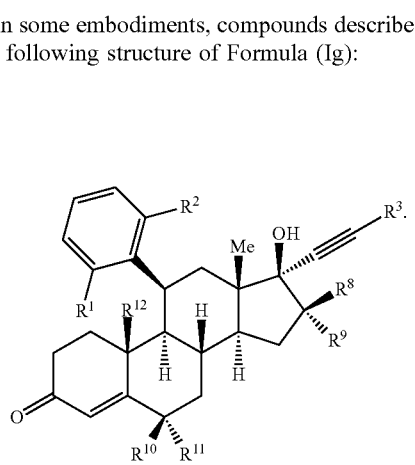

In some embodiments, compounds described herein have the following structure of Formula (Ih):

Formula (Ih)

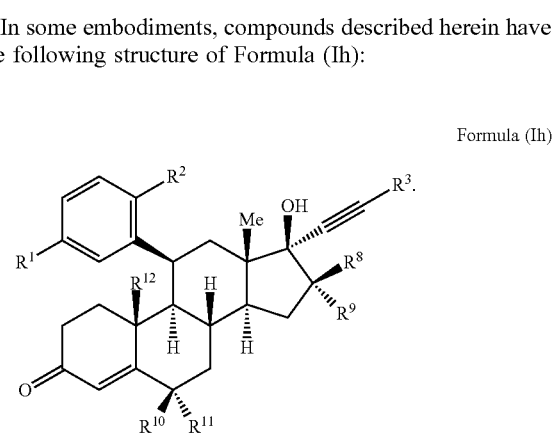

In some embodiments, compounds described herein have the following structure of Formula (Ii):

Formula (Ii)

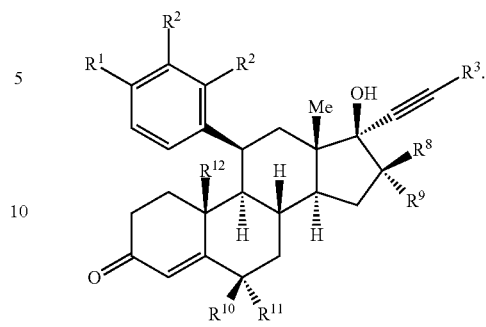

In some embodiments, compounds described herein have the following structure of Formula (Ij):

Formula (Ij)

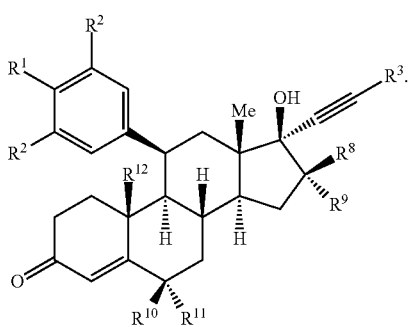

In some embodiments, compounds described herein have the following structure of Formula (Ik):

Formula (Ik)

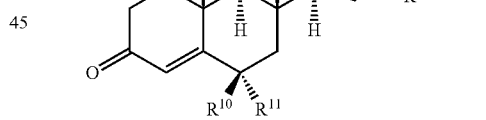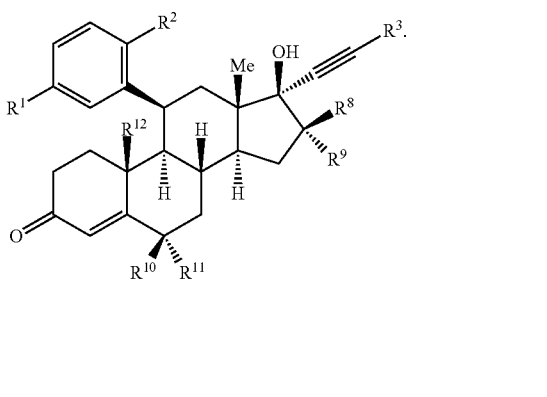

In some embodiments, compounds described herein have the following structure of Formula (Im):

Formula (Im)

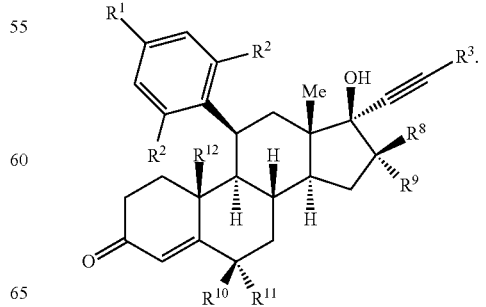

In some embodiments, compounds described herein have the following structure of Formula (In):

Formula (In)

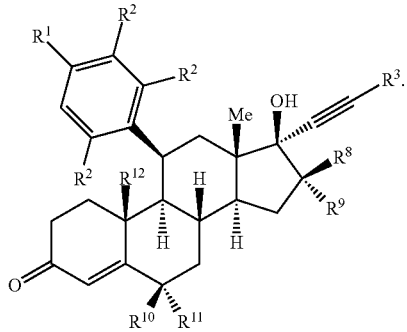

In some embodiments, compounds described herein have the following structure of Formula (Io):

Formula (Io)

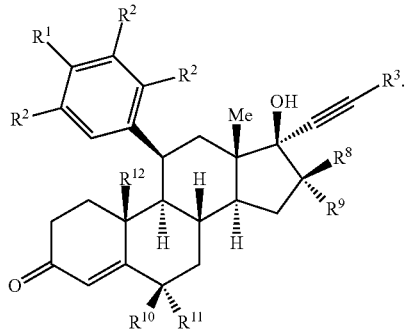

In some embodiments, compounds described herein have the following structure of Formula (Ip):

Formula (Ip)

In some embodiments, compounds described herein have the following structure of Formula (Iq):

Formula (Iq)

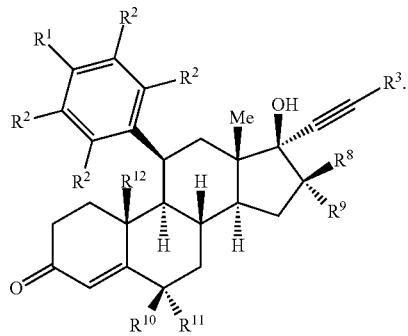

In some embodiments, compounds described herein have the following structure of Formula (Ir) or Formula (Is):

Formula (Ir)

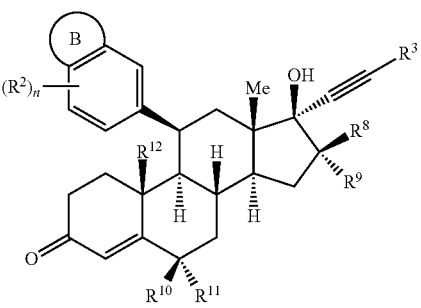

Formula (Is)

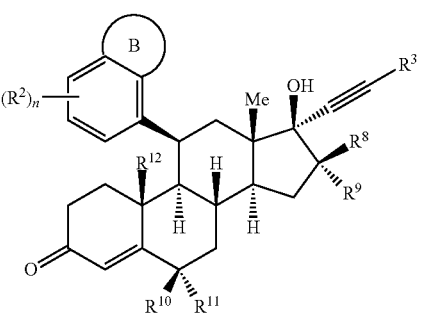

wherein ring B is an optionally substituted fused carbocyclyl, optionally substituted fused heterocyclyl, optionally substituted fused aryl, or optionally substituted fused heteroaryl;

and n is 0, 1, 2, or 3.

In some embodiments, the substituted steroidal derivative compound described in Formulas provided herein has a structure provided in Table 1.

TABLE 1

| No. | Structure | Mass, [M + H]+ |
|-----|-----------|----------------|
| 1 | 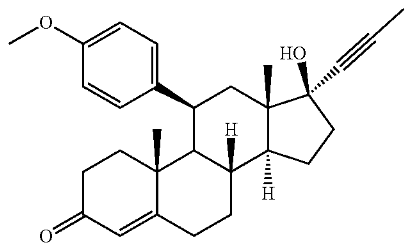 | 433.4 |
| 2 | 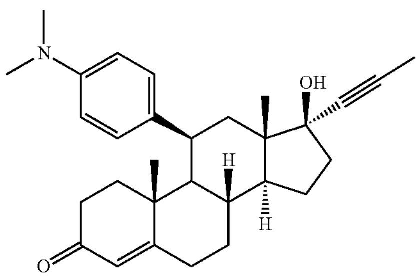 | 446.4 |
| 3 | 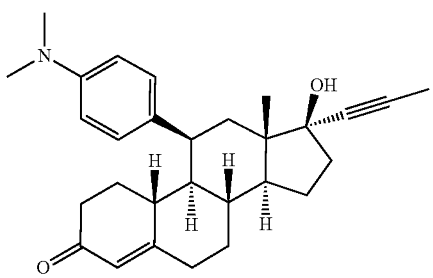 | 432.4 |
| 4 | 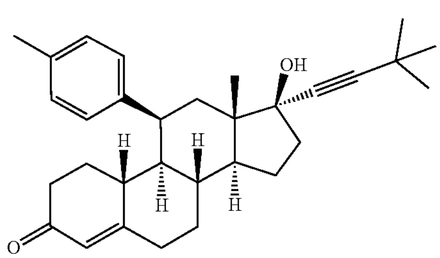 | 445.4 |
| 5 | 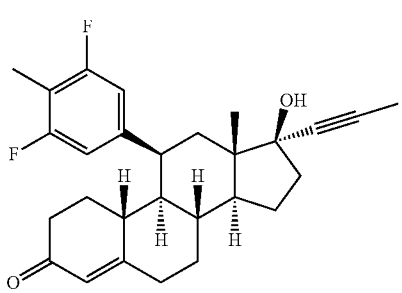 | 439.3 |

TABLE 1-continued

| No. | Structure | Mass, [M + H]+ |
|---|---|---|
| 6 | 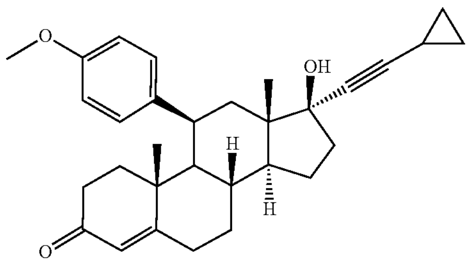 | 459.4 |
| 7 | 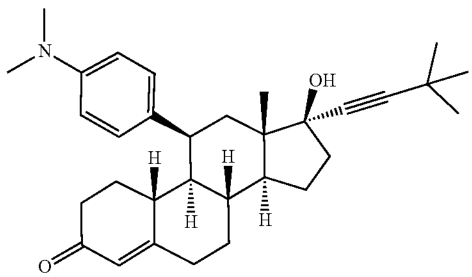 | 474.4 |
| 8 | 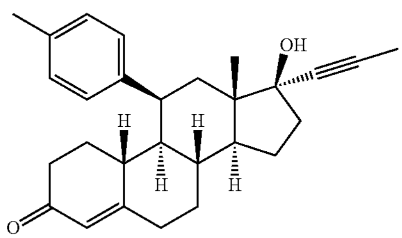 | 403.4 |
| 9 | 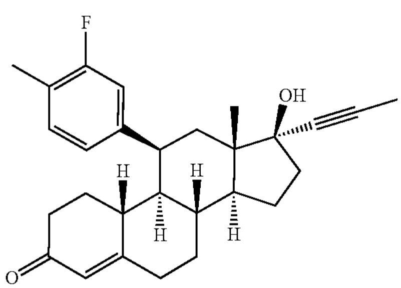 | 421.3 |
| 10 | 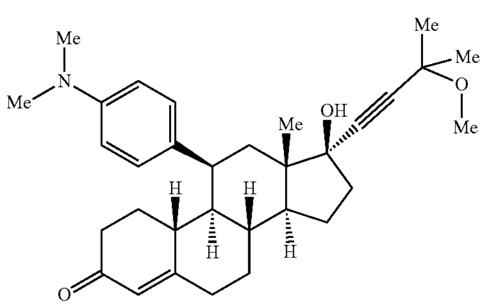 | 490.4 |

TABLE 1-continued

| No. | Structure | Mass, [M + H]+ |
|---|---|---|
| 11 | 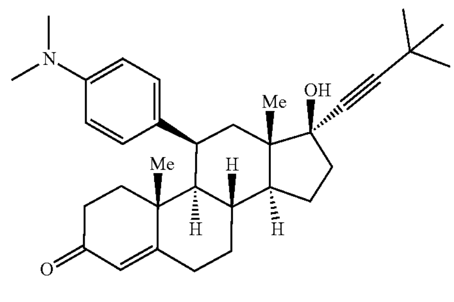 | 488.5 |
| 12 | 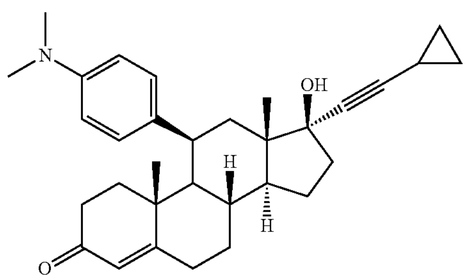 | 472.4 |
| 13 | 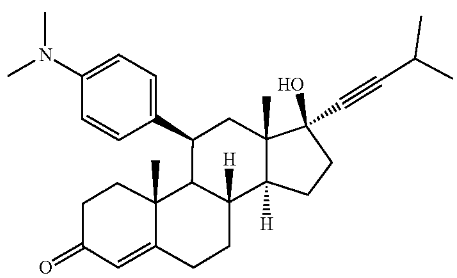 | 474.4 |
| 14 | 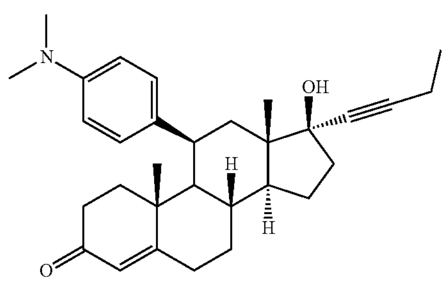 | 460.4 |
| 15 | 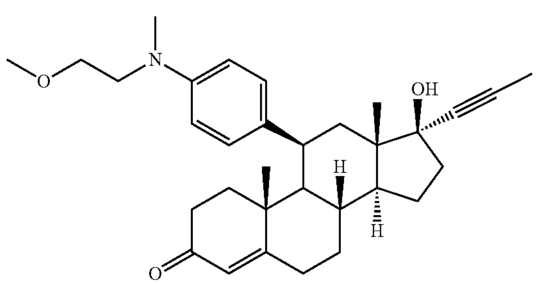 | 490.4 |

TABLE 1-continued

| No. | Structure | Mass, [M + H]+ |
|---|---|---|
| 16 | 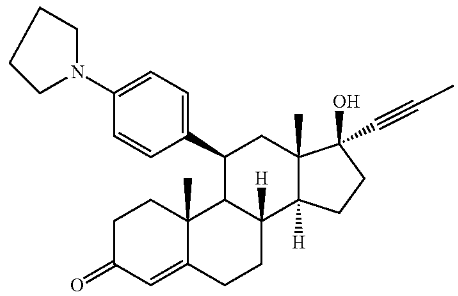 | 472.4 |

In some embodiments, the substituted steroidal derivative compound described in Formulas provided herein has a structure provided in Table 2.

TABLE 2

| No. | Structure |
|---|---|
| 17 | 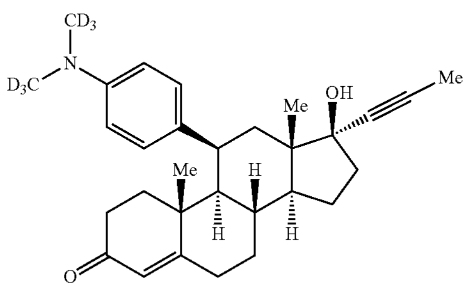 |
| 18 | 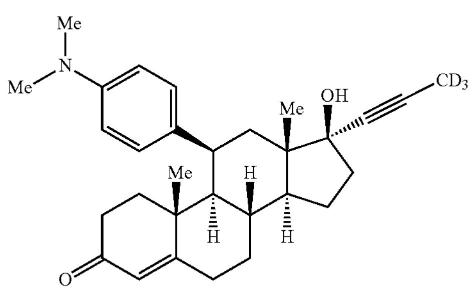 |
| 19 | 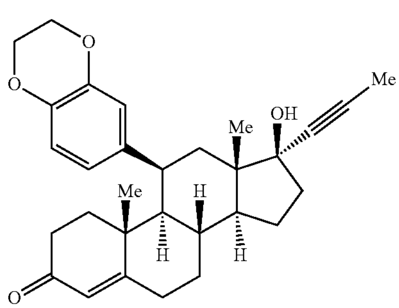 |
| 20 | |
| 21 | |
| 22 | |

TABLE 2-continued

| No. | Structure |
|---|---|
| 23 | (steroidal structure with p-(dimethylamino)phenyl at C11, Me at C13, OH and C≡C-Me at C17) |
| 24 | (steroidal structure with p-(1,1-dioxo-thiomorpholin-4-yl)phenyl at C11, Me at C13, OH and C≡C-Me at C17) |
| 25 | (steroidal structure with 3-isopropylphenyl at C11, Me at C13, OH and C≡C-Me at C17) |
| 26 | (steroidal structure with p-(dimethylamino)phenyl at C11, Me at C13, OH and C≡C-C(Me)₂-O-Me at C17) |

Preparation of the Substituted Steroidal Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the substituted steroidal derivative compounds described herein is P. H. Stahl & C. G. Wermuth "Handbook of Pharmaceutical Salts", Verlag Helvetica Chimica Acta, Zurich, 2002.

Pharmaceutical Compositions of the Substituted Steroidal Derivative Compounds

In certain embodiments, the substituted steroidal derivative compound as described herein is administered as a pure chemical. In other embodiments, the substituted steroidal derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one substituted steroidal derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of any of the Formulas provided herein, or a pharmaceutically acceptable salt thereof, and a pharmaceutically acceptable excipient.

In certain embodiments, the substituted steroidal derivative compound as described by any of the Formulas provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted steroidal derivative compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Use of the Substituted Steroidal Derivative Compounds Glucocorticoid Receptor Modulators Mifepristone is a non-selective modulator of several nuclear receptors. Mifepristone has been referred to as a GR antagonist, a progesterone receptor (PR) antagonist, a GR partial agonist, an androgen receptor (AR) antagonist and an AR partial agonist in the scientific literature. The activity observed at multiple hormone receptors leads to various undesirable side effects and in some instances, the promotion of cancer. Thus, AR agonism is an undesirable feature for GR antagonists used in the treatment of cancer (e.g., AR positive or AR dependent cancers including "castration resistant" prostate cancer (CRPC), breast cancer, or ovarian cancer). Antagonists of GR that have minimized binding to other hormone receptors, such as the androgen receptor (AR), are needed to effectively treat the diseases described herein with reduced side effects.

Some embodiments provided herein describe compounds that are modulators of glucocorticoid receptors (GR). In some embodiments, the compounds alter the level and/or activity of GR. In some embodiments, the compounds described herein are GR inhibitors. In some embodiments, the GR inhibitors are GR antagonists. In some instances, glucocorticoid receptor antagonists bind to the receptor and prevent glucocorticoid receptor agonists from binding and eliciting GR mediated events, including transcription. Thus, in some embodiments, the compounds described herein inhibit GR transcriptional activation activity. In some embodiments, the compounds described herein are selective GR antagonists. In some embodiments, the compounds described herein are not GR agonists. In some embodiments, the compounds described herein are not GR partial agonists. In some embodiments, the GR inhibitors lessen cortisol activity in cells and make secondary therapeutic agents more effective.

GR antagonists are useful for treating or preventing weight gain (e.g., Olanzapine induced weight gain), uterine fibrosis, alcoholism, alcohol abuse disorders, cocaine dependence, bipolar depression, adrenal hypercortisolism, post-traumatic stress disorder, anxiety disorders, mood disorders, hyperglycemia, and to induce abortion.

In some embodiments, the GR inhibitors described herein are also androgen receptor (AR) signaling inhibitors. In certain embodiments, the AR signaling inhibitors are AR antagonists. In some instances, AR antagonists bind to AR and prevent AR agonists from binding and eliciting AR mediated events, including transcription. In other embodiments, the GR inhibitors are not androgen receptor (AR) signaling inhibitors. In these instances, the GR inhibitors do not significantly activate AR levels and/or activity. In some embodiments, the GR inhibitors are not AR agonists.

In some embodiments, the GR inhibitors described herein have minimized binding to the androgen receptor (AR). In some embodiments, the compounds described herein are not AR agonists. In some embodiments, the compounds described herein are not partial AR agonists. In some embodiments, the compounds described herein have minimized partial AR agonism compared to mifepristone.

In some embodiments, the GR inhibitors described herein are not partial AR agonists or partial GR agonists.

In some embodiments, the GR inhibitors described herein do not modulate progesterone receptors. In some embodiments, the GR inhibitors described herein are not progesterone receptor (PR) inhibitors. In these instances, the GR inhibitors do not significantly activate PR levels and/or activity. In some embodiments, the GR inhibitors are not PR agonists. In some embodiments, the GR inhibitors are not PR partial agonists. In some embodiments, the GR inhibitors are not PR antagonists.

In some embodiments, the GR inhibitors (e.g., GR antagonists) are selective inhibitors. In some embodiments, use of the GR inhibitors in a patient does not cause or result in vaginal bleeding, cramping, nausea, vomiting, diarrhea, dizziness, back pain, weakness, tiredness, or combinations thereof. In certain embodiments, use of the GR inhibitors in a patient does not cause or result in vaginal bleeding. In certain embodiments, use of the GR inhibitors in a patient does not cause or result in cramping. In some embodiments, use of the GR inhibitors in a patient does not cause or result in allergic reactions, low blood pressure, loss of consciousness, shortness of breath, rapid heartbeat, or combinations thereof.

Methods of Treatment

Cancer

One embodiment provides a method of treating cancer in a subject in need thereof, comprising administering to the subject a compound of any of the Formulas provided herein, or a pharmaceutically acceptable salt thereof. In some embodiments, a GR inhibitor described herein is used in combination with a second therapeutic agent (e.g., an anti-cancer agent) for treating cancer. In some embodiments, the combination of the GR inhibitor with the second therapeutic agent (e.g., an anti-cancer agent) provides a more effective initial therapy for treating cancer compared to the second therapeutic agent (e.g., an anti-cancer agent) administered alone. In some embodiments, a GR inhibitor described herein is used in combination with one or more additional therapeutic agents (e.g., anti-cancer agents) for treating cancer. In some embodiments, the combination of the GR inhibitor with the one or more additional therapeutic agents (e.g., an anti-cancer agents) provides a more effective initial therapy for treating cancer compared to the one or more therapeutic agents (e.g., an anti-cancer agents) administered alone.

In some embodiments, the cancer is chemoresistant cancer, radio resistant cancer, or refractory cancer. In some embodiments, the cancer is relapsed cancer, persistent cancer, or recurrent cancer. Another embodiment provided herein describes a method of reducing incidences of cancer recurrence. Also provided here in some embodiments, is a method for treating a chemo-resistant cancer.

Prostate Cancer

Prostate cancer is the second most common cause of cancer death in men in the United States, and approximately one in every six American men will be diagnosed with the disease during his lifetime. Treatment aimed at eradicating the tumor is unsuccessful in 30% of men.

One embodiment provides a method of treating prostate cancer in a subject in need thereof, comprising administering to the subject a compound of any of the Formulas provided herein, or a pharmaceutically acceptable salt thereof. In some embodiments, a GR inhibitor described herein is used in combination with a second therapeutic agent (e.g., an anti-cancer agent) for treating prostate cancer. In some embodiments, the combination of the GR inhibitor with the second therapeutic agent (e.g., an anti-cancer agent) provides a more effective initial therapy for treating prostate cancer compared to the second therapeutic agent (e.g., an anti-cancer agent) administered alone. In some embodiments, a GR inhibitor described herein is used in combination with one or more additional therapeutic agents (e.g., anti-cancer agents) for treating prostate cancer. In some embodiments, the combination of the GR inhibitor with the one or more additional therapeutic agents (e.g., an anti-cancer agents) provides a more effective initial therapy for treating prostate cancer compared to the one or more therapeutic agents (e.g., an anti-cancer agents) administered alone.

In some embodiments, the prostate cancer is chemoresistant cancer, radio resistant cancer, antiandrogen resistant, or refractory cancer. In some embodiments, the prostate cancer is relapsed cancer, persistent cancer, or recurrent cancer.

In some embodiments, the prostate cancer is acinar adenocarcinoma, atrophic carcinoma, foamy carcinoma, colloid carcinoma, or signet ring carcinoma. In some embodiments, the prostate cancer is ductal adenomcarcinoma, transitional cell cancer, urothelial cancer, squamous cell cancer, carcinoid cancer, small cell cancer, sarcoma cancer, or sarcomatoid cancer. In some embodiments, the prostate cancer is metastatic castration-resistant prostate cancer, doubly-resistant prostate cancer, castration-resistant prostate cancer, hormone-resistant prostate cancer, androgen-independent, or androgen-refractory cancer.

In some instances, antiandrogens are useful for the treatment of prostate cancer during its early stages. In some instances, prostate cancer cells depend on androgen receptor (AR) for their proliferation and survival. Some prostate cancer patients are physically castrated or chemically castrated by treatment with agents that block production of testosterone (e.g. GnRH agonists), alone or in combination with antiandrogens, which antagonize effects of any residual testosterone.

In some instances, prostate cancer advances to a hormone-refractory state in which the disease progresses despite continued androgen ablation or antiandrogen therapy. The hormone-refractory state to which most patients eventually progresses in the presence of continued androgen ablation or anti-androgen therapy is known as "castration resistant" prostate cancer (CRPC). CRPC is associated with an over-expression of AR. AR is expressed in most prostate cancer cells and overexpression of AR is necessary and sufficient for androgen-independent growth of prostate cancer cells. Failure in hormonal therapy, resulting from development of androgen-independent growth, is an obstacle for successful management of advanced prostate cancer.

While a small minority of CRPC does bypass the requirement for AR signaling, the vast majority of CRPC, though frequently termed "androgen independent prostate cancer" or "hormone refractory prostate cancer," retains its lineage dependence on AR signaling.

Recently approved therapies that target androgen receptor (AR) signaling such as abiraterone and enzalutamide have been utilized for treating CRPC. Despite these successes, sustained response with these agents is limited by acquired resistance which typically develops within 6-12 months. Doubly resistant prostate cancer is characterized in that tumor cells have become castration resistant and overexpress AR, a hallmark of CRPC. However, cells remain resistant when treated with second generation antiandrogens. Doubly resistant prostate cancer cells are characterized by a lack of effectiveness of second generation antiandrogens in inhibiting tumor growth.

As discussed above, resistant prostate cancer (e.g., doubly resistant and castration resistant prostate cancers) occurs when cancer cells overexpress androgen receptors (AR). AR target gene expression is inhibited when the cells are treated with a second generation antiandrogen. In some instances, increased signaling through the glucocorticoid receptor (GR) compensates for inhibition of androgen receptor signaling in resistant prostate cancer. Double resistant prostate cancer develops when expression of a subset of those AR target genes is restored. In some instances, GR activation is responsible for this target gene activation. In some embodiments, GR transcription is activated in patients susceptible to or suffering from resistant prostate cancer (e.g., doubly resistant and castration resistant prostate cancers). In some instances, GR upregulation in cancer cells confers resistance to antiandrogens.

Some embodiments provided herein describe the use of the GR inhibitors for treating prostate cancer in a subject in need thereof, including doubly resistant prostate cancer and castration resistant prostate cancer. In some embodiments, the subject in need has elevated tumor GR expression. In some embodiments, the GR inhibitor is also an AR signaling inhibitor or antiandrogen.

In some embodiments, the GR inhibitor is used in combination with a second therapeutic agent. In some embodiments, the GR inhibitor is used in combination with one or more additional therapeutic agents. In some embodiments, the second or additional agent is an anti-cancer agent. In certain embodiments, the anti-cancer agent is useful for AR positive or AR negative prostate cancer.

In some embodiments, the second or additional agent is an AR signaling inhibitor or antiandrogen. In certain embodiments, the AR signaling inhibitor is an AR antagonist. In some embodiments, the second or additional therapeutic agent is selected from finasteride, dutasteride, alfatradiol, cyproterone acetate, spironolactone, danazol, gestrinone, ketoconazole, abiraterone acetate, enzalutamide, ARN-509, danazol, gestrinone, danazol, simvastatin, aminoglutethimide, atorvastatin, simvastatin, progesterone, cyproterone acetate, medroxyprogesterone acetate, megestrol acetate, chlormadinone acetate, spironolactone, drospirenone, estradiol, ethinyl estradiol, diethylstilbestrol, conjugated equine estrogens, buserelin, deslorelin, gonadorelin, goserelin, histrelin, leuprorelin, nafarelin, triptorelin, abarelix, cetrorelix, degarelix, ganirelix, or any combinations or any salts thereof. In some embodiments, the second or additional therapeutic agent is selected from flutamide, nilutamide, bicalutamide, enzalutamide, apalutamide, cyproterone acetate, megestrol acetate, chlormadinone acetate, spironolactone, canrenone, drospirenone, ketoconazole, topilutamide, cimetidine, or any combinations or any salts thereof. In some embodiments, the AR signaling inhibitor is 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosteride, or any combinations thereof. In some embodiments, the AR signaling inhibitor is flutamide, nilutamide, bicalutamide, or megestrol. In some embodiments, the AR signaling inhibitor is ARN-509. In other embodiments, the AR signaling inhibitor is enzalutamide.

In some embodiments, the anti-cancer agent is mitoxantrone, estramustine, etoposide, vinblastine, carboplatin, vinorelbine, paclitaxel, daunomycin, darubicin, epirubicin, docetaxel, cabazitaxel, or doxorubicin. In some embodiments, the anti-cancer agent is paclitaxel, daunomycin, darubicin, epirubicin, docetaxel, cabazitaxel, or doxorubicin. In certain embodiments, the anti-cancer agent is docetaxel.

Breast Cancer

Breast cancer is the second leading cause of cancer among women in the United States. Triple-negative breast cancers are among the most aggressive and difficult to treat of all the breast cancer types. Triple-negative breast cancer is a form of the disease in which the three receptors that fuel most breast cancer growth—estrogen, progesterone and the HER-2—are not present. Because the tumor cells lack these receptors, treatments that target estrogen, progesterone and HER-2 are ineffective. Approximately 40,000 women are diagnosed with triple-negative breast cancer each year. It is estimated that more than half of these women's tumor cells express significant amounts of GR.

In some instances, GR expression is associated with a poor prognosis in estrogen receptor (ER)-negative early stage breast cancer. In some instances, GR activation in triple-negative breast cancer cells initiates an anti-apoptotic gene expression profile that is associated with inhibiting chemotherapy-induced tumor cell death. GR activity in these cancer cells correlate with chemotherapy resistance and increased recurrence of cancer.

Provided herein in some embodiments are methods of treating breast cancer, the method comprising administering to a subject in need thereof a compound of any of the Formulas provided herein, or a pharmaceutically acceptable salt thereof. In some embodiments, a GR inhibitor described herein is used in combination with a second therapeutic agent (e.g., a chemotherapeutic agent) for treating breast cancer. In some embodiments, the combination of the GR inhibitor with the second therapeutic agent (e.g., a chemotherapeutic agent) provides a more effective initial therapy for treating breast cancer compared to the second therapeutic agent (e.g., a chemotherapeutic agent) administered alone. In some embodiments, a GR inhibitor described herein is used in combination with one or more additional therapeutic agents (e.g., anti-cancer agents) for treating breast cancer. In some embodiments, the combination of the GR inhibitor with the one or more additional therapeutic agents (e.g., an anti-cancer agents) provides a more effective initial therapy for treating breast cancer compared to the one or more therapeutic agents (e.g., an anti-cancer agents) administered alone.

In some embodiments, the breast cancer is chemoresistant cancer, radio resistant cancer, or refractory cancer. In some embodiments, the breast cancer is relapsed cancer, persistent cancer, or recurrent cancer. Breast cancers may include, but are not limited to, ductal carcinoma, invasive ductal carcinoma, tubular carcinoma of the breast, medullary carcinoma of the breast, mecinous carcinoma of the breast, papillary carcinoma of the breast, cribriform carcinoma of the breast, invasive lobular carcinoma, inflammatory breast cancer, lobular carcinoma in situ, male breast cancer, Paget disease of the nipple, phyllodes tumor of the breast, recurrent and metastatic breast cancer, triple-negative breast cancer, or combinations thereof.

In some embodiments, the breast cancer is recurrent and metastatic breast cancer, triple-negative breast cancer, or combinations thereof. In some embodiments, the breast cancer is chemoresistant triple-negative breast cancer or estrogen receptor (ER) negative breast cancer. In some embodiments, the breast cancer is chemoresistant triple-negative breast cancer. In some embodiments, the breast cancer is estrogen receptor (ER) negative breast cancer. In some embodiments, the breast cancer is GR+ triple-negative breast cancer. In some embodiments, the breast cancer is GR+ estrogen receptor (ER) negative breast cancer.

Some embodiments provided herein describe the use of GR inhibitors for treating breast cancer in a patient, including triple negative breast cancer or ER negative breast cancer. In some embodiments, GR inhibitors inhibit the anti-apoptotic signaling pathways of GR and increase the cytotoxic efficiency of secondary chemotherapeutic agents. In some embodiments, the GR inhibitors described herein enhance the efficacy of chemotherapy in breast cancer patients, such as triple negative breast cancer patients. In some embodiments, the breast cancer patient has elevated tumor GR expression.

In some embodiments, a GR inhibitor described herein is used in combination with a second therapeutic agent, such as chemotherapy or immunotherapy. In some embodiments, a GR inhibitor described herein is used in combination with one or more additional therapeutic agents. In some embodiments, the second or additional chemotherapeutic agent is cisplatin, carboplatin, cyclophosphamide, capecitabine, gemcitabine, paclitaxel, nab-paclitaxel, altretamine, docetaxel, epirubicin, melphalan, methotrexate, mitoxantrone, ixabepilone, ifosfamide, irinotecan, eribulin, etoposide, doxorubicin, liposomal doxorubicin, camptothecin, pemetrexed, topotecan, vinorelbine, daunorubicin, fluorouracil, mitomycin, thiotepa, vincristine, everolimus, veliparib, glembatumumab vedotin, pertuzumab, trastuzumab, or any combinations or any salts thereof. In some embodiments, the second or additional therapeutic agent is an anti-PD-L1 agent. In certain embodiments, the anti-PD-L1 agent is MPDL3280A or avelumab. In some embodiments, the second or additional therapeutic agent is an anti-PD1 agent. In certain embodiments, the anti-PD1 agent is nivolumab or permbrolizumab.

Some embodiments provided herein describe methods of treating estrogen positive breast cancer. In some instances, estrogen positive breast cancer patients become resistant to estrogen receptor modulators. In some embodiments, the GR inhibitors described herein enhance the efficacy of estrogen receptor modulators in estrogen positive breast cancer patients. In some embodiments, the breast cancer patient has elevated tumor GR expression. In some embodiments, a GR inhibitor described herein is used in combination with an estrogen receptor modulator. In some embodiments, the estrogen receptor modulator is tamoxifen, raloxifene, toremifene, tibolone, fulvestrant, lasofoxifene, clomifene, ormeloxifene, or ospemifene. In some embodiments, the estrogen receptor modulator is tamoxifen, raloxifene, toremifene, tibolone, or fulvestrant. In some embodiments, the estrogen receptor modulator is tamoxifen, raloxifene, or toremifene. In certain embodiments, the estrogen receptor modulator is tamoxifen.

Ovarian Cancer

Ovarian cancer is the leading cause of death from gynecologic malignancies. Some ovarian cancers (e.g., high grade serous ovarian cancer) are initially sensitive to platinum-based therapy, but relapse rates remain high.

One embodiment provides a method of treating ovarian cancer in a patient in need thereof, comprising administering to the patient a compound of any of the Formulas provided herein, or a pharmaceutically acceptable salt thereof. In some embodiments, the patient has elevated tumor GR expression. In some embodiments, a GR inhibitor described herein is used in combination with a second therapeutic agent (e.g., a chemotherapeutic agent) for treating ovarian cancer. In some embodiments, the combination of the GR inhibitor with the second therapeutic agent (e.g., a chemotherapeutic agent) provides a more effective initial therapy for treating ovarian cancer compared to the second therapeutic agent (e.g., a chemotherapeutic agent) administered alone. In some embodiments, a GR inhibitor described herein is used in combination with one or more additional therapeutic agents (e.g., anti-cancer agents) for treating ovarian cancer. In some embodiments, the combination of the GR inhibitor with the one or more additional therapeutic agents (e.g., an anti-cancer agents) provides a more effective initial therapy for treating ovarian cancer compared to the one or more therapeutic agents (e.g., an anti-cancer agents) administered alone.

In some instances, GR activation increases resistance to chemotherapy in ovarian cancer (e.g., high-grade serous ovarian cancer). In some instances, GR activation significantly inhibits chemotherapy induced apoptosis in ovarian cancer cells. Provided herein in some embodiments are methods of treating ovarian cancer in a subject, the method comprising treating the subject with a GR inhibitor (e.g., GR antagonist) to improve sensitivity to chemotherapy. In some embodiments, the ovarian cancer has become resistant to chemotherapy. In some embodiments, the ovarian cancer cells are resistant to cisplatin, paclitaxel, carboplatin, gemcitabine, alone or in combination. In some embodiments, the GR inhibitor or antagonist reverses the cell survival effect.

Ovarian cancers may include, but are not limited to, epithelial ovarian cancers, such as serous epithelial ovarian cancer, endometrioid epithelial ovarian cancer, clear cell epithelial ovarian cancer, mucinous epithelial ovarian cancer, undifferentiated or unclassifiable epithelial ovarian cancer, refractory ovarian cancer, sex cord-stromal tumors, Sertoli and Sertoli-Leydig cell tumors, germ cell tumors, such as dysgerminoma and nondysgerminomatous tumors, Brenner tumors, primary peritoneal carcinoma, fallopian tube cancer, or combinations thereof.

In some embodiments, the GR inhibitor is used in combination with at least a second therapeutic agent, such as chemotherapy or immunotherapy. In some embodiments, the GR inhibitor is used in combination with one or more additional therapeutic agents. In some embodiments, the second or additional chemotherapeutic agent is cisplatin, carboplatin, cyclophosphamide, capecitabine, gemcitabine, paclitaxel, nab-paclitaxel, altretamine, docetaxel, epirubicin, melphalan, methotrexate, mitoxantrone, ixabepilone, ifosfamide, irinotecan, eribulin, etoposide, doxorubicin, liposomal doxorubicin, camptothecin, pemetrexed, topotecan, vinorelbine, daunorubicin, fluorouracil, mitomycin, thiotepa, vincristine, everolimus, veliparib, glembatumumab vedotin, pertuzumab, trastuzumab, or any combinations or any salts thereof. In some embodiments, the second or additional chemotherapeutic agent is gemcitabine. In some embodiments, the second or additional chemotherapeutic agent is carboplatin. In some embodiments, the second or additional chemotherapeutic agent is cisplatin. In some embodiments, the second or additional agent is paclitaxel. In some embodiments, the GR inhibitor is used in combination with gemcitabine and carboplatin. In some embodiments, the GR inhibitor is used in combination with carboplatin and cisplatin. In some embodiments, the second or additional therapeutic agent is an anti-PD-L1 agent. In certain embodiments, the anti-PD-L1 agent is MPDL3280A or avelumab. In some embodiments, the second or additional therapeutic agent is an anti-PD1 agent. In certain embodiments, the anti-PD1 agent is nivolumab or permbrolizumab.

Non-Small Cell Lung Cancer

One embodiment provides a method of treating non-small cell lung cancer (NSCLC) in a patient in need thereof, comprising administering to the patient a compound of any of the Formulas provided herein, or a pharmaceutically acceptable salt thereof. In some embodiments, the patient has elevated tumor GR expression. In some embodiments, a GR inhibitor described herein is used in combination with a second therapeutic agent (e.g., a chemotherapeutic agent) for treating NSCLC. In some embodiments, the combination of the GR inhibitor with the second therapeutic agent (e.g., a chemotherapeutic agent) provides a more effective initial therapy for treating NSCLC compared to the second therapeutic agent (e.g., a chemotherapeutic agent) administered alone. In some embodiments, a GR inhibitor described herein is used in combination with one or more additional therapeutic agents (e.g., anti-cancer agents) for treating NSCLC. In some embodiments, the combination of the GR inhibitor with the one or more additional therapeutic agents (e.g., an anti-cancer agents) provides a more effective initial therapy for treating NSCLC compared to the one or more therapeutic agents (e.g., an anti-cancer agents) administered alone.

In some embodiments, the GR inhibitor is used in combination with at least a second therapeutic agent, such as a chemotherapeutic agent or immunotherapy. In some embodiments, the GR inhibitor is used in combination with one or more additional therapeutic agents. In some embodiments, the second or additional chemotherapeutic agent is cisplatin, carboplatin, cyclophosphamide, capecitabine, gemcitabine, paclitaxel, nab-paclitaxel, altretamine, docetaxel, epirubicin, melphalan, methotrexate, mitoxantrone, ixabepilone, ifosfamide, irinotecan, eribulin, etoposide, doxorubicin, liposomal doxorubicin, camptothecin, pemetrexed, topotecan, vinorelbine, vinblastine, daunorubicin, fluorouracil, mitomycin, thiotepa, vincristine, everolimus, veliparib, glembatumumab vedotin, pertuzumab, trastuzumab, or any combinations or any salts thereof. In some embodiments, the second or additional chemotherapeutic agent is gemcitabine. In some embodiments, the second or additional chemotherapeutic agent is carboplatin. In some embodiments, the second or additional chemotherapeutic agent is cisplatin. In some embodiments, the second or additional agent is paclitaxel. In some embodiments, the GR inhibitor is used in combination with gemcitabine and carboplatin. In some embodiments, the GR inhibitor is used in combination with carboplatin and cisplatin. In some embodiments, the second or additional therapeutic agent is an anti-PD-L1 agent. In certain embodiments, the anti-PD-L1 agent is MPDL3280A or avelumab. In some embodiments, the second or additional therapeutic agent is an anti-PD1 agent. In certain embodiments, the anti-PD1 agent is nivolumab or permbrolizumab.

Hypercortisolism/Cushing's Disease

One embodiment provides a method of treating hypercortisolism or Cushing's disease in a patient in need thereof, comprising administering to the patient a compound of any of the Formulas provided herein, or a pharmaceutically acceptable salt thereof.

Types of Cushing's disease include, but are not limited to, recurrent Cushing's disease, refractory Cushing's disease, persistent Cushing's disease, endogenous Cushing's disease, spontaneous hypercortisolism, Adrenocorticotropic hormone dependent, Adrenocorticotropic hormone independent, or combinations thereof.

Causes of hypercortisolism may include, but are not limited to, prolonged exposure to cortisol, a tumor that produces excessive cortisol, a tumor that results in the excess production of cortisol, or combinations thereof.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1

Compound 1. (8S,9R,10R,11S,13S,14S,17S)-17-Hydroxy-11-(4-methoxyphenyl)-10,13-dimethyl-17-(prop-1-yn-1-yl)-1,2,6,7,8,9,10,11,12,13,14,15,16, 17-tetradecahydro-3H-cyclopenta[a]phenanthren-3-one

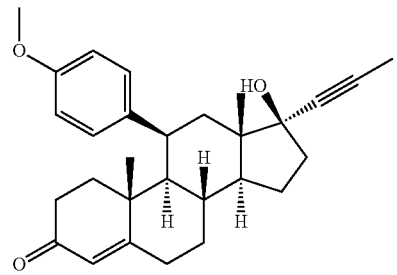

STEP A. (8'S,9'S,10'R,13'S,14'S)-10',13'-Dimethyl-1',2',4',7',8',9',10',12',13',14',15',16'-dodecahydro-11'H-dispiro[[1,3]dioxolane-2,3'-cyclopenta[a]phenanthrene-17',2"-[1,3]dioxolan]-11'-one

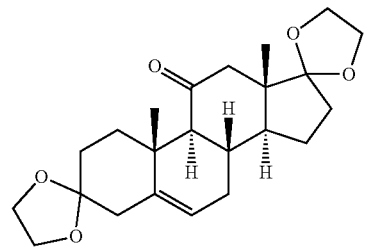

Adrenosterone (50.2 g, 1 eq,) was dissolved in 390 ml DCM with 91 g of trimethylorthoformate (5.2 eq) and 119 g of ethylene glycol (11.5 eq). Toluenesulfonic acid (1.9 g, 0.06 eq) was added. The reaction was heated to 40° C. for 18 h. The dark colored solution was quenched with 4 ml pyridine. The reaction was concentrated to remove solvents. The residue was taken up in DCM and washed with water. The organic layer was dried with MgSO$_4$, filtered and concentrated to give 74.3 g of a mushy solid. The solid was purified to give 42.2 g (64.9%) of the title compound. m/z (ESI, +ve ion) 389.3 (M+H)$^+$.

STEP B. (8'S,9'S,10'R,13'R,14'S)-10',13'-Dimethyl-11'-(((4,4,4,4,4,4,4,4,4-nonafluoro-4112-buta-1,3-diyn-1-yl)thio)trioxidanyl)-1',4',7',8',9',10',13',14',15',16'-decahydro-2'H-dispiro[[1,3]dioxolane-2,3'-cyclopenta[a]phenanthrene-17',2"-[1,3]dioxolane]

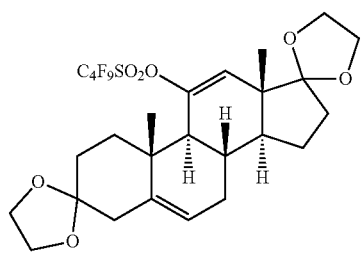

Lithium diisopropylamide solution was prepared as follows. In an oven-dried 500 mL flask a solution of 125 mL THF and anhydrous diisopropylamine (5.77 mL, 4.1 eq) was cooled in a dry ice-acetone bath. N-butyl lithium (25.1 mL, 4 eq, 1.6 M in hexanes) was added slowly and the reaction was stirred for 25 min.

A separate flask was charged with the starting bis-ketal (Step A) (3.9 g, 1 eq), azeotroped with toluene, dried under vacuum, flushed with Ar and kept under an Ar balloon. 40 mL of THF was added to dissolve the bis-ketal. This solution was added slowly to the freshly prepared LDA solution maintained at −78° C. The reaction was stirred for 30 min, then perfluorobutanesulfonyl fluoride (5.4 mL, 3 eq) was added. The reaction was maintained in the cold bath for another hour. The bath was removed and the mixture allowed to stir at rt overnight. After 24 h, additional 2.5 mL perfluorobutanesulfonyl fluoride was added and the reaction was stirred overnight again. Saturated aq. NH$_4$Cl was added to the reaction, followed by extraction with EtOAc. The organic layer was washed with brine and dried with MgSO$_4$. After concentration under vacuum, the residue was purified by silica gel chromatography to give the desired product as a light yellow solid (3.7 g, 55%). m/z (ESI, +ve ion) 671.2 (M+H)$^+$.

STEP C. (8'S,9'S,10'R,13'R,14'S)-11'-(4-Methoxyphenyl)-10',13'-dimethyl-1',4',7',8',9',10',13',14',15',16'-decahydro-2'H-dispiro[[1,3]dioxolane-2,3'-cyclopenta[a]phenanthrene-17',2"-[1,3]dioxolane]

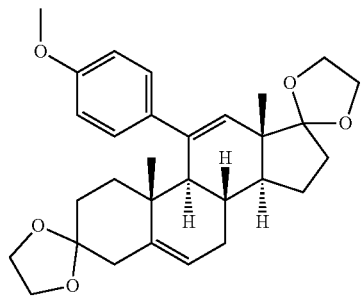

A flask was charged with (8'S,9'S,10'R,13'R,14'S)-10',13'-dimethyl-11'-(((4,4,4,4,4,4,4,4,4-nonafluoro-4112-buta-1,3-diyn-1-yl)thio)trioxidanyl)-1',4',7',8',9',10',13',14',15',16'-decahydro-2'H-dispiro[[1,3]dioxolane-2,3'-cyclopenta[a]phenanthrene-17',2"-[1,3]dioxolane (Step B) (3.49 g, 1 eq), 4-methoxyphenyl boronic acid (7.9 g, 10 eq), lithium chloride (441 mg, 2 eq), Pd(PPh$_3$)$_4$ (481 mg, 0.08 eq). Then toluene (70 mL), ethanol (35 mL), and Na$_2$CO$_3$ (2M, 19.5 mL, 7.5 eq) were added and the reaction mixture was degassed with argon. The reaction was heated to reflux for 42 hours until no more starting material was evident. (TLC in 3:1 hexanes:EtOAc). After cooling, the reaction was quenched with aq. NaHCO$_3$ solution and extracted with EtOAc. The organic layer was separated, washed with saturated brine solution, dried with MgSO$_4$, filtered and concentrated to dryness in vacuo.

Purification by flash silica gel column chromatography provided the title compound (2.25 g, 90%) as a white solid. m/z (ESI, +ve ion) 479.3 (M+H)$^+$.

STEP D. (4a'R,5a'S,6a'S,6b'S,9a'R,11a'R,11b'R)-11'-(4-Methoxyphenyl)-9a',11b'-dimethyl-1',5a',6',6a',6b',7',8',9a',11a',11b'-decahydro-2'H,4'H-dispiro[[1,3]dioxolane-2,3'-cyclopenta[1,2]phenanthro[8a,9-b]oxirene-9',2"-[1,3]dioxolane]

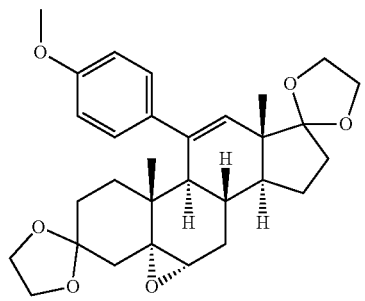

To a solution of (8'S,9'S,10'R,13'R,14'S)-11'-(4-methoxyphenyl)-10',13'-dimethyl-1',4',7',8',9',10',13',14',15',16'-decahydro-2'H-dispiro[[1,3]dioxolane-2,3'-cyclopenta[a]phenanthrene-17',2"-[1,3]dioxolane (Step C) (3.0 g, 1 eq) at 0° C. was added 1,1,1,3,3,3-hexafluoropropan-2-one (0.95 mL, 1.1 eq) followed by hydrogen peroxide solution (30%, 2.6 mL, 5 eq) and disodium phosphate (2.67 g, 3 eq). Stirring was continued at 0° for 10 min. The cooling bath was removed and the reaction was stirred at ambient temperature overnight. Additional aliquots of reagents (600 mg disodium phosphate, 0.3 mL CF$_3$COCF$_3$, 1 mL 30% H$_2$O$_2$) were added at 24 h and 48 h time points until TLC (2:1 hexanes:EtOAc) showed reaction completion.

The reaction was quenched with 10% Na$_2$S$_2$O$_3$ solution and extracted with EtOAc. After washing with brine, the organic layer was separated, dried with MgSO$_4$ and concentrated. The residue was purified by silica gel chromatography to provide 2.98 g (96%) of desired epoxide as a white foamy solid. m/z (ESI, +ve ion) 495.3 (M+H)$^+$.

STEP E. (5'R,8'S,9'R,10'R,13'R,14'S)-11'-(4-Methoxyphenyl)-10',13'-dimethyl-1',6',7',8',9',10',13',14',15',16'-decahydro-2'H-dispiro[[1,3]dioxolane-2,3'-cyclopenta[a]phenanthrene-17',2''-[1,3]dioxolan]-5'(4'H)-ol

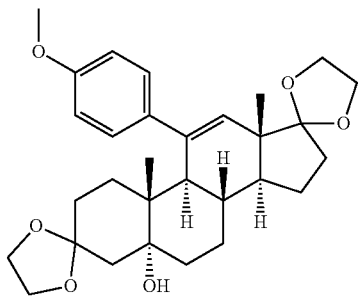

A flask was charged with (4a'R,5a'S,6a'S,6b'S,9a'R,11a'R,11b'R)-11'-(4-methoxyphenyl)-9a',11b'-dimethyl-1',5a',6',6a',6b',7',8',9a',11a',11b'-decahydro-2'H,4'H-dispiro[[1,3]dioxolane-2,3'-cyclopenta[1,2]phenanthro[8a,9-b]oxirene-9',2''-[1,3]dioxolane] (Step D) (2.98 g, 6.02 mmol, 1 eq) and azeotroped with toluene. Under argon, THF (30 mL) was added and the reaction was cooled in an ice-bath followed by dropwise addition of lithium aluminum hydride (1 M solution in THF, 6.02 mL, 1 eq). After 5 min, the ice bath was removed and the reaction was continued at rt for 1 h. The reaction was quenched with a few drops of methanol, followed by addition of sat. Rochelle's salt solution and EtOAc. The mixture was stirred for 15 min. Then the organic layer was separated, washed with brine, dried with MgSO₄ and concentrated. The residue was purified by silica gel chromatography to provide the title compound (2.63 g, 88%) as a white solid. m/z (ESI, +ve ion) 479.3 (M−OH)⁺.

STEP F. (3a'S,3b'S,5a'R,9a'R,9b'S,9c'R,10a'R,10b'R)-9c'-(4-Methoxyphenyl)-9a',10b'-dimethyldodecahydro-5'H-dispiro[[1,3]dioxolane-2,1'-cyclopenta[1,2]phenanthro[3,4-b]oxirene-7',2''-[1,3]dioxolan]-5a'(6'H)-ol

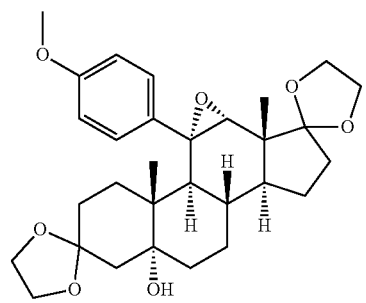

3-Chlorobenzenecarboperoxoic acid (75%, 3.57 g, 15.51 mmol, 4 eq) was added to a solution of (5'R,8'S,9'R,10'R,13'R,14'S)-11'-(4-methoxyphenyl)-10',13'-dimethyl-1',6',7',8',9',10',13',14',15',16'-decahydro-2'H-dispiro[[1,3]dioxolane-2,3'-cyclopenta[a]phenanthrene-17',2''-[1,3]dioxolan]-5'(4'H)-ol (Step E) (1.926 g, 3.88 mmol, 1 eq) in DCM (60 mL). The reaction was stirred for 20 h at rt. LCMS showed two peaks of the desired molecular weight. The reaction mixture was treated with sat. NaHCO₃ and extracted with EtOAc. The EtOAc layer was separated, washed with brine, dried over MgSO₄ and concentrated in vacuo. The residue was purified by silica gel chromatography to provide the more polar isomer (530 mg, 27%) as the desired product. The less polar isomer was also isolated (910 mg, 46%). Each isomer: m/z (ESI, +ve ion) 513.3 (M+H)⁺.

STEP G. (5'R,8'S,9'R,10'R,11'S,12'S,13'R,14'S)-11'-(4-Methoxyphenyl)-10',13'-dimethyldodecahydro-2'H-dispiro[[1,3]dioxolane-2,3'-cyclopenta[a]phenanthrene-17',2''-[1,3]dioxolane]-5',12'(4'H)-diol

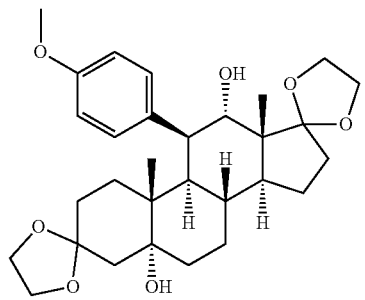

An oven-dried 3-necked 100 mL flask was equipped with a dry ice condenser cold finger, an argon balloon and a pressure relief needle. The cold finger was connected with an ammonia cylinder. Both the 3-necked flask and the cold finger were cooled with in dry ice in acetone. Liquid ammonia was condensed into the flask until the desired volume (~10 ml) was reached. The argon balloon was then switched to the cold finger joint.

An 8 mL THF solution of (3a'S,3b'S,5a'R,9a'R,9b'S,9c'R,10a'R,10b'R)-9c'-(4-methoxyphenyl)-9a',10b'-dimethyldodecahydro-5'H-dispiro[[1,3]dioxolane-2,1'-cyclopenta[1,2]phenanthro[3,4-b]oxirene-7',2''-[1,3]dioxolan]-5a'(6'H)-ol (Step F) (530.mg, 1.03 mmol, 1 eq) was added to the flask, followed by lithium wire (41.1 mg, 5.17 mmol, 5 eq). After about 5 min, a deep blue reaction color developed. The reaction was kept at −78° C. for 2 h. Ethanol (0.2 ml) was added and allowed to stir for about 2 min, then water was slowly added to quench the reaction. The bath was removed and ammonia allowed to evaporate. The reaction mixture was extracted with EtOAc. The organic layer was washed with brine, dried over MgSO₄ and concentrated in vacuo. The residue was purified by silica gel chromatography to give 385 mg of desired product (72%) as a white solid. m/z (ESI, +ve ion) 537.3 (M+Na)⁺.

STEP H. (8S,9R,10R,11S,12S,13R,14S)-12-hydroxy-11-(4-Methoxyphenyl)-10,13-dimethyl-1,6,7,8,9,10,11,12,13,14,15,16-dodecahydro-3H-cyclopenta[a]phenanthrene-3,17(2H)-dione

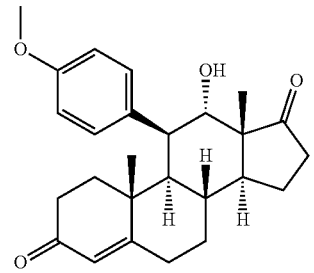

A flask was charged with (5'R,8'S,9'R,10'R,11'S,12'S, 13'R,14'S)-11'-(4-methoxyphenyl)-10',13'-dimethyldodecahydro-2'H-dispiro[[1,3]dioxolane-2,3'-cyclopenta[a]phenanthrene-17',2"-[1,3]dioxolane]-5',12'(4'H)-diol (Step G) (385 mg, 0.75 mmol, 1 eq) and acetone (7 mL) was added, followed by 4 N hydrogen chloride (0.37 mL, 1.5 mmol, 2 eq). The resulting clear mixture was stirred at rt for 3.5 h. The reaction was quenched with sat. NaHCO$_3$ and extracted with EtOAc. The EtOAc layer was washed with brine, dried over MgSO$_4$ and concentrated in vacuo. The residue was purified by silica gel chromatography to give 270 mg (88%) of desired product. m/z (ESI, +ve ion) 409.3 (M+H)$^+$.

STEP I. O-((8S,9R, 10R,11S,12S,13R,14S)-11-(4-Methoxyphenyl)-10,13-dimethyl-3,17-dioxo-2,3,6,7, 8,9,10,11,12,13,14,15,16,17-tetradecahydro-1H-cyclopenta[a]phenanthren-12-yl)1H-imidazole-1-carbothioate

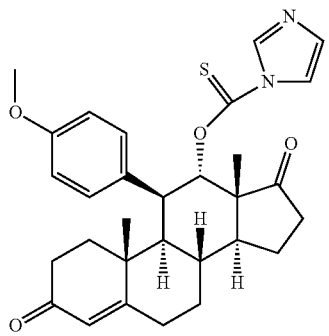

A flask was charged with (8S,10R,11S,12S,13R,14S)-12-hydroxy-11-(4-methoxyphenyl)-10,13-dimethyl-2,6,7,8,9, 11,12,14,15,16-decahydro-1H-cyclopenta[a]phenanthrene-3,17-dione (Step H) (270 mg, 0.66 mmol) and azeotroped with toluene. DCM (7 mL) was added, followed by triethylamine (0.28 mL, 1.98 mmol, 3 eq), and di(imidazol-1-yl)methanethione (1.18 g, 6.61 mmol, 10 eq). The reaction was stirred under argon at rt for one day, then another portion of di(imidazol-1-yl)methanethione (1.1 g) was added. After another day, another 700 mg of di(imidazol-1-yl)methanethione was added. The reaction was stirred for 2 more days. Then the reaction was quenched with diluted HCl (<1 N) and the crude was extracted with EtOAc. The organic layer was washed with brine twice, dried, and concentrated. The residue was purified by silica gel chromatography to give the title compound (265 mg, 77%). m/z (ESI, +ve ion) 541.3 (M+Na)$^+$.

STEP J. (8S,9R,10R,11S,13S,14S)-11-(4-Methoxyphenyl)-10,13-dimethyl-1,6,7,8,9,10,11,12,13,14,15, 16-dodecahydro-3H-cyclopenta[a]phenanthrene-3,17 (2H)-dione

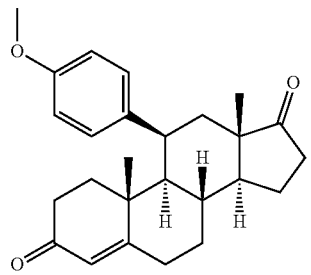

A flask was charged with O-((8S,9R,10R,11S,12S,13R, 14S)-11-(4-methoxyphenyl)-10,13-dimethyl-3,17-dioxo-2, 3,6,7,8,9,10,11,12,13,14,15,16,17-tetradecahydro-1H-cyclopenta[a]phenanthren-12-yl) 1H-imidazole-1-carbothioate (Step I) (265 mg, 0.51 mmol, 1 eq) and flushed with argon. Toluene (15 mL) was added followed by tributyltin hydride (0.3 mL, 1.12 mmol, 2.2 eq). The reaction was heated to reflux for 3 h, cooled, concentrated and purified by silica gel chromatography to give the title compound (168 mg, 84%) as a colorless oil. m/z (ESI, +ve ion) 393.4 (M+H)$^+$.

STEP K. (8S,9R,10R,11S,13S,14S)-11-(4-Methoxyphenyl)-10,13-dimethyl-1,6,7,8,9,10,11,12,13,14,15, 16-dodecahydrospiro[cyclopenta[a]phenanthrene-17, 2'-[1,3]dioxolan]-3(2H)-one

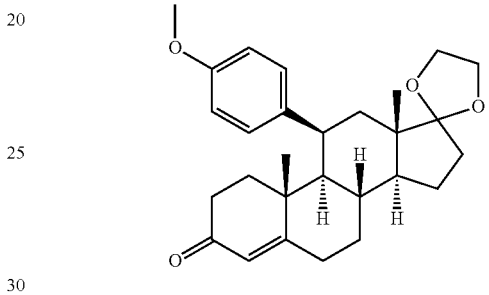

A solution of (8S,9R,10R,11S,13S,14S)-11-(4-methoxyphenyl)-10,13-dimethyl-1,6,7,8,9,10,11,12,13,14,15,16-dodecahydro-3H-cyclopenta[a]phenanthrene-3,17(2H)-dione (Step J) (44.5 mg, 0.11 mmol, 1 eq), in DCM (2mL), ethylene glycol (0.13 mL, 2.27 mmol, 20 eq), trimethyl orthoformate (0.07 mL, 0.62 mmol, 5.5 eq), and tosic acid monohydrate (2.16 mg, 0.01 mmol, 0.1 eq) was refluxed for 4 h, quenched with sat. NaHCO$_3$, and extracted with EtOAc. The EtOAc layer was washed with brine, dried and concentrated in vacuo. The residue was purified by silica gel chromatography to give the title compound (40 mg, 81%). m/z (ESI, +ve ion) 437.3 (M+H)$^+$.

STEP L. (8S,9R,10R,11S,13S,14S)-11-(4-Methoxyphenyl)-10,13-dimethyl-1,2,3,6,7,8,9,10,11,12,13,14, 15,16-tetradecahydrospiro[cyclopenta[a] phenanthrene-17,2'-[1,3]dioxolan]-3-ol

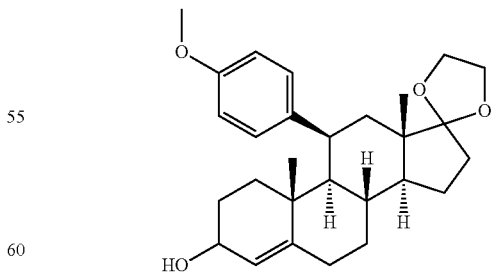

A solution of (8S,9R,10R,11S,13S,14S)-11-(4-methoxyphenyl)-10,13-dimethyl-1,6,7,8,9,10,11,12,13,14,15,16-dodecahydrospiro[cyclopenta[a]phenanthrene-17,2'-[1,3]dioxolan]-3(2H)-one (Step K) (31 mg, 0.07 mmol) in THF (2 mL) was cooled down in an ice-bath. A solution of lithium aluminum hydride (1M in THF, 0.14 mL, 0.14 mmol) was added and the reaction was continued at 0° C. for 30 min then 1 h at rt. The reaction was quenched with sat. Rochelle's salt solution. After stirring for 20 min, the reaction was extracted with EtOAc. The organic layer was washed with brine, dried and concentrated in vacuo. The residue was purified by silica gel chromatography to give the title compound (27 mg, 87%) of desired product. m/z (ESI, +ve ion) 421.4 (M−OH)$^+$.

STEP M. (3S,8S,9R,10R,11S,13S,14S)-3-Hydroxy-11-(4-methoxyphenyl)-10,13-dimethyl-1,2,3,6,7,8,9,10,11,12,13,14,15,16-tetradecahydro-17H-cyclopenta[a]phenanthren-17-one and (3R,8S,9R,10R,11S,13S,14S)-3-hydroxy-11-(4-methoxyphenyl)-10,13-dimethyl-1,2,3,6,7,8,9,10,11,12,13,14,15,16-tetradecahydro-17H-cyclopenta[a]phenanthren-17-one

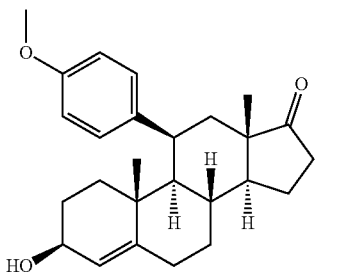

and

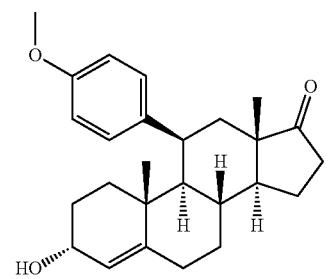

To a solution of (8S,9R,10R,11S,13S,14S)-11-(4-methoxyphenyl)-10,13-dimethyl-1,2,3,6,7,8,9,10,11,12,13,14,15,16-tetradecahydrospiro[cyclopenta[a]phenanthrene-17,2'-[1,3]dioxolan]-3-ol (Step L) (24 mg, 1 eq) in acetone (2 mL) was added hydrochloric acid (4N, 0.03 mL, 2 eq). The reaction mixture was stirred for 1.5 h at rt, quenched with sat. NaHCO$_3$. After extraction with EtOAc the organic layer was washed with brine, dried and concentrated in vacuo. The residue was purified by silica gel chromatography to give the more polar component as the major isomer (9 mg) (m/z (ESI, +ve ion) 377.3 (M−OH)$^+$) and the less polar component as the minor isomer (4.9 mg) (m/z (ESI, +ve ion) 377.3 (M−OH)$^+$).

STEP N. (3S,8S,9R,10R,11S,13S,14S,17S)-11-(4-Methoxyphenyl)-10,13-dimethyl-17-(prop-1-yn-1-yl)-2,3,6,7,8,9,10,11,12,13,14,15,16,17-tetradecahydro-1H-cyclopenta[a]phenanthrene-3,17-diol or (3R,8S,9R,10R,11S,13S,14S,17S)-11-(4-methoxyphenyl)-10,13-dimethyl-17-(prop-1-yn-1-yl)-2,3,6,7,8,9,10,11,12,13,14,15,16,17-tetradecahydro-1H-cyclopenta[a]phenanthrene-3,17-diol

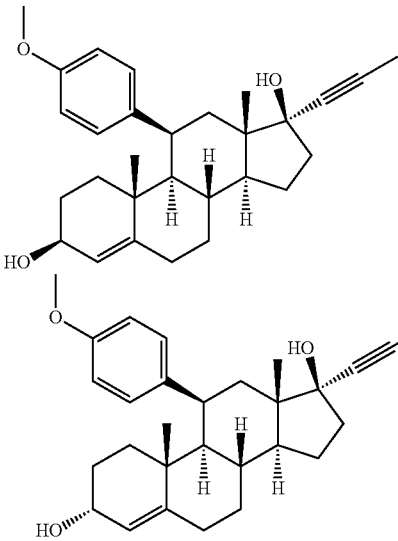

The major isomer (3S,8S,9R,10R,11S,13S,14S)-3-hydroxy-11-(4-methoxyphenyl)-10,13-dimethyl-1,2,3,6,7,8,9,10,11,12,13,14,15,16-tetradecahydro-17H-cyclopenta[a]phenanthren-17-one or (3R,8S,9R,10R,11S,13S,14S)-3-hydroxy-11-(4-methoxyphenyl)-10,13-dimethyl-1,2,3,6,7,8,9,10,11,12,13,14,15,16-tetradecahydro-17H-cyclopenta[a]phenanthren-17-one (Step M) (9 mg, 0.020 mmol, 1 eq) was azeotroped with toluene and flushed with argon and dissolved in THF (1 mL). The solution was cooled in an ice bath. Bromo(prop-1-ynyl)magnesium (0.5 M in THF, 0.23 mL, 0.11 mmol, 5 eq) was added and the reaction was continued in the ice bath for 10 min and then raised to rt. After 5.5 h, the reaction was quenched with sat. aq. NH$_4$Cl and extracted with EtOAc. The EtOAc layer was washed with brine, dried and concentrated in vacuo. The residue was purified by silica gel chromatography to give the title compound (5.3 mg, 53%) as a white solid. m/z (ESI, +ve ion) 417.3 (M−OH)$^+$.

STEP O. (8S,9R,10R,11S,13S,14S,17S)-17-Hydroxy-11-(4-methoxyphenyl)-10,13-dimethyl-17-(prop-1-yn-1-yl)-1,2,6,7,8,9,10,11,12,13,14,15,16,17-tetradecahydro-3H-cyclopenta[a]phenanthren-3-one

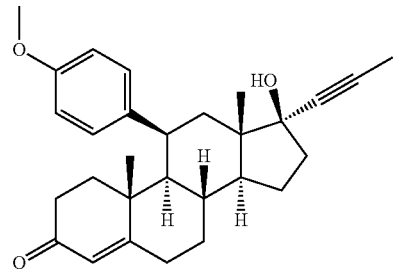

A flask was charged with (3S,8S,9R,10R,11S,13S,14S, 17S)-11-(4-methoxyphenyl)-10,13-dimethyl-17-(prop-1-yn-1-yl)-2,3,6,7,8,9,10,11,12,13,14,15,16,17-tetradecahydro-1H-cyclopenta[a]phenanthrene-3,17-diol or (3R,8S, 9R,10R,11S,13S,14S,17S)-11-(4-methoxyphenyl)-10,13-dimethyl-17-(prop-1-yn-1-yl)-2,3,6,7,8,9,10,11,12,13,14, 15,16,17-tetradecahydro-1H-cyclopenta[a]phenanthrene-3, 17-diol (Step N) (5 mg, 0.01 mmol, 1 eq). Manganese (IV) oxide (20 mg, 0.23 mmol, 20 eq) was added, followed by 2.2 mL DCM. The reaction was heated at 40° C. for 1 h and cooled down. Then the reaction was filtered through a pad of celite, rinsed with EtOAc, concentrated and directly purified by silica gel chromatography to give the title compound (3.4 mg, 68%) as a white solid. $^1$H NMR (400 MHz, CHLOROFORM-d) δ ppm 7.85 (br s, 2H), 6.75 (d, J=8.98 Hz, 2 H), 5.67 (d, J=0.98 Hz, 1 H), 3.79 (s, 3 H), 3.29-3.48 (m, 1 H), 2.46-2.65 (m, 1 H), 2.10-2.32 (m, 6 H), 1.90-1.95 (m, 2 H), 1.88 (s, 3 H), 1.71-1.77 (m, 2 H), 1.38-1.51 (m, 4 H), 1.14-1.21 (m, 2 H), 1.00 (s, 3 H), 0.84 (s, 3 H); m/z (ESI, +ve ion) 433.4 (M+H)$^+$.

Example 2

Compound 2. (8S,9R,10R,11S,13S,14S,17S)-11-(4-(Dimethylamino)phenyl)-17-hydroxy-10,13-dimethyl-17-(prop-1-yn-1-yl)-1,2,6,7,8,9,10,11,12,13,14, 15,16,17-tetradecahydro-3H-cyclopenta[a] phenanthren-3-one

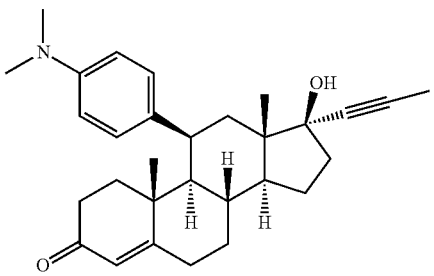

STEP A: tert-Butyl (4-((3a'S,3b'S,5a'R,9a'R,9b'S, 9c'R,10a'R,10b'R)-5a'-hydroxy-9a',10b'-dimethyltetradecahydro-9c'H-dispiro[[1,3]dioxolane-2,1'-cyclopenta[1,2]phenanthro[3,4-b]oxirene-7',2''-[1,3] dioxolane]-9c'-yl)phenyl)(methyl)carbamate

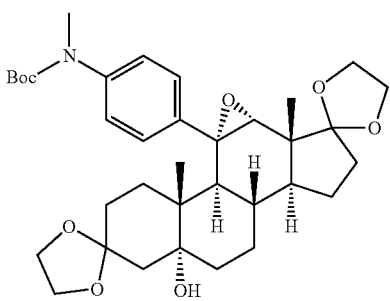

This title compound was prepared from (8'S,9'S,10'R, 13'R,14'S)-10',13'-Dimethyl-11'-(((4,4,4,4,4,4,4,4,4-nonafluoro-4l12-buta-1,3-diyn-1-yl)thio)trioxidanyl)-1',4',7',8', 9',10',13',14',15',16'-decahydro-2'H-dispiro[[1,3]dioxolane-2,3'-cyclopenta[a]phenanthrene-17',2''-[1,3]dioxolane] (Example 1, Step B) by procedures similar to those described in Example 1, Steps C-F, substituting (4-((tert-butoxycarbonyl)(methyl)amino)phenyl)boronic acid for 4-methoxyphenyl boronic acid in Step C.

STEP B: (5'R,8'S,9'R,10'R,11'S,12'S,13'R,14'S)-10', 13'-Dimethyl-11'-(4-(methylamino)phenyl)dodecahydro-2'H-dispiro[[1,3]dioxolane-2,3'-cyclopenta[a] phenanthrene-17',2''-[1,3]dioxolane]-5',12'(4'H)-diol

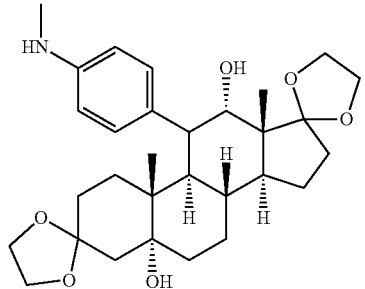

An oven-dried 3-necked 250 mL flask was fitted with a cold finger condenser and an argon balloon. Both the 3-necked flask and the cold finger were cooled with dry ice in acetone. Liquid ammonia from a supply tank was condensed into the flask until the desired volume of 25 mL was reached. Lithium metal (109 mg, 13.7 mmol) was added and the solution changed to a dark blue color. The dry ice bath was removed briefly for 2 min to speed up the dissolving process of lithium, then the flask was returned to the cooling bath. After about 4 min, a solution of tert-butyl (4-((3a'S, 3b'S,5a'R,9a'R,9b'S,9c'R,10a'R,10b'R)-5a'-hydroxy-9a', 10b'-dimethyltetradecahydro-9c'H-dispiro[[1,3]dioxolane-2,1'-cyclopenta[1,2]phenanthro[3,4-b]oxirene-7',2''-[1,3] dioxolane]-9c'-yl)phenyl)(methyl)carbamate (1.05 g, 1.72 mmol) (Example 2, Step A) in THF (20 ml) was added dropwise over about 5 min. The reaction was continued for 50 min and its color remained dark blue. At this point, 0.5 mL of ethanol was added, stirred for 1 min, then the cooling bath was removed and water was added slowly to quench the reaction. EtOAc was added and ammonia was allowed to evaporate. The reaction mixture was extracted with EtOAc and washed with brine. The organic layer was dried, concentrated and the residue was purified on a 40 g Redi-Sep silica gel column to give 715 mg of desired product (81%). m/z (ESI, +ve ion) 514.4 (M+H)$^+$.

STEP C. (5'R,8'S,9'R,10'R,11'S,12'S,13'R,14'S)-11'-(4-(Dimethylamino)phenyl)-10',13'-dimethyldodecahydro-2'H-dispiro[[1,3]dioxolane-2,3'-cyclopenta[a] phenanthrene-17',2''-[1,3]dioxolane]-5',12'(4'H)-diol

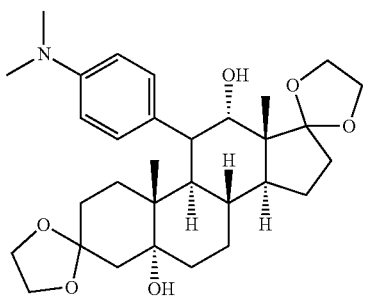

A flask was charged with (5'R,8'S,9'R,10'R,11'S,12'S,13'R,14'S)-10',13'-dimethyl-11'-(4-(methylamino)phenyl)dodecahydro-2'H-dispiro[[1,3]dioxolane-2,3'-cyclopenta[a]phenanthrene-17',2''-[1,3]dioxolane]-5',12'(4'H)-diol (609 mg, 1.19 mmol) (Example 2, Step B) and DCM (12 mL) was added, followed by acetic acid (0.68 mL, 11.86 mmol). Then formaldehyde (0.45 mL, 5.93 mmol) was added and the mixture was stirred for 6 min. Sodium triacetoxyborohydride (276.4 mg, 1.3 mmol) was added. The reaction was stirred for 1 h and quenched with saturated NaHCO$_3$ and extracted with EtOAc. The organic layer was dried, concentrated and purified on a 40 g Redi-Sep silica column to give 575 mg of the title compound (92%). m/z (ESI, +ve ion) 528.3 (M+H)$^+$.

STEP D. (8S,9R,10R,11S,12S,13R,14S)-11-(4-(Dimethylamino)phenyl)-12-hydroxy-10,13-dimethyl-1,6,7,8,9,10,11,12,13,14,15,16-dodecahydro-3H-cyclopenta[a]phenanthrene-3,17(2H)-dione

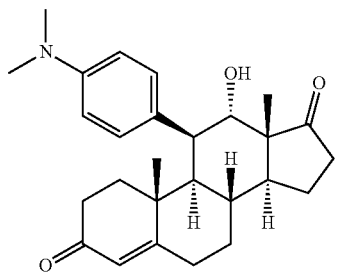

The title compound was prepared from (5'R,8'S,9'R,10'R,11'S,12'S,13'R,14'S)-11'-(4-(dimethylamino)phenyl)-10',13'-dimethyldodecahydro-2'H-dispiro[[1,3]dioxolane-2,3'-cyclopenta[a]phenanthrene-17',2''-[1,3]dioxolane]-5',12'(4'H)-diol (Example 2, Step C) by a procedure similar to that described in Example 1, Step H. m/z (ESI, +ve ion) 422.3 (M+H)$^+$.

STEP E. (8S,9R,10R,11S,13S,14S)-11-(4-(Dimethylamino)phenyl)-10,13-dimethyl-1,6,7,8,9,10,11,12,13,14,15,16-dodecahydro-3H-cyclopenta[a]phenanthrene-3,17(2H)-dione

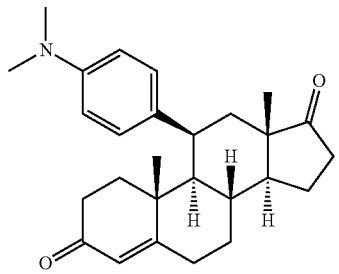

The title compound was prepared from (8S,9R,10R,11S,12S,13R,14S)-11-(4-(dimethylamino)phenyl)-12-hydroxy-10,13-dimethyl-1,6,7,8,9,10,11,12,13,14,15,16-dodecahydro-3H-cyclopenta[a]phenanthrene-3,17(2H)-dione (Step D) by a procedure similar to that described in Example 1, Steps I and J. m/z (ESI, +ve ion) 406.4 (M+H)$^+$.

STEP F. (8S,9R,10R,11S,13S,14S)-11-(4-(Dimethylamino)phenyl)-3-ethoxy-10,13-dimethyl-1,2,7,8,9,10,11,12,13,14,15,16-dodecahydro-17H-cyclopenta[a]phenanthren-17-one

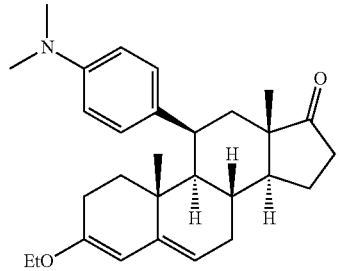

A flask was charged with (8S,9R,10R,11S,13S,14S)-11-(4-(dimethylamino)phenyl)-10,13-dimethyl-1,6,7,8,9,10,11,12,13,14,15,16-dodecahydro-3H-cyclopenta[a]phenanthrene-3,17(2H)-dione (210.mg, 0.52 mmol) (Example 2, Step E) and azeotroped with toluene. p-Toluenesulfonic acid monohydrate (118.2 mg, 0.62 mmol) was added to the flask and the flask was flushed with Argon. Ethanol (8 mL) was added, and the reaction was cooled in an ice-bath. Triethyl orthoformate (0.26 mL, 1.55 mmol) was added. The reaction was stirred in the ice-bath for 1 h. Triethylamine (0.72 mL) was added to neutralize the acid. The reaction was concentrated and then directly purified on a 24 g Redi-Sep silica gel column to give 66 mg of desired mono-ketone (29%). The remaining over-protected and alternate mono-protected products were recycled through hydrolysis with HCl as in Step D. m/z (ESI, +ve ion) 434.4 (M+H)$^+$.

STEP G. (8S,9R,10R,11S,13S,14S,17S)-11-(4-(Dimethylamino)phenyl)-17-hydroxy-10,13-dimethyl-17-(prop-1-yn-1-yl)-1,2,6,7,8,9,10,11,12,13,14,15,16,17-tetradecahydro-3H-cyclopenta[a]phenanthren-3-one

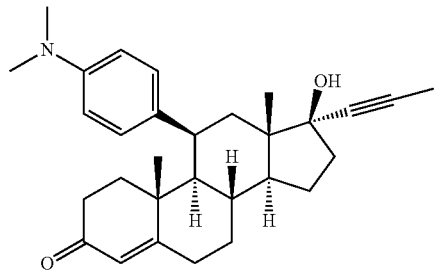

A flask was charged with (8S,9R,10R,11S,13S,14S)-11-(4-(dimethylamino)phenyl)-3-ethoxy-10,13-dimethyl-1,2,7,8,9,10,11,12,13,14,15,16-dodecahydro-17H-cyclopenta[a]phenanthren-17-one (Example 2, Step F), azeotroped with toluene and flushed with argon. THF (3 mL) was added. The reaction was cooled in an ice-bath, then bromo(prop-1-ynyl)magnesium (0.5M in THF, 2.44 mL, 1.22 mmol) was added. The bath was removed and the reaction was stirred at rt overnight. Then the reaction was quenched with saturated NH$_4$Cl and extracted with EtOAc. The organic layer was dried, filtered and concentrated. The residue was treated with 1.5 mL THF, 1.2 mL water, 0.75 mL 4N HCl. at rt for 1 h. Saturated NaHCO$_3$ solution was added and the mixture extracted with EtOAc. The organic layer was concentrated and purified in 2 batches on reverse phase HPLC to give 75 mg of title compound as the TFA salt (75%). m/z (ESI, +ve ion) 446.3 (M+H)⁺. ¹H NMR (400 MHz, CHLOROFORM-d) δ ppm 7.50-7.81 (br s, 2 H), 7.43 (d, J=8.92 Hz, 2 H), 5.72 (d, J=1.02 Hz, 1 H), 3.57 (br t, J=5.77 Hz, 1 H), 3.20 (s, 6 H), 2.52 (td, J=13.74, 4.24 Hz, 1 H), 2.15-2.41 (m, 7 H), 1.90-2.01 (m, 3 H), 1.90 (s, 3 H), 1.71-1.83 (m, 2 H), 1.37-1.62 (m, 3 H), 1.13-1.28 (m, 1 H), 1.01 (s, 3 H), 0.76, (s, 3 H).

Examples 3-8 were prepared from (8'S,9'S,10'R,13'R,14'S)-10',13'-dimethyl-11'-(((4,4,4,4,4,4,4,4,4-nonafluoro-4l12-buta-1,3-diyn-1-yl)thio)trioxidanyl)-1',4',7',8',9',10',13',14',15',16'-decahydro-2'H-dispiro[[1,3]dioxolane-2,3'-cyclopenta[a]phenanthrene-17',2''-[1,3]dioxolane] (Example 1, Step B) by procedures similar to those described in Example 1, Steps C-F, substituting 4-methoxyphenyl boronic acid with the appropriate boronic acid in Step C, and followed by procedures similar to those described in Example 2, Steps B-G, substituting bromo(prop-1-ynyl)magnesium with the appropriate alkynylmagnesium bromide in Step G.

Example 3

Compound 12. (8S,9R,10R,11S,13S,14S,17S)-17-(cyclopropylethynyl)-11-(4-(dimethylamino)phenyl)-17-hydroxy-10,13-dimethyl-1,2,6,7,8,9,10,11,12,13,14,15,16,17-tetradecahydro-3H-cyclopenta[a]phenanthren-3-one

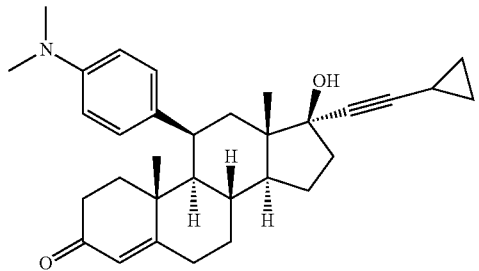

¹H NMR (400 MHz, CHLOROFORM-d) δ ppm 7.14-7.27 (br s, 2 H), 6.52 (br d, J=8.33 Hz, 2 H), 5.61 (d, J=1.32 Hz, 1 H), 3.22-3.41 (m, 1 H), 2.86 (s, 6 H), 2.39-2.46 (m, 1H), 2.00-2.26 (m, 7 H), 1.77-1.92 (m, 3 H), 1.58-1.72 (m, 2 H), 1.52-1.56 (m, 1 H), 1.33-1.44 (m, 2 H), 1.18-1.25 (m, 1 H), 1.06-1.13 (m, 1 H), 0.94 (s, 3H), 0.79 (s, 3H), 0.68-0.75 (m, 2H), 0.57-0.63 (m, 2 H); m/z (ESI, +ve ion)=472.4 [M+H]⁺.

Example 4

Compound 13. (8S,10R,11S,13S,14S,17S)-11-(4-(Dimethylamino)phenyl)-17-hydroxy-10,13-dimethyl-17-(3-methylbut-1-yn-1-yl)-1,2,6,7,8,9,10,11,12,13,14,15,16,17-tetradecahydro-3H-cyclopenta[a]phenanthren-3-one

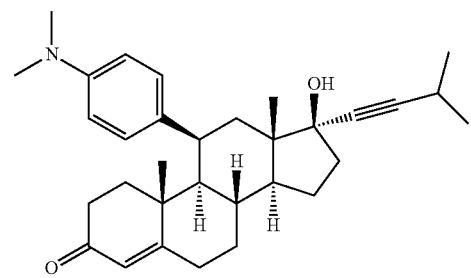

¹H NMR (400 MHz, CHLOROFORM-d) δ ppm 7.27 (2 H, m), 6.61 (2 H, br dd, J=6.80, 1.24 Hz), 5.68 (1 H, d, J=1.32 Hz),4.86-4.99 (1 H, m), 3.41 (1 H, m), 3.40 (1 H, s) 2.94 (6 H, s), 2.59-2.63 (1 H, m), 2.25-2.30 (4 H, m), 2.11-2.20 (2 H, m), 1.90-2.05 (3 H, m), 1.52-1.78 (4 H, m), 1.36-1.52 (3 H, m), 1.26 (3 H, s), 1.19 (3 H, s), 1.17 (3 H, s), 1.02 (3 H, s), 0.88 (3 H, m); m/z (ESI, +ve ion)=474.4 [M+H]⁺.

Example 5

Compound 14. (8S,10R,11S,13S,14S,17S)-17-(But-1-yn-1-yl)-11-(4-(dimethylamino)phenyl)-17-hydroxy-10,13-dimethyl-1,2,6,7,8,9,10,11,12,13,14,15,16,17-tetradecahydro-3H-cyclopenta[a]phenanthren-3-one

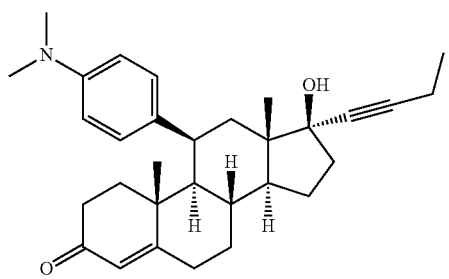

¹H NMR (400 MHz, CHLOROFORM-d) δ ppm 7.33-7.45 (2 H, br s), 6.61 (2 H, br dd, J=7.02, 1.46 Hz), 5.68 (1 H, d, J=1.17 Hz), 3.42 (1 H, m), 2.94 (6 H, s), 2.41-2.65 (2 H, m), 2.10-2.34 (7 H, m), 1.82-2.05 (4 H, m), 1.69-1.80 (2 H, m), 1.44-1.53 (3 H, m), 1.41 (1 H, s), 1.26 (3 H, s), 1.09-1.20 (3 H, m), 1.02 (3 H, s), 0.80-1.07 (3 H, m); m/z (ESI, +ve ion)=460.4 [M+H]⁺.

Example 6

Compound 15. (8S,9R,10R,11S,13S,14S,17S)-17-Hydroxy-11-(4-((2-methoxyethyl)(methyl)amino)phenyl)-10,13-dimethyl-17-(prop-1-yn-1-yl)-1,2,6,7,8,9,10,11,12,13,14,15,16,17-tetradecahydro-3H-cyclopenta[a]phenanthren-3-one

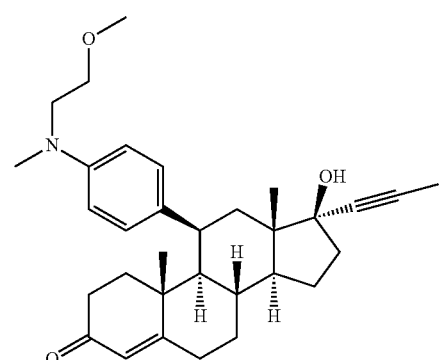

Formaldehyde in Example 2, Step C was replaced with 2-methoxyacetaldehyde, which was prepared from 2-methoxyethan-1-ol via Swern oxidation.

¹H NMR of its TFA salt (400 MHz, CHLOROFORM-d) δ ppm 7.54 (br s, 2 H), 7.29-7.34 (m, 2 H), 5.73 (m, 1 H), 3.43-3.67 (m, 5 H), 3.27 (s, 3 H), 3.23 (br s, 3 H), 2.38-2.56 (m, 1 H), 2.15-2.41 (m, 7H), 1.85-2.01 (m, 3 H), 1.90 (s, 3 H), 1.72-1.84 (m, 2 H), 1.47-1.58 (m, 3 H), 1.12-1.25 (m, 1 H), 1.02 (s, 3 H), 0.78 (s, 3H); m/z (ESI, +ve ion)=490.4 [M+H]⁺.

Example 7

Compound 16. (8S,9R,10R,11S,13S,14S,17S)-17-Hydroxy-10,13-dimethyl-17-(prop-1-yn-1-yl)-11-(4-(pyrrolidin-1-yl)phenyl)-1,2,6,7,8,9,10,11,12,13,14,15,16,17-tetradecahydro-3H-cyclopenta[a]phenanthren-3-one

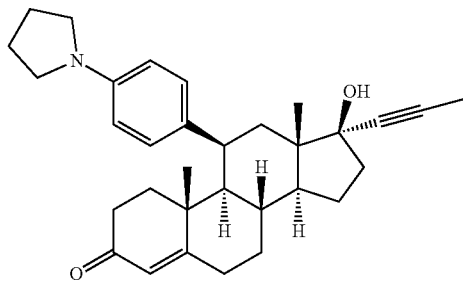

4-Methoxyphenyl boronic acid was replaced with (4-((tert-butoxycarbonyl)amino)phenyl)boronic acid in Example 1, Step C and formaldehyde was replaced with 2,5-dimethoxytetrahydrofuran in Example 2, Step C.

¹H NMR of its TFA salt (400 MHz, CHLOROFORM-d) δ ppm 7.35-7.46 (br s, 2 H), 7.05 (d, J=8.62 Hz, 2 H), 5.72 (d, J=1.17 Hz, 1 H), 3.58 (br t, J=6.65 Hz, 4 H), 3.38-3.54 (m, 1 H), 2.45-2.53 (m, 1 H), 2.15-2.35 (m, 14 H), 1.87-2.0 (m, 1 H), 1.90 (s, 3H), 1.70-1.82 (m, 2 H) 1.37-1.60 (m, 2 H), 1.10-1.25 (m, 1 H), 1.02 (s, 3 H), 0.82 (s, 3 H); m/z (ESI, +ve ion)=472.4 [M+H]⁺.

Example 8

Compound 11. (8S,10R,11S,13S,14S,17S)-11-(4-(Dimethylamino)phenyl)-17-(3,3-dimethylbut-1-yn-1-yl)-17-hydroxy-10,13-dimethyl-1,2,6,7,8,9,10,11,12,13,14,15,16,17-tetradecahydro-3H-cyclopenta[a]phenanthren-3-one

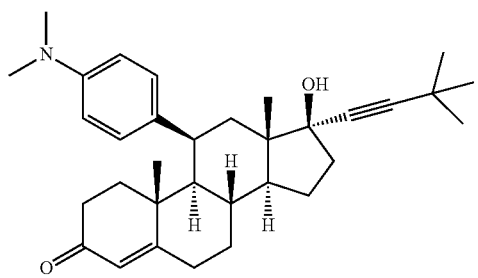

¹H NMR (400 MHz, CHLOROFORM-d) δ ppm 7.15-7.35 (2 H, m), 6.61 (2 H, br d, J=7.75 Hz), 5.64-5.70 (1 H, s), 3.41 (1 H, br t, J=5.48 Hz), 2.93 (6 H, s), 2.22-2.36 (5 H, m), 2.10-2.22 (2 H, m), 1.83-2.05 (4 H, m), 1.67-1.79 (3 H, m), 1.36-1.64 (2 H, m), 1.42-1.52 (2 H, m), 1.20 (6 H, m), 1.10 (3 H, s), 0.88 (3 H, s); m/z (ESI, +ve ion)=488.5 [M+H]⁺.

Example 9

Compound 7. (8R,9S,10R,11S,13S,14S,17S)-11-(4-(dimethylamino)phenyl)-17-(3,3-dimethylbut-1-yn-1-yl)-17-hydroxy-13-methyl-1,2,6,7,8,9,10,11,12,13,14,15,16,17-tetradecahydro-3H-cyclopenta[a]phenanthren-3-one

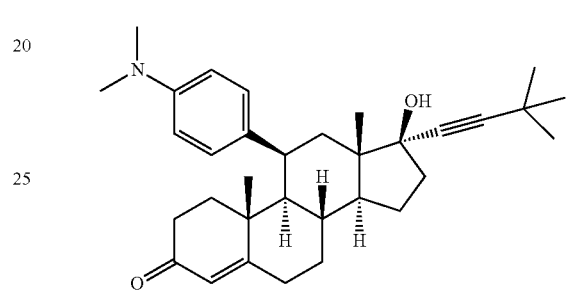

STEP A. (8S,13S,14S)-13-Methyl-1,2,4,6,7,8,12,13,14,15,16,17-dodecahydrospiro[cyclopenta[a]phenanthrene-3,2'-[1,3]dioxolan]-17-ol

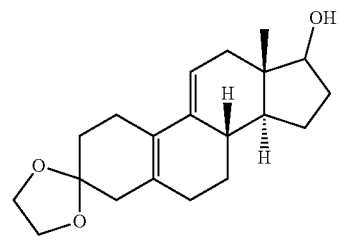

To a solution of (8S,13S,14S)-13-methyl-1,4,6,7,8,12,13,14,15,16-decahydrospiro[cyclopenta[a]phenanthrene-3,2'-[1,3]dioxolan]-17(2H)-one (100 g, 318 mmol) in THF (500 mL) and MeOH (50 mL) was added sodium borohydride (6.14 g, 159 mmol) in portions at 0° C. The mixture was stirred at 0° C. for 30 min and then rt for 1 h. After the TLC showed that the starting material disappeared, the reaction was quenched with 2 mL of sat. NaHCO₃ solution and concentrated to remove MeOH. The residue was dissolved in EtOAc, the organic phase was washed with sat. NaHCO₃ solution, brine, dried over anhydrous Na₂SO₄, and concentrated under reduced pressure to give the title compound (99.5 g, 100% yield) as a colorless oil. The crude material was used for next reaction without further purification. m/z (ESI, +ve ion)=317.3 [M+H]⁺.

STEP B. (5'R,8'S,10'R,13'S,14'S)-13'-Methyl-1',2',7', 8',12',13',14',15',16',17'-decahydro-4'H,6'H-spiro[[1, 3]dioxolane-2,3'-[5,10]epoxycyclopenta[a] phenanthren]-17'-ol

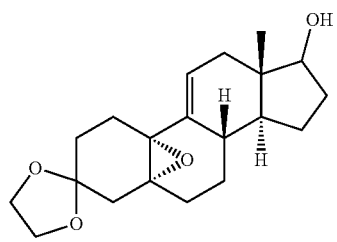

To a solution of (8S,13S,14S)-13-methyl-1,2,4,6,7,8,12, 13,14,15,16,17-dodecahydrospiro[cyclopenta[a] phenanthrene-3,2'-[1,3]dioxolan]-17-ol (43.0 g, 136 mmol, Step A) in DCM (320 mL) at 0° C. was added Na$_2$HPO$_4$ (9.65 g, 68.0 mmol), followed by 1,1,1,3,3,3-hexafluoropropan-2-one trihydrate (11.2 mL, 81.5 mmol) and H$_2$O$_2$ (35% aqueous solution, 34.2 mL, 408 mmol). The mixture was stirred at 0° C. for 10 min and then at rt for 3 h. 10% Sodium thiosulfate solution (200 mL) was slowly added at 0° C. and the mixture was stirred at rt for 30 min and extracted with DCM (300 mL). The organic phase was washed with brine, dried over anhydrous Na$_2$SO$_4$, and concentrated to provide the title compound (43.0 g) as a 4:1 mixture of epoxides as a white solid. The crude material was used for next step without further purification.

STEP C. (8S,11R,13S,14S)-11-(4-(dimethylamino) phenyl)-17-hydroxy-13-methyl-1,2,6,7,8,11,12,13, 14,15,16,17-dodecahydro-3H-cyclopenta[a] phenanthren-3-one

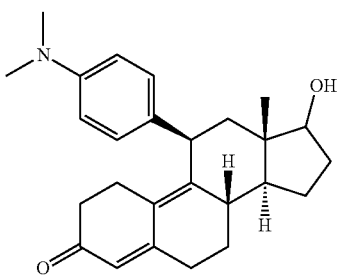

[4-(Dimethylamino)phenyl]magnesium bromide (96.3 mL, 0.5M in THF, 48.1 mmol) was added to a solution of (5'R,8'S,10'R,13'S,14'S)-13'-methyl-1',2', 7',8',12',13',14',15',16',17'-decahydro-4'H,6'H-spiro[[1,3]dioxolane-2,3'-[5,10]epoxycyclopenta[a]phenanthren]-17'-ol (4 g, 12.1 mmol, azeotroped with toluene, Step B) and copper(I) iodide (2.23 g, 12.1 mmol) in THF (35 mL) at 0° C. The resulting mixture was allowed to warm up to rt and stir for 1 h. The reaction was quenched (sat. aq. NH$_4$Cl), extracted (2×EtOAc), and washed (brine). The combined organic layer was dried (Na$_2$SO$_4$) and concentrated under reduced pressure. Purification of the residue by combi-flash (220 g SiO$_2$, 20% to 80% EtOAc/hexane) provided (5R,8S, 11R,13S,14S)-11-(4-(dimethylamino)phenyl)-13-methyl-1, 2,6,7,8,11,12,13,14,15,16,17-dodecahydrospiro[cyclopenta [a]phenanthrene-3,2'-[1,3]dioxolane]-5,17(4H)-diol (4 g, 8.8 mmol, 73% yield) as an off-white foam.

A solution of (5R,8S,11R,13S,14S)-11-(4-(dimethylamino)phenyl)-13-methyl-1,2,6,7,8,11,12,13,14,15,16,17-dodecahydrospiro[cyclopenta[a]phenanthrene-3,2'-[1,3]dioxolane]-5,17(4H)-diol (4 g, 8.8 mmol) in 70% acetic acid in water (5 mL, 893 mmol) was stirred at 55° C. for 1 h. The reaction was concentrated under reduced pressure to remove most of AcOH. Then the residue was diluted (EtOAc), basified (sat. aq. NaHCO$_3$), extracted (2×EtOAc), and washed (brine). The combined organic layer was dried (Na$_2$SO$_4$), and concentrated under reduced pressure. Purification of the residue by combi-flash (220 g SiO$_2$, 20% to 60% EtOAc/hexane) gave the title compound (2.3 g, 5.9 mmol, 67% yield) as a white solid.

STEP D. (8S,9R,11S,13S,14S)-11-(4-(dimethylamino)phenyl)-17-hydroxy-13-methyl-1,2,4,6,7,8,9, 11,12,13,14,15,16,17-tetradecahydro-3H-cyclopenta [a]phenanthren-3-one

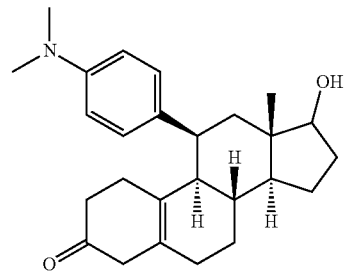

Under Ar, lithium (72 mg, 10.3 mmol) in pieces was added to distilled liquid ammonia (40 mL) and the slurry was stirred at ammonia reflux for 25 min (as soon as Li was added, color changed to dark purple). The Li/NH3 mixture was chilled to −78° C. and THF (13 mL) was added. Then a solution of (8S,11R,13S,14S)-11-(4-(dimethylamino)phenyl)-17-hydroxy-13-methyl-1,2,6,7,8,11,12,13,14,15,16,17-dodecahydro-3H-cyclopenta[a]phenanthren-3-one (1.00 g, 2.56 mmol) (Step C) and tert-butanol (0.59 mL, 6.16 mmol) in THF (30 mL) was added over 4 min (After the starting material was completely added, color changed from dark purple to light purple). The mixture was stirred at −78° C. for 4 min before the reaction was quenched by adding solid ammonium chloride (2.88 g, 53.8 mmol) (as soon as NH$_4$Cl was added, light purple color faded away immediately). Then the reaction was stirred at −78° C. for 10 min. Then both dry ice bath and cold finger condenser were removed and ammonia was allowed to be evaporated by N$_2$ stream while the slurry was stirred at RT. The residue was diluted (saturated aq. NH$_4$Cl) and extracted (2×EtOAc). The combined organic layer was washed (brine), dried (Na$_2$SO$_4$), and concentrated under reduced pressure. Purification of the residue by silica-gel column chromatography (80 g SiO$_2$, 45% to 60% EtOAc/hex) provided (8S,9R,11S,13S,14S)-11-(4-(dimethylamino)phenyl)-17-hydroxy-13-methyl-1,2,4,6, 7,8,9,11,12,13,14,15,16,17-tetradecahydro-3H-cyclopenta [a]phenanthren-3-one (3.73 g, 9.49 mmol, 74% yield) as a white solid. m/z (ESI, +ve ion)=394.3 [M+H]+.

STEP E. (8R,9S,10R,11S,13S,14S)-11-(4-(dimethyl-amino)phenyl)-17-hydroxy-13-methyl-1,2,6,7,8,9,10,11,12,13,14,15,16,17-tetradecahydro-3H-cyclopenta[a]phenanthren-3-one

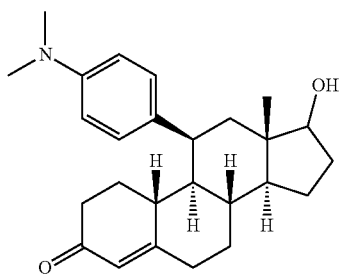

To a solution of (8S,9R,11S,13S,14S)-11-[4-(dimethyl-amino)phenyl]-17-hydroxy-13-methyl-2,4,6,7,8,9,11,12,14,15,16,17-dodecahydro-1H-cyclopenta[a]phenanthren-3-one (348 mg, 0.880 mmol) (Step D) in benzene (19 mL) was added 4-methylbenzenesulfonic acid hydrate (505 mg, 2.65 mmol) and the resulting solution was refluxed under Ar for 24 h. The reaction was cooled to room temperature and quenched by a few drops of TEA. The reaction was diluted (EtOAc and sat. aq. NaHCO₃) and extracted (2×EtOAc). The combined organic layer was washed (brine), dried (Na₂SO₄), and concentrated under reduced pressure. Purification of the residue by silica-gel column chromatography (40 g SiO₂, 30% to 80% EtOAc/hex) provided (8R,9S,10R,11S,13S,14S)-11-[4-(dimethylamino)phenyl]-17-hydroxy-13-methyl-2,6,7,8,9,10,11,12,14,15,16,17-dodecahydro-1H-cyclopenta[a]phenanthren-3-one (145 mg, 0.368 mmol, 42% yield) as a white foam. m/z (ESI, +ve ion)=394.3 [M+H]+.

STEP F. (8R,9S,10R,11S,13S,14S)-11-(4-(dimethyl-amino)phenyl)-13-methyl-1,2,6,7,8,9,10,11,12,13,14,15,16,17-tetradecahydrospiro[cyclopenta[a]phenanthrene-3,2'-[1,3]dithiolan]-17-ol

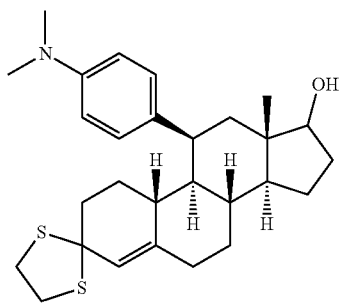

To a solution of (8R,9S,10R,11S,13S,14S)-11-[4-(dimethylamino)phenyl]-17-hydroxy-13-methyl-2,6,7,8,9,10,11,12,14,15,16,17-dodecahydro-1H-cyclopenta[a]phenanthren-3-one (51 mg, 0.13 mmol) (Step E) and ethane-1,2-dithiol (109 uL, 1.3 mmol) in acetic acid (1.08 mL) was added 4-methylbenzenesulfonic acid hydrate (49.3 mg, 0.260 mmol) and the resulting solution was stirred at room temperature for 1.5 h under Ar. The reaction was quenched (ice-cold 2 N aq. NaOH) and extracted (2×EtOAc). The combined organic layer was washed (brine), dried (MgSO₄), and concentrated under reduced pressure. Purification of the residue by silica-gel column chromatography (12 g SiO₂, 0% to 40% EtOAc/hex) provided the title compound (37 mg, 0.079 mmol, 61% yield) as a white solid. m/z (ESI, +ve ion)=470.3 [M+H]+.

STEP G. (8R,9S,10R,11S,13S,14S)-11-(4-(dimethylamino)phenyl)-13-methyl-1,6,7,8,9,10,11,12,13,14,15,16-dodecahydrospiro[cyclopenta[a]phenanthrene-3,2'-[1,3]dithiolan]-17(2H)-one

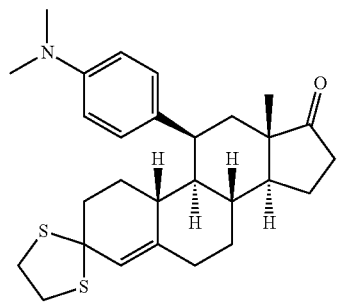

To a solution of (8R,9S,10R,11S,13S,14S)-11-(4-(dimethylamino)phenyl)-13-methyl-1,2,6,7,8,9,10,11,12,13,14,15,16,17-tetradecahydrospiro[cyclopenta[a]phenanthrene-3,2'-[1,3]dithiolan]-17-ol (37 mg, 0.080 mmol) (Step F) in toluene (1.6 mL) was added cyclohexanone (114 uL, 1.10 mmol) and aluminum propan-2-olate (113 mg, 0.55 mmol) successively. The reaction was heated to 105° C. for 4 h and cooled to room temperature. The reaction was quenched by adding saturated aqueous Rochelle's salt solution and the mixture was stirred for 10 min. Then the reaction was extracted (2×EtOAc). The combined organic layer was washed (brine), dried (MgSO₄), and concentrated under reduced pressure. Purification of the residue by silica-gel column chromatograph (12 g SiO₂, 0% to 30% EtOAc/hex) provided (8R,9S,10R,11S,13S,14S)-11-[4-(dimethylamino) phenyl]-13-methyl-spiro[1,2,6,7,8,9,10,11,12,14,15,16-dodecahydrocyclopenta[a]phenanthrene-3,2'-1,3-dithiolane]-17-one (25 mg, 0.053 mmol, 67% yield) as a colorless form. m/z (ESI, +ve ion)=468.3 [M+H]+.

STEP H. (8R,9S,10R,11S,13S,14S,17S)-11-(4-(dimethylamino)phenyl)-17-(3,3-dimethylbut-1-yn-1-yl)-13-methyl-1,2,6,7,8,9,10,11,12,13,14,15,16,17-tetradecahydrospiro[cyclopenta[a]phenanthrene-3,2'-[1,3]dithiolan]-17-ol

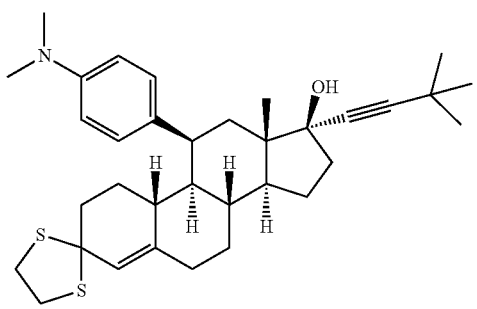

3,3-Dimethylbut-1-yne (84 uL, 0.69 mmol) was added to a solution of butyllithium (1.6M in hexanes, 0.30 mL, 0.48 mmol) in THF (0.5 mL) at −78° C. After 10 min, a solution of (8R,9S,10R,11S,13S,14S)-11-[4-(dimethylamino)phenyl]-13-methyl-spiro[1,2,6,7,8,9,10,11,12,14,15,16-dodecahydrocyclopenta[a]phenanthrene-3,2'-1,3-dithiolane]-17-one (25 mg, 0.050 mmol) (Step G) in THF (0.5 mL) was added slowly. After an additional 2 h at −78° C., the reaction was quenched (sat. aq. NH$_4$Cl) and extracted (2×EtOAc). The combined organic layers were washed (brine), dried (MgSO$_4$), and concentrated under reduced pressure. Purification of the residue by combi-flash (12 g SiO$_2$, 10% to 25% EtOAc/hexanes) provided (8R,9S,10R,11S,13S,14 S,17S)-11-[4-(dimethylamino)phenyl]-17-(3,3-dimethylbut-1-ynyl)-13-methyl-spiro[1,2,6,7,8,9,10,11,12,14,15,16-dodecahydrocyclopenta[a]phenanthrene-3,2'-1,3-dithiolane]-17-ol (17 mg, 0.031 mmol, 58% yield) as a colorless film. m/z (ESI, +ve ion)=550.4 [M+H]+.

STEP I. (8R,9S,10R,11S,13S,14S,17S)-11-(4-(dimethylamino)phenyl)-17-(3,3-dimethylbut-1-yn-1-yl)-17-hydroxy-13-methyl-1,2,6,7,8,9,10,11,12,13,14, 15,16,17-tetradecahydro-3H-cyclopenta[a]phenanthren-3-one

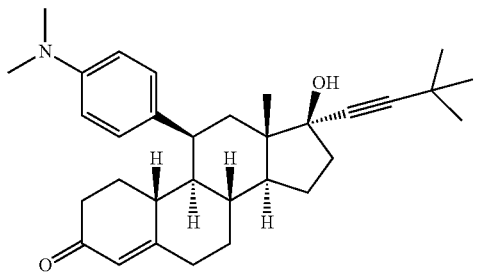

To a solution of (8R,9S,10R,11S,13S,14S,17S)-11-[4-(dimethylamino)phenyl]-17-(3,3-dimethylbut-1-ynyl)-13-methyl-spiro[1,2,6,7,8,9,10,11,12,14,15,16-dodecahydrocyclopenta[a]phenanthrene-3,2'-1,3-dithiolane]-17-ol (17 mg, 0.030 mmol) (Step H) in acetic acid (1.1 mL) was added glyoxylic acid hydrate (142 mg, 1.55 mmol) under argon at rt and the mixture was stirred for 10 min. Then 4 N aqueous HCl solution (0.14 mL) was added and the resulting solution was stirred at rt for 20 min. The reaction was quenched (sat. aq. NaHCO$_3$), extracted (2×EtOAc), and washed (brine). The combined organic layer was dried (Na$_2$SO$_4$) and concentrated under reduced pressure. Purification of the residue with combi-flash (4 g SiO$_2$, 20% to 50% EtOAc/hexanes) provided the title compound (5.9 mg, 0.013 mmol, 40% yield) as a white solid. $^1$H NMR (400 MHz, CHLOROFORM-d) δ ppm 7.28 (2 H, br d, J=8.4 Hz), 6.67 (2 H, br d, J=8.4 Hz), 5.87 (1 H, s), 3.34 (1 H, br t, J=6.0 Hz), 2.95 (6 H, s), 2.80-2.90 (1 H, m), 2.49-2.57 (1 H, m), 2.33-2.43 (1 H, m), 2.22-2.30 (2 H, m), 2.02-2.22 (4 H, m), 1.87-1.97 (3 H, m), 1.68-1.79 (1 H, m), 1.60-1.67 (1 H, m), 1.47-1.54 (2 H, m), 1.38 (1 H, m, J=11.9, 5.7, 5.7 Hz), 1.26-1.30 (1 H, m), 1.24 (9 H, s), 1.06-1.16 (1 H, m), 0.67 (3 H, s); m/z (ESI, +ve ion) 474.4 (M+H)+.

Examples 10-13 were prepared by procedures similar to those described in Example 9, substituting [4-(dimethylamino)phenyl]magnesium bromide with the appropriate arylmagnesium bromide in Step C and 3,3-dimethylbut-1-yne with the appropriate alkyne in Step H.

Example 10

Compound 4. (8R,9S,10R,11S,13S,14S,17S)-17-(3, 3-Dimethylbut-1-yn-1-yl)-17-hydroxy-13-methyl-11-(p-tolyl)-1,2,6,7,8,9,10,11,12,13,14,15,16,17-tetradecahydro-3H-cyclopenta[a]phenanthren-3-one

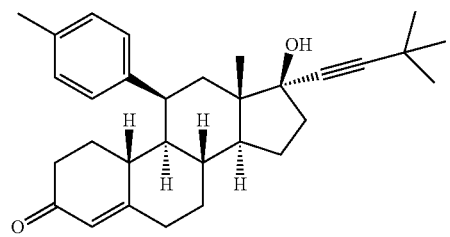

$^1$H NMR (400 MHz, CHLOROFORM-d) δ 7.30 (d, J=8.01 Hz, 2H), 7.08 (d, J=8.01 Hz, 2H), 5.86 (s, 1H), 3.38 (br t, J=5.76 Hz, 1H), 2.84 (m, 1H), 2.50-2.56 (m, 1H), 2.37-2.43 (m, 1H), 2.23-2.35 (m, 5H), 2.02-2.21 (m, 4H), 1.83-1.95 (m, 3H), 1.66-1.77 (m, 1H), 1.44-1.55 (m, 2H), 1.16-1.32 (m, 11H), 1.09-1.14 (m, 1H), 0.62 (s, 3H); m/z (ESI, +ve ion)=445.4 [M+H]+.

Example 11

Compound 5. (8R,9S,10R,11S,13S,14S,17S)-11-(3, 5-Difluoro-4-methylphenyl)-17-hydroxy-13-methyl-17-(prop-1-yn-1-yl)-1,2,6,7,8,9,10,11,12,13,14,15, 16,17-tetradecahydro-3H-cyclopenta[a]phenanthren-3-one

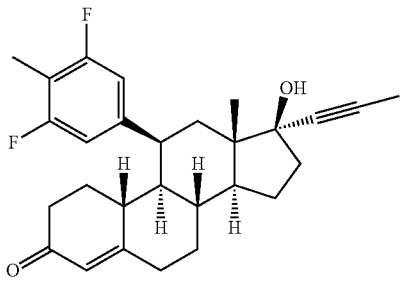

$^1$H NMR (400 MHz, CHLOROFORM-d) δ 6.90 (br d, J=8.59 Hz, 2H), 5.87 (s, 1H), 3.26-3.43 (m, 1H), 2.69-2.87 (m, 1H), 2.52 (br s, 1H), 2.27-2.41 (m, 3H), 2.00-2.25 (m, 8H), 1.83-1.96 (m, 6H), 1.44-1.64 (m, 2H), 1.31-1.44 (m, 2H), 1.09-1.19 (m, 1H), 0.63 (s, 3H); m/z (ESI, +ve ion)= 439.3 [M+H]+.

Example 12

Compound 8 (8R,9S,10R,11S,13S,14S,17S)-17-Hydroxy-13-methyl-17-(prop-1-yn-1-yl)-11-(p-tolyl)-1,2,6,7,8,9,10,11,12,13,14,15,16,17-tetradecahydro-3H-cyclopenta[a]phenanthren-3-one

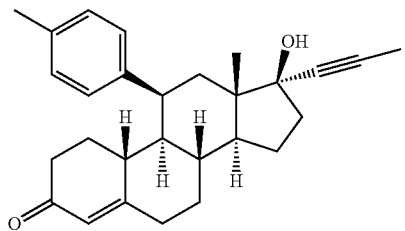

$^1$H NMR (400 MHz, CHLOROFORM-d) δ 7.25-7.31 (d, J=7.86 Hz, 2H), 7.08 (d, J=7.81 Hz, 2H), 5.85 (s, 1H), 3.38 (br t, J=5.66 Hz, 1H), 2.83 (br s, 1H), 2.49-2.56 (m, 1H), 2.38 (br d, J=3.71 Hz, 1H), 2.16-2.33 (m, 6H), 2.01-2.13 (m, 3H), 1.83-1.95 (m, 6H), 1.45-1.78 (m, 3H), 1.32-1.42 (m, 2H), 1.14 (m, 1H), 0.62 (s, 3H); m/z (ESI, +ve ion)=403.4 [M+H]$^+$.

Example 13

Compound 10. (8R,9S,10R,11S,13S,14S,17S)-11-(4-(Dimethylamino)phenyl)-17-hydroxy-17-(3-methoxy-3-methylbut-1-yn-1-yl)-13-methyl-1,2,6,7,8,9,10,11,12,13,14,15,16,17-tetradecahydro-3H-cyclopenta[a]phenanthren-3-one

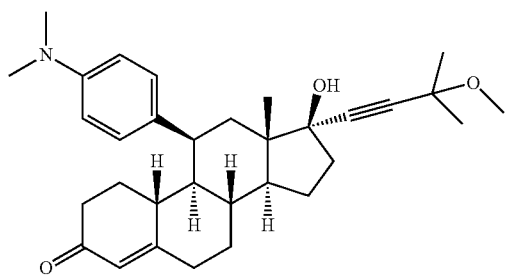

$^1$H NMR (400 MHz, CHLOROFORM-d) δ ppm 7.26-7.31 (2 H, m), 6.61-6.74 (2 H, m), 5.86 (1 H, s), 3.37 (3 H, s), 3.32-3.36 (1 H, m), 2.96 (3 H, br s), 2.96 (3 H, br s), 2.80-2.89 (1 H, m), 2.50-2.58 (1 H, m), 2.33-2.43 (1 H, m), 2.19-2.31 (3 H, m), 2.01-2.15 (3 H, m), 1.87-1.98 (3 H, m), 1.72-1.80 (1 H, m), 1.70 (1 H, s), 1.52 (1 H, br d, J=7.6 Hz), 1.48 (3 H, s), 1.48 (3 H, s), 1.37-1.45 (2 H, m), 1.22-1.32 (1 H, m), 1.05-1.15 (1 H, m), 0.68 (3 H, s); m/z (ESI, +ve ion)=490.4 [M+H]$^+$.

II. Biological Evaluation

Example 14

In Vitro GR Luciferase Reporter Assay

Cell Line: CHO-K1-GR-MMTV-Luc reporter cells
Culture Media: DMEM (with phenol red)+10% FBS
Assay Media: DMEM (without phenol red)+10% CSS Culture CHO-K1-GR-MMTV-Luc reporter cells in 15 cm plates in Culture Media at conditions less than 90% confluence.

Prepare 200× DMSO 1:5 serial dilutions of control and test compounds in 96-well non-sterile V bottom plate in DMSO, 8 serial dilutions for each compound.

Prepare 5× Assay Media diluted compound serial dilutions in 96-well non-sterile V bottom plate: Add 97.5 uL/well of Assay Media into 96-well then add 2.5 ul of 200× concentration of compounds and mix well.

Seed cells for Antagonist Assay: 1.5×10$^6$ CHO-K1-GR-MMTV-Luc reporter cells were seeded in a Corning 3707 flat clear bottom 384-well white TC plate in 20 ul of Assay Media containing 12.5 nM Dexamethasone (final concentration=10 nM).

Add compounds: 5 ul of assay media diluted compounds were added to appropriate wells and followed a quick spin (1000 rpm, 10 sec) to bring media and cells to the bottom of plate. The plates were covered with SealMate film to avoid evaporation and placed in 37° C. incubator for approximately 18-24 hours.

Read plates: Equilibrate appropriate amount of Promega OneGlo luciferase reagent to room temperature. Remove the plates from incubator and add 25 uL of OneGlo reagent/well by multiple channel pipette and read the plates with Tecan F500 luminometer within 3 minutes.

The ability of the compounds disclosed herein to inhibit GR activity was quantified and the respective IC$_{50}$ value was determined. Table 3 provides the cellular IC$_{50}$ values of various substituted steroidal compounds disclosed herein.

TABLE 3

| No. | GR IC$_{50}$ (nM) | No. | GR IC$_{50}$ (nM) |
| --- | --- | --- | --- |
| 1 | A | 2 | B |
| 3 | A | 4 | A |
| 5 | B | 6 | B |
| 7 | A | 8 | A |
| 9 | B | 10 | A |
| 11 | A | 12 | A |
| 13 | B | 14 | B |
| 15 | A | 16 | A |

Example 15

In Vitro AR Agonism Assay

The AR agonism assay was done in the LNAR reporter cell line which has overexpressed AR and 4×ARE-Luc genes. This cell line is sensitive to even minor partial AR agonism activity in hormone-deprived media (CSS). The assays were done in RPMI (without phenol red)+10% CSS using 6000 LNAR cells/well in 384-well plates and compounds were incubated with cells in 370 C incubator for 18-24 hrs. OneGlo reagent (25 uL/well) was added and plates were read with luminometer within 3 minutes.

Mifepristone shows strong partial AR agonism in concentrations as low as 10 nM, and is known to significantly promote CRPC growth both in vivo and in vitro. To gauge the AR partial agonism activity, Mifepristone is included as a standard in the assay. AR agonism assay results are quantified by determining the ratio of the maximum response of individual compounds to the maximum response of Mifepristone (arbitrarily set to 1). Values of Table 4 are reported as Relative Maximum Response to Mifepristone.

This general trend of AR agonism was shown for the class of compounds described herein.

TABLE 4

| No. | Relative Maximum Response to Mifepristone |
|---|---|
| 3 | B |
| 6 | A |
| 7 | A |
| 10 | A |
| 13 | A |

Note:
AR agonism response assay data relative maximum response to Mifepristone is designated within the following ranges:
A: ≤0.4
B: >0.4

What is claimed is:

1. A compound having the structure of Formula (I), or a pharmaceutically acceptable salt, solvate, or prodrug thereof:

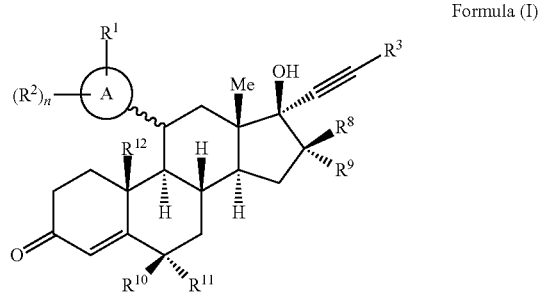

Formula (I)

wherein
ring A is a heteroaryl, aryl, cycloalkyl, or heterocyclyl;
$R^1$ is —H, —$NR^4R^5$, optionally substituted alkylN$R^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)O$R^6$, —C(O)N$R^4R^5$, —OC(O)O$R^6$, —OC(O)N$R^4R^5$, —S(O)$_2$N$R^4R^5$, —S(O)$_2R^7$, —S(O)$R^7$, —S$R^7$, —N$R^4$S(O)$_2$N$R^4R^5$, —P(O)(O$R^6$)$_2$, —P(O)($R^6$)$_2$, —CN, —CO$_2$H, or —NO$_2$;
each $R^2$ is independently —N$R^4R^5$, optionally substituted alkylN$R^4R^5$, halo, —O$R^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxy alkyl, —C(O)$R^6$, —C(O)O$R^6$, —C(O)N$R^4R^5$, —OC(O)O$R^6$, —OC(O)N$R^4R^5$, —S(O)$_2$N$R^4R^5$, —S(O)$_2R^7$, —S(O)$R^7$, —S$R^7$, —N$R^4$S(O)$_2$N$R^4R^5$, —CN, —CO$_2$H, or —NO$_2$;
$R^3$ is $C_{2-8}$alkyl;
$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2R^7$, —C(O)N($R^{13}$)$_2$, —C(O)$R^6$, or —C(O)O$R^6$;
or $R^4$ and $R^5$ attached to the same N atom are taken together with the N atom to which they are attached to form a substituted or unsubstituted heterocycle;
each $R^6$ is independently optionally substituted alkyl, haloalkyl, optionally substituted carbocyclyl, optionally substituted aryl, optionally substituted heterocyclyl, or optionally substituted heteroxyl;
$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;
$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclyl —OH, —S(O)$_2R^7$, —C(O)$_2$H, —C(O)$R^6$, or —C(O)O$R^6$;
or $R^8$ and $R^9$ are taken together with the atom to which they are attached to form a substituted or unsubstituted ring containing 0-2 heteroatoms selected from the group consisting of —O—, —NH—, —N$R^6$—, —S—, and —S(O)$_2$—;
$R^{10}$ and $R^{11}$ are each independently —H, optionally substituted alkyl, halo, haloalkyl, optionally substituted carbocyclyl, optionally substituted carbocyclylalkyl, optionally substituted heteroalkyl, optionally substituted heterocyclyl, optionally substituted heterocyclylalkyl, —OH, —S(O)$_2R^7$, —C(O)$_2$H, —C(O)$R^6$, or —C(O)O$R^6$;
or $R^{10}$ and $R^{11}$ are taken together with the atom to which they are attached to form a substituted or unsubstituted ring containing 0-2 heteroatoms selected from the group consisting of —O—, —NH—, —N$R^6$—, —S—, and —S(O)$_2$—;
$R^{12}$ is optionally substituted alkyl, haloalkyl, hydroxy, halo, optionally substituted carbocyclyl, optionally substituted carbocyclylalkyl, optionally substituted heterocyclyl, optionally substituted heterocyclylalkyl or optionally substituted heteroalkyl;
each $R^{13}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;
and n is 0, 1, 2, 3, or 4, provided that $R^3$ is not tert-butyl.

2. The compound of claim 1 or a pharmaceutically acceptable salt, solvate, or prodrug thereof, wherein $R^{12}$ is alkyl, haloalkyl, hydroxy, halo, carbocyclyl, or heteroalkyl.

3. The compound of claim 1, or a pharmaceutically acceptable salt, solvate, or prodrug thereof, wherein $R^{12}$ is $C_{1-6}$alkyl.

4. The compound of claim 1, or a pharmaceutically acceptable salt, solvate, or prodrug thereof, wherein $R^{12}$ is methyl.

5. The compound of claim 1, or a pharmaceutically acceptable salt, solvate, or prodrug thereof, wherein $R^{12}$ is methyl and $R^{10}$ and $R^{11}$ are H.

6. The compound of claim 1, or a pharmaceutically acceptable salt, solvate, or prodrug thereof, wherein ring A is monocyclic heteroaryl or monocyclic aryl.

7. The compound of claim 1, or a pharmaceutically acceptable salt, solvate, or prodrug thereof, wherein ring A is phenyl, pyridinyl, pyrimidinyl pyrazinyl, or pyridazinyl.

8. The compound of claim 1, or a pharmaceutically acceptable salt, solvate, or prodrug thereof, wherein ring A is bicyclic heteroaryl or bicyclic aryl.

9. The compound of claim 1, or a pharmaceutically acceptable salt, solvate, or prodrug thereof, wherein $R^1$ is —$NR^4R^5$, halo, —$OR^6$, alkyl, fluoroalkyl, carbocyclyl, heteroalkyl, heterocyclyl, —$S(O)_2NR^4R^5$, —$S(O)_2R^7$, or —CN.

10. The compound of claim 1, or a pharmaceutically acceptable salt, solvate, or prodrug thereof, wherein each $R^2$ is independently —$NR^4R^5$, halo, —$OR^6$, alkyl, fluoroalkyl, carbocyclyl, heteroalkyl, heterocyclyl, —$S(O)_2NR^4R^5$, or —$S(O)_2R^7$.

11. The compound of claim 1, or a pharmaceutically acceptable salt, solvate, or prodrug thereof, wherein $R^4$ and $R^5$ are each independently —H, $C_{1-6}$alkyl, or —$S(O)_2R^7$.

12. The compound of claim 1, or a pharmaceutically acceptable salt, solvate, or prodrug thereof, wherein $R^4$ and $R^5$ attached to the same N atom are taken together with the N atom to which they are attached to form a substituted or unsubstituted 4-, 5-, or 6- membered ring heterocycle additionally containing 0-3 heteroatoms selected from the group consisting of —O—, —NH—, —$NR^6$—, —S—, and —$S(O)_2$—.

13. The compound of claim 1, or a pharmaceutically acceptable salt, solvate, or prod rug thereof, wherein $R^6$ is alkyl, carbocyclyl, or fluoroalkyl.

14. The compound of claim 1, or a pharmaceutically acceptable salt, solvate, or prodrug thereof, wherein $R^7$ is alkyl, carbocyclyl, optionally substituted aryl, optionally substituted aralkyl, or optionally substituted heterocyclyl.

15. The compound of claim 1, or a pharmaceutically acceptable salt, solvate, or prodrug thereof, wherein $R^8$ and $R^9$ are each independently —H, alkyl, or carbocyclyl.

16. The compound of claim 1, or a pharmaceutically acceptable salt, solvate, or prodrug thereof, wherein $R^8$ and $R^9$ are —H.

17. The compound of claim 1, or a pharmaceutically acceptable salt, solvate, or prodrug thereof, wherein $R^{10}$ and $R^{11}$ are each independently —H, $C_{1-6}$alkyl, halo, $C_{1-6}$ alkoxy, or —OH.

18. The compound of claim 1, or a pharmaceutically acceptable salt, solvate, or prodrug thereof, wherein $R^{10}$ and $R^{11}$ are taken together with the atom to which they are attached to form a 3-, 4-, 5-, or 6- membered ring.

19. The compound of claim 1, or a pharmaceutically acceptable salt, solvate, or prodrug thereof, wherein n is 0, 1, or 2.

20. The compound of claim 1, or a pharmaceutically acceptable salt, solvate, or prodrug thereof, wherein the compound has the structure of Formula (Ia):

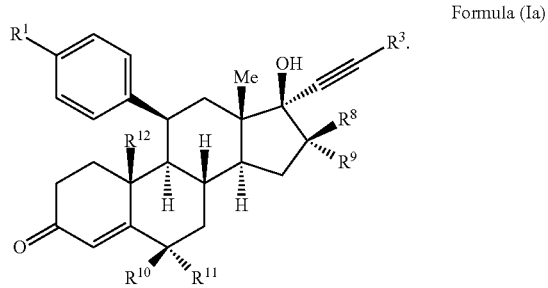

Formula (Ia)

21. A compound of claim 1, or a pharmaceutically acceptable salt, solvate, or prodrug thereof, wherein the compound has the structure:

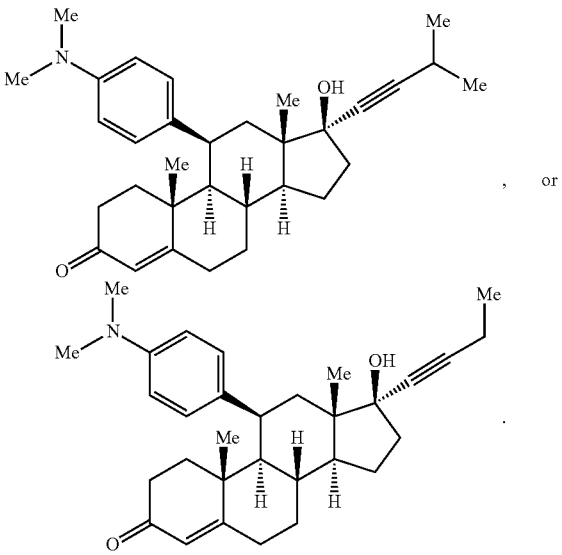

22. A pharmaceutical composition comprising a compound of claim 1, or a pharmaceutically acceptable salt, solvate, or prodrug thereof, and at least one pharmaceutically acceptable excipient.

23. The compound of claim 1, or a pharmaceutically acceptable salt, solvate, or prodrug thereof, wherein $R^8$, $R^9$, $R^{10}$, and $R^{11}$ are hydrogen and $R^{12}$ is methyl.

24. The compound of claim 1, or a pharmaceutically acceptable salt, solvate, or prodrug thereof, wherein $R^1$ is —$NR^4R^5$; $R^8$ is H; $R^9$ is H; $R^{10}$ is H; $R^{11}$ is H; $R^{12}$ is methyl; and n is 0.

25. The compound of claim 24, or a pharmaceutically acceptable salt, solvate, or prodrug thereof, wherein $R^4$ and $R^5$ are each independently H or $C_{1-6}$alkyl.

26. The compound of claim 25, or a pharmaceutically acceptable salt, solvate, or prodrug thereof, wherein $R^4$ and $R^5$ are $C_{1-6}$alkyl.

27. The compound of claim 24, or a pharmaceutically acceptable salt, solvate, or prodrug thereof, wherein $R^{12}$ is methyl.

28. The compound of claim 27, or a pharmaceutically acceptable salt, solvate, or prodrug thereof, wherein $R^4$ and $R^5$ are each independently H or $C_{1-6}$alkyl.

29. The compound of claim 28, ora pharmaceutically acceptable salt, solvate, or prodrug thereof, wherein $R^4$ and $R^5$ are $C_{1-6}$alkyl.

30. The compound of claim 24, or a pharmaceutically acceptable salt, solvate, or prodrug thereof, wherein $R^3$ is ethyl, n-propyl, iso-propyl, n-butyl, or iso-butyl.

31. The compound of claim 30, or a pharmaceutically acceptable salt, solvate, or prodrug thereof, wherein $R^3$ is ethyl or iso-propyl.

32. The compound of claim 24, or a pharmaceutically acceptable salt, solvate, or prodrug thereof, wherein $R^4$ and $R^5$ are $C_{1-6}$alkyl.

33. The compound of claim 32, or a pharmaceutically acceptable salt, solvate, or prodrug thereof, wherein $R^3$ is ethyl, n-propyl, iso-propyl, n-butyl, or iso-butyl.

34. The compound of claim 33, or a pharmaceutically acceptable salt, solvate, or prodrug thereof, wherein $R^3$ is ethyl or iso-propyl.

35. A pharmaceutical composition comprising a compound of claim 20, or a pharmaceutically acceptable salt, solvate, or prodrug thereof, and at least one pharmaceutically acceptable excipient.

* * * * *

UNITED STATES PATENT AND TRADEMARK OFFICE
CERTIFICATE OF CORRECTION

PATENT NO. : 11,208,432 B2
APPLICATION NO. : 16/065627
DATED : December 28, 2021
INVENTOR(S) : Sun et al.

Page 1 of 1

It is certified that error appears in the above-identified patent and that said Letters Patent is hereby corrected as shown below:

In the Claims

Column 80, Line 7:
In Claim 1, replace "optionally substituted heteroxyl" with --optionally substituted heteroaryl--

Column 80, Line 14:
In Claim 1, replace "haloalkyl,halo" with --haloalkyl, halo--

Column 80, Lines 16 or 17:
In Claim 1, replace "optionally substituted heterocyclyl, optionally substituted heterocyclyl" with --optionally substituted heterocyclyl, optionally substituted hetero cyclylalkyl,--

Column 82, Lines 52 or 53:
In Claim 29, replace "The compound of claim 28, ora pharmaceutically acceptable salt, solvate, or prodrug thereof" with --The compound of claim 28, or a pharmaceutically acceptable salt, solvate, or prodrug thereof--

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*